United States Patent
Gombert et al.

(10) Patent No.: US 9,109,009 B2
(45) Date of Patent: Aug. 18, 2015

(54) TEMPLATE-FIXED PEPTIDOMIMETICS WITH CXCR7 MODULATING ACTIVITY

(75) Inventors: Frank Otto Gombert, Binningen (CH); Alexander Lederer, Basel (CH); Ralf Löwe, Arlesheim (CH); Daniel Obrecht, Bättwil (CH); Barbara Romagnoli, Binningen (CH); Johann Zimmermann, Auggen (DE); Kalpana Patel, Steinsoultz (FR)

(73) Assignee: POLYPHOR AG, Allschwil (CH)

( * ) Notice: Subject to any disclaimer, the term of this patent is extended or adjusted under 35 U.S.C. 154(b) by 150 days.

(21) Appl. No.: 13/577,143

(22) PCT Filed: Feb. 4, 2011

(86) PCT No.: PCT/EP2011/051686
§ 371 (c)(1),
(2), (4) Date: Oct. 1, 2012

(87) PCT Pub. No.: WO2011/095607
PCT Pub. Date: Aug. 11, 2011

(65) Prior Publication Data
US 2013/0225506 A1      Aug. 29, 2013

(30) Foreign Application Priority Data
Feb. 5, 2010   (WO) ................. PCT/EP2010/051417

(51) Int. Cl.
| | |
|---|---|
| *A61K 38/12* | (2006.01) |
| *C07K 7/64* | (2006.01) |
| *C07K 14/715* | (2006.01) |
| *C07K 14/705* | (2006.01) |
| *A61K 38/00* | (2006.01) |
| *A61K 38/17* | (2006.01) |

(52) U.S. Cl.
CPC . *C07K 7/64* (2013.01); *A61K 38/00* (2013.01); *A61K 38/17* (2013.01); *A61K 38/177* (2013.01); *A61K 38/1793* (2013.01); *C07K 14/705* (2013.01); *C07K 14/715* (2013.01); *C07K 14/7158* (2013.01)

(58) Field of Classification Search
CPC ...... C07K 7/64; C07K 14/7158; A61K 38/00; A61K 38/1793; A61K 38/177; A61K 38/17
See application file for complete search history.

(56) References Cited

FOREIGN PATENT DOCUMENTS

| WO | WO 02/066500 A2 | 8/2002 | |
|---|---|---|---|
| WO | WO/2005/035568 | * 4/2005 | ........... C07K 14/705 |
| WO | WO 2008/092281 A1 | 8/2008 | |
| WO | WO 2008092281 A1 * | 8/2008 | |

OTHER PUBLICATIONS

Narumi et al., Organic & Biomolecular Chemistry (2010) 8, 616-621.*
Galzi et al., "Neutralizing endogenous chemokines with small molecules: Principles and potential therapeutic applications," Pharmacology & Therapeutics, vol. 126, pp. 39-55, 2010.
International Search Report for International Patent Application No. PCT/EP2011/051686, dated Apr. 26, 2011.
Krstenansky et al., "Cyclic hexapeptide antagonists of the bradykinin B2 receptor: Receptor binding and solution backbone conformation," Letters in Peptide Science, vol. 1, pp. 229-234, 1994.

* cited by examiner

*Primary Examiner* — Karlheinz R Skowronek
*Assistant Examiner* — Catherine Mader
(74) *Attorney, Agent, or Firm* — Birch, Stewart, Kolasch & Birch, LLP

(57) ABSTRACT

Novel template-fixed β-hairpin peptidomimetics of the general formula (I), wherein the single elements T or P are α-amino acid residues connected from the carbonyl (C=O) point of attachment to the nitrogen (N) of the next element in clockwise direction and wherein said elements, depending on their positions in the chain, are defined in the description and the claims have the property to act on the receptor CXCR7. Thus, these β-hairpin peptidomimetics can be useful in the treatment or prevention of diseases or conditions in the area of dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases and cancer; or the mobilization of stem cells.

(I)

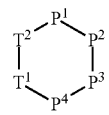

18 Claims, No Drawings

SEQUENCE LISTING

```
<160> NUMBER OF SEQ ID NOS: 80

<210> SEQ ID NO 1
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 1

Ile Xaa Arg Ile Xaa Thr
1               5
```

```
<210> SEQ ID NO 2
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 2

Ile Xaa Arg Tyr Xaa Thr
1               5

<210> SEQ ID NO 3
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 3

Ile Xaa Lys Trp Xaa Thr
1               5

<210> SEQ ID NO 4
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Dab
<220> FEATURE:
<221> NAME/KEY: Misc_feature
<222> LOCATION: (5)..(5)
<223> OTHER INFORMATION: Xaa is D-Pro

<400> SEQUENCE: 4

Ile Xaa Xaa Trp Xaa Thr
1               5

<210> SEQ ID NO 5
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
```

```
<221> NAME/KEY: Misc_feature
<222> LOCATION: (2)..(2)
<223> OTHER INFORMATION: Xaa is D-Dab
<220> FEATURE:
<221> NAME/KEY: Misc_feature
<222> LOCATION: (5)..(5)
<223> OTHER INFORMATION: Xaa is D-Pro

<400> SEQUENCE: 5

Ile Xaa Arg Trp Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 6

Ile Xaa Arg Phe Xaa Thr
1               5

<210> SEQ ID NO 7
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Thr
<220> FEATURE:
<221> NAME/KEY: Misc_feature
<222> LOCATION: (5)..(5)
<223> OTHER INFORMATION: Xaa is D-Pro

<400> SEQUENCE: 7

Ile Xaa Arg Trp Xaa Thr
1               5

<210> SEQ ID NO 8
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is hSer

<400> SEQUENCE: 8
```

```
Ile Xaa Arg Trp Xaa Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is alloThr

<400> SEQUENCE: 9

Ile Xaa Arg Trp Xaa Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is 1Nal
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 10

Xaa Xaa Arg Trp Xaa Thr
1               5

<210> SEQ ID NO 11
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Lys
<220> FEATURE:
<221> NAME/KEY: Misc_feature
<222> LOCATION: (5)..(5)
<223> OTHER INFORMATION: Xaa is D-Pro

<400> SEQUENCE: 11

Ile Xaa Arg Trp Xaa Thr
1               5
```

```
<210> SEQ ID NO 12
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-His
<220> FEATURE:
<221> NAME/KEY: Misc_feature
<222> LOCATION: (5)..(5)
<223> OTHER INFORMATION: Xaa is D-Pro

<400> SEQUENCE: 12

Ile Xaa Arg Trp Xaa Thr
1               5

<210> SEQ ID NO 13
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Cit
<220> FEATURE:
<221> NAME/KEY: Misc_feature
<222> LOCATION: (5)..(5)
<223> OTHER INFORMATION: Xaa is D-Pro

<400> SEQUENCE: 13

Ile Xaa Arg Trp Xaa Thr
1               5

<210> SEQ ID NO 14
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pip

<400> SEQUENCE: 14

Ile Xaa Arg Trp Xaa Thr
1               5

<210> SEQ ID NO 15
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
```

```
<222> LOCATION: (4)..(4)
<223> OTHER INFORMATION: Xaa is 2Nal
<220> FEATURE:
<221> NAME/KEY: Misc_feature
<222> LOCATION: (5)..(5)
<223> OTHER INFORMATION: Xaa is D-Pro

<400> SEQUENCE: 15

Ile Xaa Arg Xaa Xaa Thr
1               5

<210> SEQ ID NO 16
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (4)..(4)
<223> OTHER INFORMATION: Xaa is 1Nal
<220> FEATURE:
<221> NAME/KEY: Misc_feature
<222> LOCATION: (5)..(5)
<223> OTHER INFORMATION: Xaa is D-Pro

<400> SEQUENCE: 16

Ile Xaa Arg Xaa Xaa Thr
1               5

<210> SEQ ID NO 17
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 17

Ile Xaa Trp Arg Xaa Thr
1               5

<210> SEQ ID NO 18
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 18
```

Ile Xaa Arg Trp Xaa Thr
1               5

<210> SEQ ID NO 19
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 19

Thr Xaa Trp Arg Xaa Thr
1               5

<210> SEQ ID NO 20
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 20

Trp Xaa Arg Trp Xaa Thr
1               5

<210> SEQ ID NO 21
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Pro((3S)OH)

<400> SEQUENCE: 21

Ile Xaa Arg Trp Xaa Xaa
1               5

<210> SEQ ID NO 22
<211> LENGTH: 6
<212> TYPE: PRT
<213> ORGANISM: Artificial Sequence
<220> FEATURE:

<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 22

Ile Xaa Arg Trp Xaa Ser
1               5

<210> SEQ ID NO 23
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Agp
<220> FEATURE:
<221> NAME/KEY: Misc_feature
<222> LOCATION: (5)..(5)
<223> OTHER INFORMATION: Xaa is D-Pro

<400> SEQUENCE: 23

Ile Xaa Xaa Trp Xaa Thr
1               5

<210> SEQ ID NO 24
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Agb
<220> FEATURE:
<221> NAME/KEY: Misc_feature
<222> LOCATION: (5)..(5)
<223> OTHER INFORMATION: Xaa is D-Pro

<400> SEQUENCE: 24

Ile Xaa Xaa Trp Xaa Thr
1               5

<210> SEQ ID NO 25
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)

```
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4S)NH2)
<220> FEATURE:
<221> NAME/KEY: Misc_feature
<222> LOCATION: (6)..(6)
<223> OTHER INFORMATION: Xaa is Tic

<400> SEQUENCE: 25

Trp Xaa Trp Arg Xaa Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 26

Trp Xaa Trp Arg Xaa Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 27

Ala Xaa Trp Arg Xaa Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
```

```
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 28

Tyr Xaa Trp Arg Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is Orn
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 29

Trp Xaa Trp Xaa Xaa Xaa
1               5

<210> SEQ ID NO 30
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is Dab
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 30

Trp Xaa Trp Xaa Xaa Xaa
1               5

<210> SEQ ID NO 31
<211> LENGTH: 6
<212> TYPE: PRT
<213> ORGANISM: Artificial Sequence
```

```
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 31

Trp Xaa Trp Lys Xaa Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 32

Trp Xaa Trp His Xaa Xaa
1               5

<210> SEQ ID NO 33
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 33

Arg Xaa Trp Arg Xaa Xaa
1               5

<210> SEQ ID NO 34
<211> LENGTH: 6
<212> TYPE: PRT
<213> ORGANISM: Artificial Sequence
<220> FEATURE:
```

```
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Pip
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 34

Xaa Xaa Trp Arg Xaa Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is hArg
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 35

Xaa Xaa Trp Arg Xaa Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Agb
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic
```

```
<400> SEQUENCE: 36

Xaa Xaa Trp Arg Xaa Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is 3Pal
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 37

Xaa Xaa Trp Arg Xaa Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-3Pal
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 38

Trp Xaa Trp Arg Xaa Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is hArg
<220> FEATURE:
<221> NAME/KEY: Misc_feature
```

```
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 39

Arg Xaa Trp Xaa Xaa Xaa
1               5

<210> SEQ ID NO 40
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4S)NH2)
<220> FEATURE:
<221> NAME/KEY: Misc_feature
<222> LOCATION: (6)..(6)
<223> OTHER INFORMATION: Xaa is Tic

<400> SEQUENCE: 40

Arg Xaa Trp Arg Xaa Xaa
1               5

<210> SEQ ID NO 41
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Oic

<400> SEQUENCE: 41

Trp Xaa Trp Arg Xaa Xaa
1               5

<210> SEQ ID NO 42
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
```

```
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Oic

<400> SEQUENCE: 42

Arg Xaa Trp Arg Xaa Xaa
1               5

<210> SEQ ID NO 43
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Pro((4S)F)

<400> SEQUENCE: 43

Trp Xaa Trp Arg Xaa Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Pro((4S)NH2)

<400> SEQUENCE: 44

Trp Xaa Trp Arg Xaa Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro
```

```
<220> FEATURE:
<221> NAME/KEY: Misc_feature
<222> LOCATION: (6)..(6)
<223> OTHER INFORMATION: Xaa is Pro((4R)NH2)

<400> SEQUENCE: 45

Trp Xaa Trp Arg Xaa Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Mor

<400> SEQUENCE: 46

Trp Xaa Trp Arg Xaa Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Mor

<400> SEQUENCE: 47

Ile Xaa Arg Trp Xaa Xaa
1               5

<210> SEQ ID NO 48
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro
<220> FEATURE:
```

```
<221> NAME/KEY: Misc_feature
<222> LOCATION: (6)..(6)
<223> OTHER INFORMATION: Xaa is (4S)-Hyp(Bn)

<400> SEQUENCE: 48

Arg Xaa Trp Arg Xaa Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4S)OH)
<220> FEATURE:
<221> NAME/KEY: Misc_feature
<222> LOCATION: (6)..(6)
<223> OTHER INFORMATION: Xaa is (4S)-Hyp(Bn)

<400> SEQUENCE: 49

Trp Xaa Trp Arg Xaa Xaa
1               5

<210> SEQ ID NO 50
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is (4S)-Hyp(Bn)

<400> SEQUENCE: 50

Trp Xaa Trp Arg Xaa Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Trp
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
```

```
<222> LOCATION: (6)..(6)
<223> OTHER INFORMATION: Xaa is Pro((4S)NHBz)

<400> SEQUENCE: 51

His Xaa His Trp Xaa Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is 1Nal
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Pro((3S)OH)

<400> SEQUENCE: 52

Xaa Xaa Arg Trp Xaa Xaa
1               5

<210> SEQ ID NO 53
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (4)..(4)
<223> OTHER INFORMATION: Xaa is 2Nal
<220> FEATURE:
<221> NAME/KEY: Misc_feature
<222> LOCATION: (5)..(5)
<223> OTHER INFORMATION: Xaa is D-Pro
<220> FEATURE:
<221> NAME/KEY: Misc_feature
<222> LOCATION: (6)..(6)
<223> OTHER INFORMATION: Xaa is Pro((3S)OH)

<400> SEQUENCE: 53

Ile Xaa Arg Xaa Xaa Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
```

```
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pip
<220> FEATURE:
<221> NAME/KEY: Misc_feature
<222> LOCATION: (6)..(6)
<223> OTHER INFORMATION: Xaa is Pro((3S)OH)

<400> SEQUENCE: 54

Ile Xaa Arg Trp Xaa Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro((4S)OH)

<400> SEQUENCE: 55

Ile Xaa Arg Trp Xaa Thr
1               5

<210> SEQ ID NO 56
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro((4R)NH2)

<400> SEQUENCE: 56

Ile Xaa Arg Trp Xaa Thr
1               5

<210> SEQ ID NO 57
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 57

Val Xaa Arg Trp Xaa Thr
```

<210> SEQ ID NO 58
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Abu
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 58

Xaa Xaa Arg Trp Xaa Thr
1               5

<210> SEQ ID NO 59
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Chg
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 59

Xaa Xaa Arg Trp Xaa Thr
1               5

<210> SEQ ID NO 60
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 60

Leu Xaa Arg Trp Xaa Thr
1               5

<210> SEQ ID NO 61
<211> LENGTH: 6

```
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Nle
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 61

Xaa Xaa Arg Trp Xaa Thr
1               5

<210> SEQ ID NO 62
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Cha
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Pro

<400> SEQUENCE: 62

Xaa Xaa Arg Trp Xaa Thr
1               5

<210> SEQ ID NO 63
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Orn
<220> FEATURE:
<221> NAME/KEY: Misc_feature
<222> LOCATION: (5)..(5)
<223> OTHER INFORMATION: Xaa is D-Pro

<400> SEQUENCE: 63

Ile Xaa Arg Trp Xaa Thr
1               5

<210> SEQ ID NO 64
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
```

```
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Orn(A41)
<220> FEATURE:
<221> NAME/KEY: Misc_feature
<222> LOCATION: (5)..(5)
<223> OTHER INFORMATION: Xaa is D-Pro

<400> SEQUENCE: 64

Ile Xaa Xaa Trp Xaa Thr
1               5

<210> SEQ ID NO 65
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Orn
<220> FEATURE:
<221> NAME/KEY: Misc_feature
<222> LOCATION: (5)..(5)
<223> OTHER INFORMATION: Xaa is D-Pro

<400> SEQUENCE: 65

Ile Xaa Xaa Trp Xaa Thr
1               5

<210> SEQ ID NO 66
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is hArg
<220> FEATURE:
<221> NAME/KEY: Misc_feature
<222> LOCATION: (5)..(5)
<223> OTHER INFORMATION: Xaa is D-Pro

<400> SEQUENCE: 66

Ile Xaa Xaa Trp Xaa Thr
1               5

<210> SEQ ID NO 67
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
```

```
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (5)..(5)
<223> OTHER INFORMATION: Xaa is D-Tic

<400> SEQUENCE: 67

Ile Xaa Arg Trp Xaa Thr
1               5

<210> SEQ ID NO 68
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Orn(Ar2)
<220> FEATURE:
<221> NAME/KEY: Misc_feature
<222> LOCATION: (5)..(5)
<223> OTHER INFORMATION: Xaa is D-Pro

<400> SEQUENCE: 68

Ile Xaa Xaa Trp Xaa Thr
1               5

<210> SEQ ID NO 69
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Orn(Ar7)
<220> FEATURE:
<221> NAME/KEY: Misc_feature
<222> LOCATION: (5)..(5)
<223> OTHER INFORMATION: Xaa is D-Pro

<400> SEQUENCE: 69

Ile Xaa Xaa Trp Xaa Thr
1               5

<210> SEQ ID NO 70
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
```

```
<222> LOCATION: (3)..(3)
<223> OTHER INFORMATION: Xaa is Orn(Ar4)
<220> FEATURE:
<221> NAME/KEY: Misc_feature
<222> LOCATION: (5)..(5)
<223> OTHER INFORMATION: Xaa is D-Pro

<400> SEQUENCE: 70

Ile Xaa Xaa Trp Xaa Thr
1               5

<210> SEQ ID NO 71
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (3)..(3)
<223> OTHER INFORMATION: Xaa is Orn(A56)
<220> FEATURE:
<221> NAME/KEY: Misc_feature
<222> LOCATION: (5)..(5)
<223> OTHER INFORMATION: Xaa is D-Pro

<400> SEQUENCE: 71

Ile Xaa Xaa Trp Xaa Thr
1               5

<210> SEQ ID NO 72
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Arg
<220> FEATURE:
<221> NAME/KEY: Misc_feature
<222> LOCATION: (4)..(4)
<223> OTHER INFORMATION: Xaa is Phe(4CF3)
<220> FEATURE:
<221> NAME/KEY: Misc_feature
<222> LOCATION: (5)..(5)
<223> OTHER INFORMATION: Xaa is D-Pro

<400> SEQUENCE: 72

Ile Xaa Arg Xaa Xaa Thr
1               5

<210> SEQ ID NO 73
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
```

```
<223> OTHER INFORMATION: Xaa is Orn(A56)
<220> FEATURE:
<221> NAME/KEY: Misc_feature
<222> LOCATION: (5)..(5)
<223> OTHER INFORMATION: Xaa is D-Pip
<220> FEATURE:
<221> NAME/KEY: Misc_feature
<222> LOCATION: (6)..(6)
<223> OTHER INFORMATION: Xaa is Pro((3S)OH)

<400> SEQUENCE: 73

Trp Xaa Trp Xaa Xaa Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Ala(1Pyraz)
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 74

Xaa Xaa Trp Arg Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Ala(Tet)
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 75

Xaa Xaa Trp Arg Xaa Xaa
1               5

<210> SEQ ID NO 76
<211> LENGTH: 6
<212> TYPE: PRT
```

```
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Orn(Ar2)
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 76

Xaa Xaa Trp Arg Xaa Xaa
1               5

<210> SEQ ID NO 77
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (1)..(1)
<223> OTHER INFORMATION: Xaa is Orn(A56)
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 77

Xaa Xaa Trp Arg Xaa Xaa
1               5

<210> SEQ ID NO 78
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is Orn(Ar7)
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
```

```
<223> OTHER INFORMATION: Xaa is Tic

<400> SEQUENCE: 78

Trp Xaa Trp Xaa Xaa Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is Orn(A56)
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tiq

<400> SEQUENCE: 79

Trp Xaa Trp Xaa Xaa Xaa
1               5

<210> SEQ ID NO 80
<211> LENGTH: 6
<212> TYPE: PRT
<213> ORGANISM: Artificial Sequence
<220> FEATURE:
<223> OTHER INFORMATION: template fixed peptidomimetics with CXCR7
      modulating activity
<220> FEATURE:
<221> NAME/KEY: Misc_feature
<222> LOCATION: (2)..(2)
<223> OTHER INFORMATION: Xaa is D-Phe
<220> FEATURE:
<221> NAME/KEY: Misc_feature
<222> LOCATION: (4)..(4)
<223> OTHER INFORMATION: Xaa is Orn(A56)
<220> FEATURE:
<221> NAME/KEY: Misc_feature
<222> LOCATION: (5)..(5)
<223> OTHER INFORMATION: Xaa is D-Pro((4R)NH2)
<220> FEATURE:
<221> NAME/KEY: Misc_feature
<222> LOCATION: (6)..(6)
<223> OTHER INFORMATION: Xaa is Tic

<400> SEQUENCE: 80

Trp Xaa Trp Xaa Xaa Xaa
1               5
```

TEMPLATE-FIXED PEPTIDOMIMETICS WITH CXCR7 MODULATING ACTIVITY

The present invention provides novel peptidomimetics incorporating a chain of α-amino acid residues as defined below attached to a template which provides specific structural constrains for a β-hairpin like conformation. These template-fixed β-hairpin mimetics have a selective modulating activity on the CXCR7 receptor and are thus useful in the treatment of a variety of diseases and disorders mediated by or sustained through the activity of CXCR7 or in the support of therapeutic treatments of specific disease conditions of primarily different cause. The present invention relates to methods of using these compounds in the treatment of the various diseases and disorders, to pharmaceutical compositions and forms comprising these compounds and efficient processes for the preparation and production of these compounds and their intermediates.

Many medically relevant biological processes are mediated by signal transduction that involves chemokines and their receptors, for instance the tissue specific recruitment of leukocytes to sites of inflammation. As for other ligand/receptor pairs of their super family, the GPCRs, for some receptors the full scope of downstream activity and sometimes organ specific function still remains not fully understood. One of this recently deorphanized GPCRs is the chemokine receptor CXCR7 (RDC1), which binds with high affinity the inflammatory and homing chemokines CXCL11 (ITAC) and CXCL12 (SDF-1) (K. Balabanian, B. Lagane et al., *J. Biol. Chem.* 2005, 280, 35760-35766).

CXCL12 also binds to another chemokine receptor, CXCR4, and the CXCL12/CXCR4 axis has been demonstrated to play a crucial role in different inflammatory and cancer diseases. The recent finding that CXCL12 binds to both CXCR4 and CXCR7 indicates that the physiological and pathological functions of CXCL12 might be mediated by two distinct receptors (C. Dambly-Chaudière et al., *BMC Dev. Biol.* 2007, 7-23).

In contrast to CXCR4, CXCR7 does not induce typical chemokine responses such as calcium mobilization. Instead, recent findings indicate that the receptor has a key function in the generation of a CXCL12 local gradient for CXCR4-dependent migration by scavenging CXCL12. These observations seem to be in favor of a main role of CXCR7 as a decoy receptor ("CXCL12 sink") with the critical function of clearing excess CXCL12 by internalization (B. Boldajipour, H. Mahabaleshwar et al., *Cell* 2008, 132, 463-73; Cell Adh. Migr. 2008, 2, 69-70). Moreover, it has been shown that CXCR7 can modulate CXCR4 activity by forming heterodimers and that it may activate other intracellular signaling pathways (A. Levoye, K. Balabanian et al., *Blood* 2009, 113, 6085-93).

As a consequence of the close functional relation between the two receptors, CXCR7 may be involved in the same disease conditions in which CXCR4 has been shown to play an important role. In particular, CXCR7 is markedly expressed in a variety of tumors and their respective tumor cell lines (e.g. prostate, bladder, breast cancer, multiple myeloma, rhabdomyosarcoma, non-small cell lung cancer); its expression level is often correlated with tumor growth and, moreover, with invasiveness. Two major mechanisms have been suggested for the role of CXCR7 in tumor development and metastasis: 1) increase of cancer cell proliferation and survival, which may be supported by a pro-angiogenic effect; 2) CXCR7 favors adhesion and transendothelial migration of cancer cells together with CXCR4-mediated migration.

Moreover, recent studies suggest that CXCR7 may also be implicated in rheumatoid arthritis, other chronic and/or autoimmune inflammatory diseases (G. Graham et al., *Curr. Mol. Med.* 2009, 9 (2), 86-93) or pulmonary arterial hypertension since it is up-regulated in certain specific tissues, such as in lungs under hypoxic conditions (C. M. Costello, P. McLoughlin et al., *Am. J. Physiol. Lung Cell Mol. Physiol.* 2008, 295 (2), 272-284).

Now the present invention provides new chemical entities for a potential use as potent, selective and drugable ligands for the GPC-receptor CXCR7. In the compounds described below, a special strategy is utilized to stabilize β-hairpin conformations in backbone-cyclic β-hairpin mimetics exhibiting selective activity against the CXCR7 receptor. This involves transplanting a loop sequence of a natural or unnatural biopolymer onto a template, whose function is to restrain the peptide loop backbone into a β-hairpin geometry.

Template-bound hairpin mimetic peptides have been described in the literature (D. Obrecht, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods have now been established (L. Jiang, K. Moehle, B. Dhanapal, D. Obrecht, J. A. Robinson, *Helv. Chim. Acta.* 2000, 83, 3097-3112). These methods allow the synthesis and screening of large hairpin mimetic libraries, which in turn considerably facilitates structure-activity studies, and hence the discovery of new molecules with potent and, especially, selective agonizing or antagonizing activity.

There are few studies in the field describing tetrameric peptides linked to a template as agonist and/or antagonists of GPCRs in general (e.g. WO2008092281). The present invention is now providing novel compounds, which differ significantly in structure and exhibit a high biological activity and surprising selectivity for a specific novel receptor in this field, namely, for the CXCR7 receptor.

The present invention relates to novel β-hairpin peptidomimetics of the general formula (I)

wherein the single elements T or P are connected in either direction from the carbonyl (C=O) point of attachment to the nitrogen (N) of the next element and wherein either T¹ is an α-amino acid residue of one of the formulae

AA1

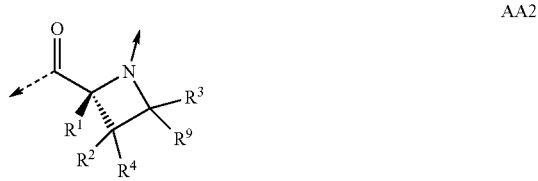

AA2

-continued
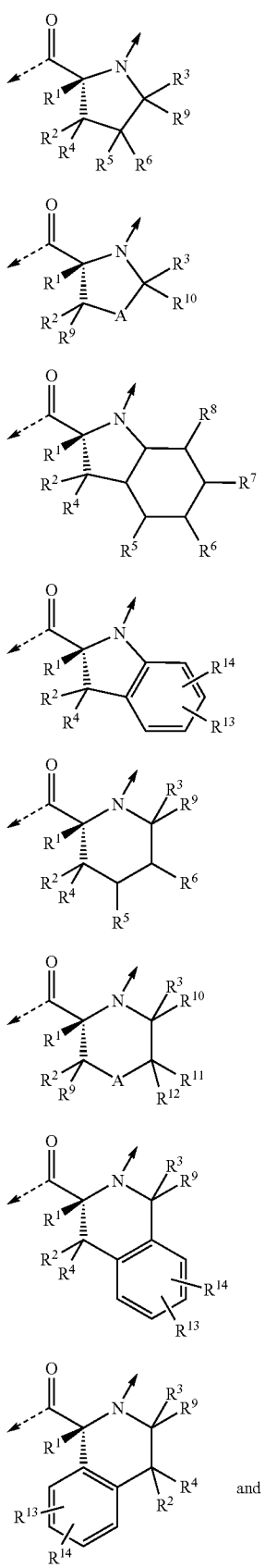
$T^2$ is an α-amino acid residue of one of the formulae
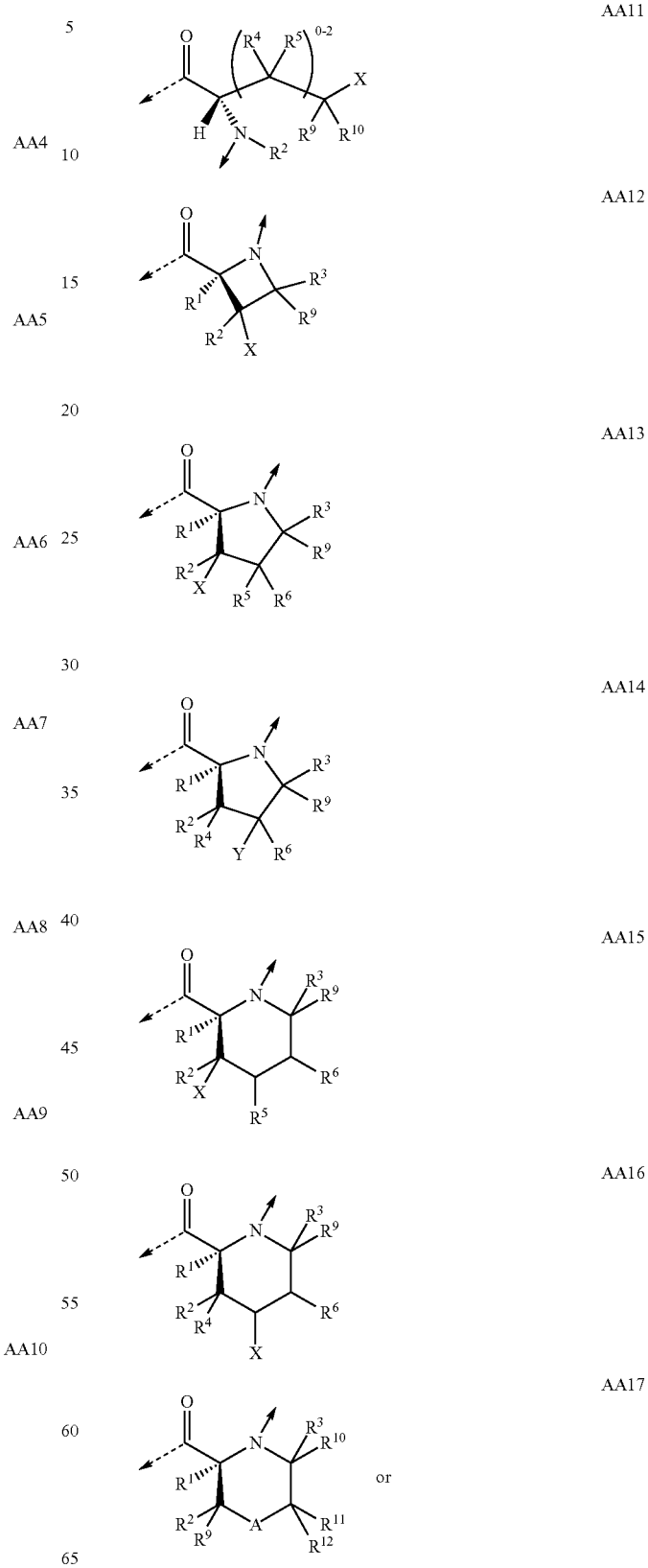

$T^1$ is an α-amino acid residue of one of the formulae
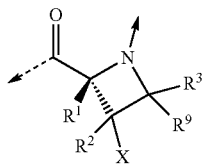
AA18
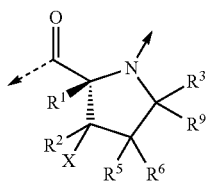
AA19
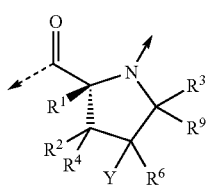
AA20
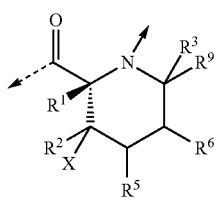
AA21
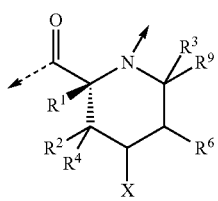
AA22
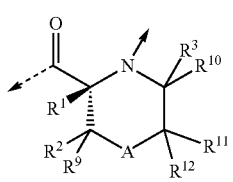
AA23 and
$T^2$ is an α-amino acid residue of one of the formulae AA11 to AA17, hereinabove, or an α-amino acid residue of one of the formulae
AA24
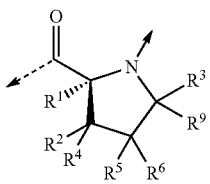
AA25
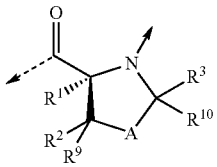
AA26
AA27
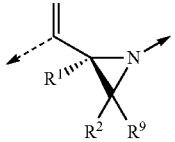
AA28
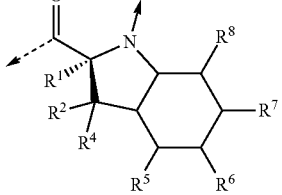
AA29
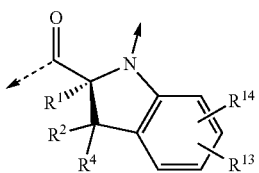
AA30
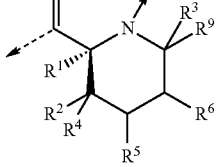
AA31
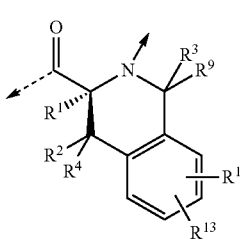
AA32
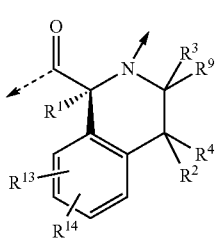

P¹, P³ and P⁴ are independently
—NR¹CH(R²⁹)CO—; —NR¹CH(R³⁰)CO—; or
—NR¹CH(R³¹)CO—;
P² is an α-amino acid residue of one of the formulae

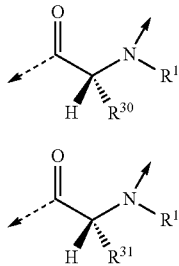

AA33

AA34

A is O; NR¹⁷; S; SO; or SO₂;
X is OH; NH₂; OR¹⁶; NR¹R¹⁶; or NR¹⁷R¹⁸;
Y is NH₂; F; OR¹⁶; NR¹R¹⁶; or NR¹⁷R¹⁸;
R¹, R² and R³ are independently
  H; CF₃; lower alkyl; lower alkenyl; aryl-lower alkyl; or heteroaryl-lower alkyl;
R⁴, R⁵, R⁶, R⁷ and R⁸ are independently H; F; CF₃; lower alkyl; lower alkenyl; cycloalkyl; heterocycloalkyl; aryl; heteroaryl; aryl-lower alkyl; heteroaryl-lower alkyl; —(CHR¹⁵)ₒOR¹⁷; —(CHR¹⁵)ₒSR¹⁷; —(CHR¹⁵)ₒNR¹⁷R¹⁸; —(CHR¹⁵)ₒOCONR¹⁷R¹⁸; —(CHR¹⁵)ₒNR¹CONR¹⁷R¹⁸; —(CHR¹⁵)ₒNR¹COR¹⁷; —(CHR¹⁵)ₒCOOR¹⁷; —(CHR¹⁵)ₒCONR¹⁷R¹⁸; —(CHR¹⁵)ₒPO(OR¹)₂; —(CHR¹⁵)ₒSO₂R¹⁷; —(CHR¹⁵)ₒNR¹SO₂R¹⁷; —(CHR¹⁵)ₒSO₂NR¹⁷R¹⁸; —(CR¹R¹⁵)ₒR³⁵; or —(CHR¹)ₙ—O—(CHR²)ₘR³⁵; or
R⁴ and R² taken together can form
  =O; —(CHR¹⁵)ₚ—; —(CH₂)ₙ—O—(CH₂)ₘ—; —(CH₂)ₙS(CH₂)ₘ—; or —(CH₂)ₙNR¹(CH₂)ₘ—; or
R⁴ and R⁵; R⁵ and R⁶; R⁶ and R⁷; R⁷ and R⁸; or R⁶ and R⁹ taken together can form:
  —(CHR¹⁵)ₚ—; —(CH₂)ₙ—O—(CH₂)ₘ—; —(CH₂)ₙS(CH₂)ₘ—; or —(CH₂)ₙNR¹(CH₂)ₘ—; or
R⁴ and R⁵ are independently X;
R⁹, R¹⁰, R¹¹ and R¹² are independently
  H; F; CF₃; lower alkyl; lower alkenyl; cycloalkyl; heterocycloalkyl; aryl; heteroaryl; aryl-lower alkyl; heteroaryl-lower alkyl; —(CHR¹⁵)ᵣOR¹⁷; —(CHR¹⁵)ᵣSR¹⁷; —(CHR¹⁵)ᵣNR¹⁷R¹⁸; —(CHR¹⁵)ᵣOCONR¹⁷R¹⁸; —(CHR¹⁵)ᵣNR¹CONR¹⁷R¹⁸; —(CHR¹⁵)ᵣNR¹COR¹⁷; —(CHR¹⁵)ₒCOOR¹⁷; —(CHR¹⁵)ₒCONR¹⁷R¹⁸; —(CHR¹⁵)ᵣPO(OR¹)₂; —(CHR¹⁵)ₒSO₂R¹⁷; —(CHR¹⁵)ᵣNR¹SO₂R¹⁷; —(CHR¹⁵)ᵣSO₂NR¹⁷R¹⁸; —(CR¹R¹⁵)ₒR³⁵; or —(CHR¹)ᵣO(CHR¹)ₒR³⁵; or
R¹¹ and R¹² taken together can form
  =O; or =NR¹;
R¹³ and R¹⁴ are independently
  H; F; Cl; Br; CF₃; OCF₃; OCHF₂; CN; NO₂; lower alkyl; lower alkenyl; aryl; heteroaryl; aryl-lower alkyl; heteroaryl-lower alkyl; —(CHR¹⁵)ₒOR¹⁷; —(CHR¹⁵)ₒSR¹⁷; —(CHR¹⁵)ₒNR¹⁷R¹⁸; —(CHR¹⁵)ₒOCONR¹⁷R¹⁸; —(CHR¹⁵)ₒNR¹CONR¹⁷R¹⁸; —(CHR¹⁵)ₒNR¹COR¹⁷; —(CHR¹⁵)ₒCOOR¹⁷; —(CHR¹⁵)ₒCONR¹⁷R¹⁸; —(CHR¹⁵)ₒPO(OR¹)₂; —(CHR¹⁵)ₒSO₂R¹⁷; —(CHR¹⁵)ₒNR¹SO₂R¹⁷; —(CHR¹⁵)ₒSO₂NR¹⁷R¹⁸; —(CR¹R¹⁵)ₒR³⁵; or —(CHR¹)ᵣO(CHR¹)ₒR³⁵;

R¹⁵ is H; F; CF₃; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; —(CHR¹)ₒOR¹⁷; —(CHR¹)ₒSR¹⁷; —(CHR¹)ₒNR¹⁷R¹⁸; —(CHR¹)ₒNR²⁰C(=NR¹⁹)NR¹⁷R¹⁸; —(CHR¹)ₒCOOR¹⁷; —(CHR¹)ₒNR¹⁷R¹⁸; —(CHR¹)ₒSO₂R¹⁷; or —(CHR¹)ₒSO₂NR¹⁷R¹⁸;

R¹⁶ is CF₃; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR¹)ₛOR¹⁷; —(CHR¹)ₛSR¹⁷; —(CHR¹)ₛNR¹⁷R¹⁸; —(CHR¹)ₒCOR¹⁷; —(CHR¹)ₒCOOR¹⁷; —(CHR¹)ₒCONR¹⁷R¹⁸; or —(CHR¹)ₒSO₂R¹⁷;

R¹⁷, R¹⁸, R¹⁹ and R²⁰ are independently
  H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements —NR¹⁷R¹⁸ and —NR¹⁹R²⁰ can independently form:
  heterocycloalkyl; aryl-heterocycloalkyl; or heteroaryl-heterocycloalkyl;
  or a group of one of the formulae

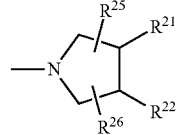

C1

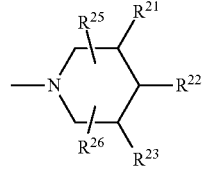

C2

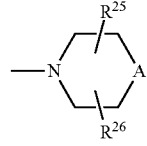

C3

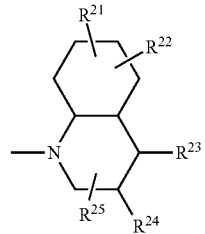

C4

-continued

C5

[structure: bicyclic piperidine-cyclohexane with R21, R22, R23, R25]

C6

[structure: fused heterocycle with Z, Z', R27, R21, R25]

C7

[structure: fused heterocycle with Z, Z', R27, R21, R22, R25]

C8

[structure: fused heterocycle with Z, Z', R27, A, R25]

Z, Z' and Z" are independently
—CR39; or N;

R21, R22, R23 and R24 are independently
H; F; CF3; lower alkyl; lower alkenyl; cycloalkyl; heterocycloalkyl; aryl; heteroaryl; aryl-lower alkyl; heteroaryl-lower alkyl; —(CHR1)$_o$OR17; —(CHR1)$_o$SR17; —(CHR1)$_o$NR2R17; —(CHR1)$_o$OCONR2R17; —(CHR1)$_o$NR2CONR3R17; —(CHR1)$_o$NR2COR17; —(CHR1)$_o$COOR17; —(CHR1)$_o$CONR2R17; —(CHR1)$_o$PO(OR2)$_2$; —(CHR1)$_o$SO2R17; —(CHR1)$_o$NR2SO2R17; —(CHR1)$_o$SO2NR2R17; —(CR1R2)$_o$R38; or —(CHR1)$_n$O(CHR2)$_m$R38;

R25 and R26 are independently
H; F; CF3; lower alkyl; lower alkenyl; cycloalkyl; heterocycloalkyl; aryl; heteroaryl; aryl-lower alkyl; heteroaryl-lower alkyl; —(CHR1)$_r$OR17; —(CHR1)$_r$SR17; —(CHR1)$_r$NR2R17; —(CHR1)$_r$OCONR2R17; —(CHR1)$_r$NR2CONR3R17; —(CHR1)$_r$NR2COR17; —(CHR1)$_o$COOR17; —(CHR1)$_o$CONR2R17; —(CHR1)$_r$PO(OR2)$_2$; —(CHR1)$_r$SO2R17; —(CHR1)$_r$NR2SO2R17; —(CHR1)$_r$SO2NR2R17; —(CR1R2)$_o$R38; or —(CHR1)$_r$O(CHR2)$_o$R38;

R27 is H; F; Cl; Br; CF3; OCHF2; CN; NO2; lower alkyl; lower alkenyl; aryl; heteroaryl; aryl-lower alkyl; heteroaryl-lower alkyl; —(CHR1)$_o$OR17; —(CHR1)$_o$SR17; —(CHR1)$_o$NR2R17; —(CHR1)$_o$OCONR2R17; —(CHR1)$_o$NR2CONR3R17; —(CHR1)$_o$NR2COR17; —(CHR1)$_o$COOR17; —(CHR1)$_o$CONR2R17; —(CHR1)$_o$PO(OR2)$_2$; —(CHR1)$_o$SO2R17; —(CHR1)$_o$NR2SO2R17; —(CHR1)$_o$SO2NR2R17; —(CR1R2)$_o$R38; or —(CHR1)$_r$O(CHR2)$_o$R38;

R29 is H; alkyl; alkenyl; cycloalkyl-lower alkyl; heterocycloalkyl-lower alkyl; —(CHR4)$_n$OR17; —(CHR4)$_n$SR17; or —(CHR4)$_n$NR17R18;

R30 is —(CR1R4)$_n$R35; —(CH2)$_n$O(CH2)$_m$R35; —(CH2)$_n$S(CH2)$_m$R35; or —(CH2)$_n$NR1(CH2)$_m$R35;

R31 is alkyl; alkenyl; —(CR1R15)$_q$NR17R18; —(CR1R15)$_q$NR2R16; —(CR1R15)$_q$NR17R32; —(CR1R15)$_q$NR17COR18; —(CH2)$_q$C(=NR15)NR17R18; —(CH2)$_q$C(=NOR19)NR17R18; —(CH2)$_q$C(=NNR17R18)NR19R20; —(CR1R15)$_q$NR20C(=NR19)NR17R18; —(CR1R15)$_q$=C(NR17R18)NR19R20; —(CR1R15)$_q$OR17; —(CR1R15)$_q$OR32; —(CR1R15)$_q$SR17; —(CR1R15)$_q$SO2R17; —(CR1R15)$_q$NR17SO2R18; —(CR1R15)$_q$SO2NR2R16; —(CR1R15)$_q$SO2NR17R18; —(CR1R15)$_q$NR19SO2NR17R18; —(CR1R15)$_q$PO(OR2)$_2$; —(CH2)$_n$O(CH2)$_m$NR17R18; —(CH2)$_n$O(CH2)$_m$C(=NR19)NR17R18; —(CH2)$_n$O(CH2)$_m$C(=NOR19)NR17R18; —(CH2)$_n$O(CH2)$_m$C(=NNR17R18)NR19R20; —(CH2)$_n$O(CH2)$_m$NR20C(=NR19)NR17R18; —(CH2)$_n$O(CH2)$_m$N=C(NR17R18)NR19R20; —(CH2)$_n$S(CH2)$_m$NR17R18; —(CH2)$_n$S(CH2)$_m$C(=NR19)NR17R18; —(CH2)$_n$S(CH2)$_m$C(=NOR19)NR17R18; —(CH2)$_n$S(CH2)$_m$C(=NNR17R18)NR19R20; —(CH2)$_n$S(CH2)$_m$NR20C(=NR19)NR17R18; —(CH2)$_n$S(CH2)$_m$N=C(NR17R18)NR19R20; —(CR1R15)$_q$COOR17; —(CR1R15)$_q$CONR17R18; or —(CR1R15)$_q$COR33;

R32 is —COR29; —COR30; —CO(CR1R15)$_o$R17; —CO(CR1R15)$_o$OR17; —CO(CR1R15)$_o$NR17R18; —CO(CR1R15)$_o$NR2R16; —CO(CR1R29)NR17R18; —CO(CR1R30)NR17R18; —CO(CR1R34)NR17R18; —CO(CHR1)$_o$CONR17R18; —CO(CHR1)$_o$CONR17SO2R18; —CO(CR1R15)$_o$NR17SO2R18; —CONR1(CHR17)$_n$NR2(CHR15)$_m$R16; —CO(CHR17)$_n$O(CHR15)$_m$R16; —CONR1(CHR17)$_n$O(CHR15)$_m$R16; —SO2R29; —SO2R30; —SO2(CR1R15)$_o$R17; or —SO2(CR1R15)$_o$NR17R18;

R33 is —NR1C(R2)(R29)COOR17; —NR1C(R2)(R29)CONR17R18; —NR1C(R2)(R30)COOR17; —NR1C(R2)(R30)CONR17R18; —NR1C(R2)(R34)COOR17; or —NR1C(R2)(R34)CONR17R18;

R34 is —(CR1R15)$_q$NR17R18; —(CH2)$_q$C(=NR19)NR17R18; —(CH2)$_q$C(=NOR19)NR17R18; —(CH2)$_q$C(=NNR17R18)NR19R20; —(CR1R15)$_q$NR2C(=NR19)NR17R18; —(CR1R15)$_q$N=C(NR17R18)NR19R20; —(CR1R15)$_q$OR17; —(CR1R15)$_q$SR17; —(CR1R15)$_q$SO2R17; —(CR1R15)$_q$NR17SO2R18; —(CR1R15)$_q$SO2NR1R16; —(CR1R15)$_q$SO2NR17R18; —(CR1R15)$_q$NR2SO2NR17R18; —(CR1R15)$_q$PO(OR1)$_2$; —(CH2)$_n$O(CH2)$_m$NR17R18; —(CH2)$_n$O(CH2)$_m$C(=NR19)NR17R18; —(CH2)$_n$O(CH2)$_m$C(=NOR19)NR17R18; —(CH2)$_n$O(CH2)$_m$C(=NNR17R18)NR19R20; —(CH2)$_n$O(CH2)$_m$NR20C(=NR19)NR17R18; —(CH2)$_n$O(CH2)$_m$N=C(NR17R18)NR19R20; —(CH2)$_n$S(CH2)$_m$NR17R18; —(CH2)$_n$S(CH2)$_m$C(=NR19)NR17R18; —(CH2)$_n$S(CH2)$_m$C(=NOR19)NR17R18; —(CH2)$_n$S(CH2)$_m$C(=NNR17R18)NR19R20; —(CH2)$_n$S(CH2)$_m$NR20C(=NR19)NR17R18; —(CH2)$_n$S(CH2)$_m$N=C(NR17R18)NR19R20; —(CR1R15)$_q$COOR17; or —(CR1R15)$_q$CONR17R18;

$R^{35}$ is an aryl group of one of the formulae
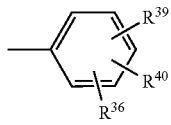 AR1
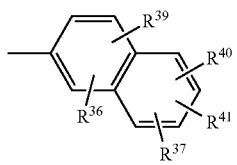 AR2
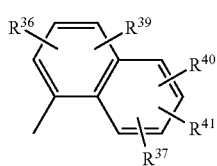 AR3
or a heteroaryl group of one of the formulae
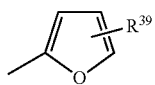 H1
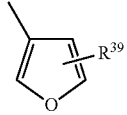 H2
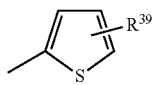 H3
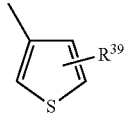 H4
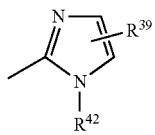 H5
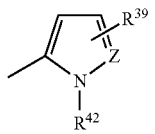 H6
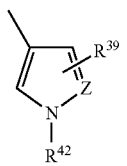 H7
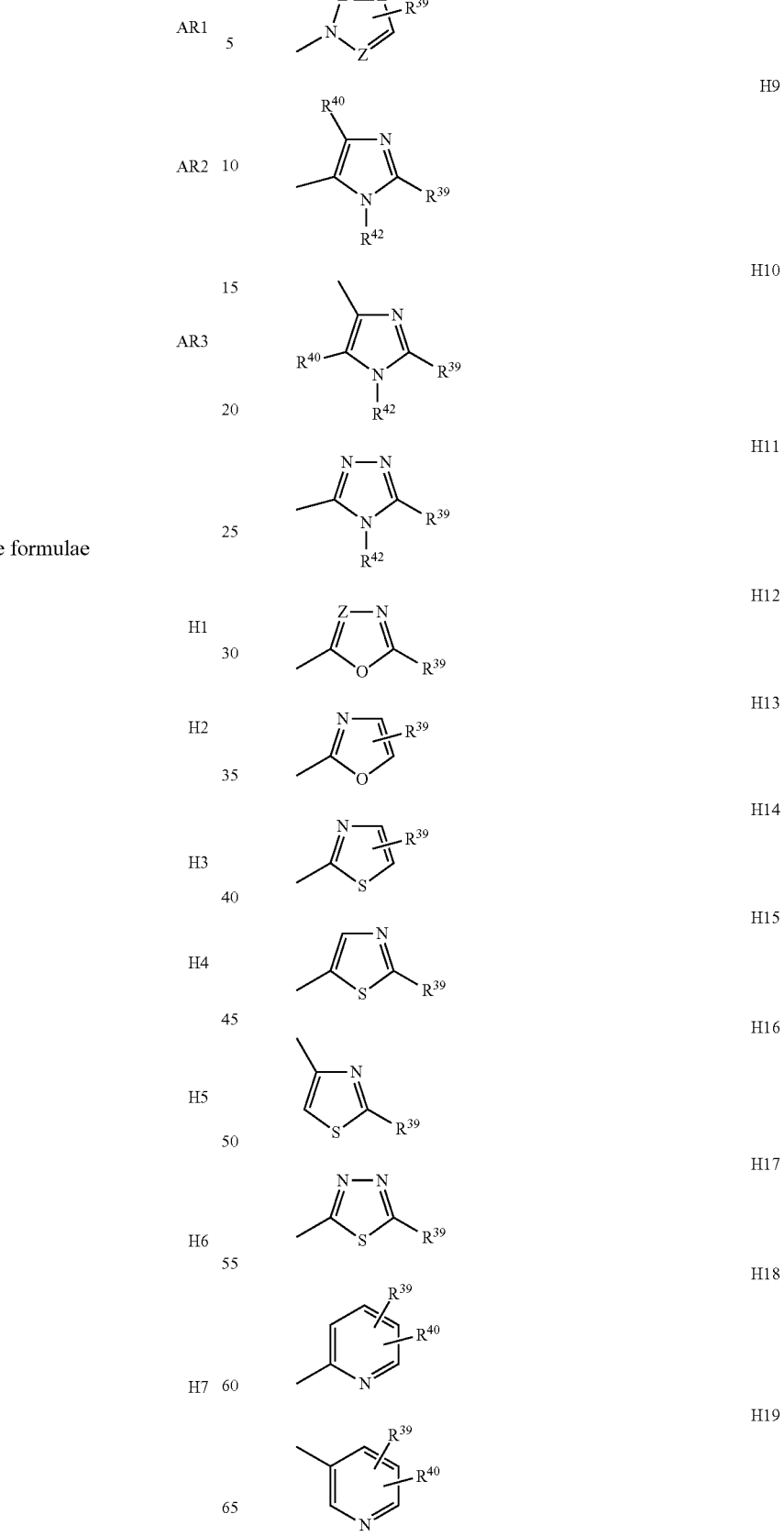

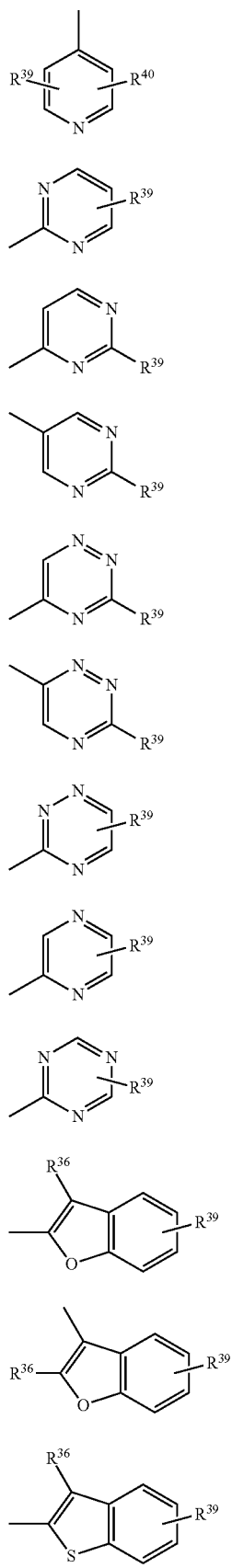
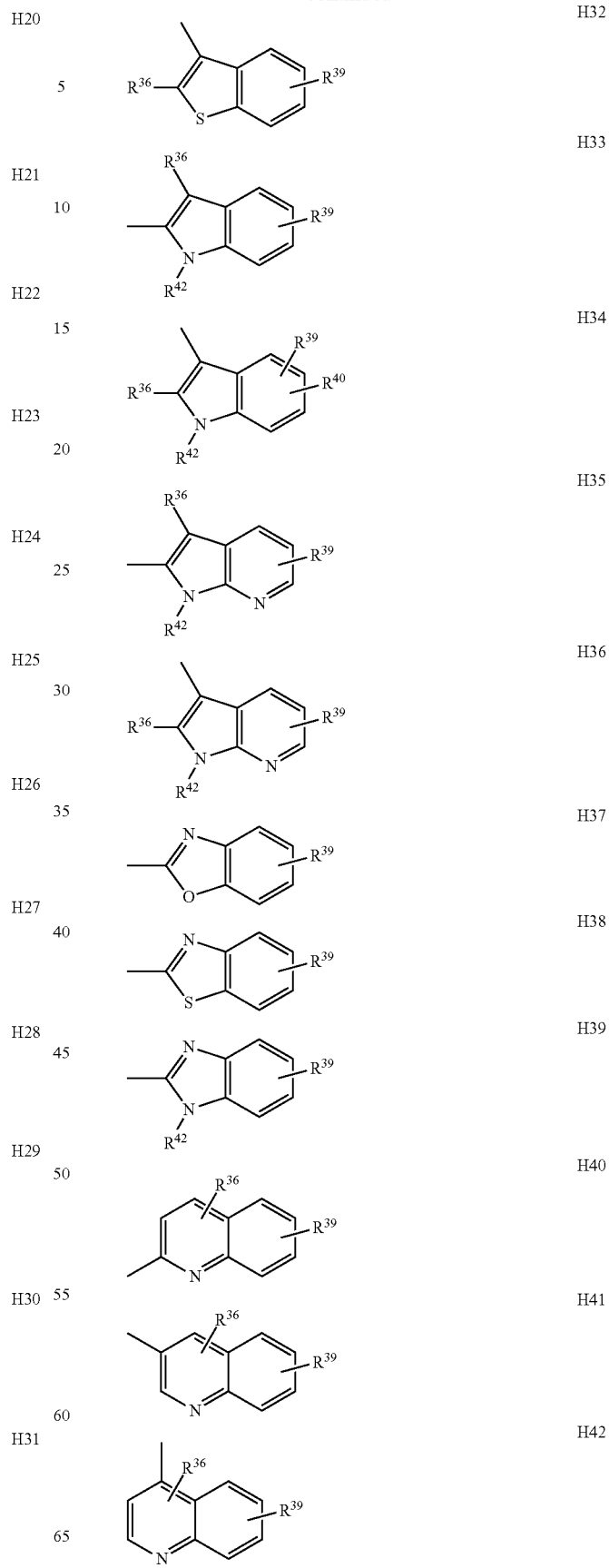

-continued

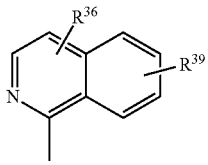
H43

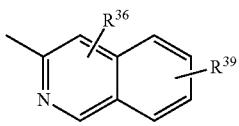
H44

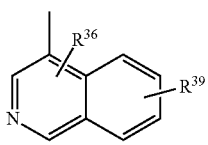
H45

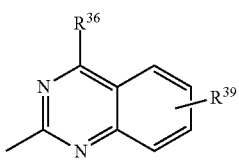
H46

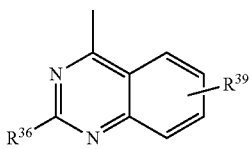
H47

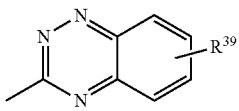
H48

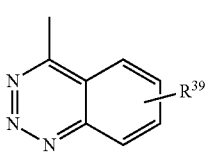
H49

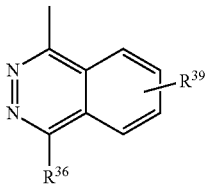
H50

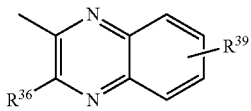
H51

$R^{36}$ and $R^{37}$ are independently

H; F; Cl; Br; CF$_3$; OCF$_3$; OCHF$_2$; CN; NO$_2$; lower alkyl; lower alkenyl; aryl; heteroaryl; aryl-lower alkyl; heteroaryl-lower alkyl; —(CH$_2$)$_o$R$^{38}$; —(CH$_2$)$_o$OR$^{17}$; —O(CH$_2$)$_o$R$^{38}$; —(CH$_2$)$_o$SR$^{17}$; —(CH$_2$)$_o$NR$^{17}$R$^{18}$; —(CH$_2$)$_o$OCONR$^{17}$R$^{18}$; —(CH$_2$)$_o$NR$^1$CONR$^{17}$R$^{18}$; —(CH$_2$)$_o$NR$^1$COR$^{17}$; —(CH$_2$)$_o$COOR$^{17}$; —(CH$_2$)$_o$CONR$^{17}$R$^{18}$; —(CH$_2$)$_o$PO(OR$^1$)$_2$; —(CH$_2$)$_o$SO$_2$R$^{16}$; or —(CH$_2$)$_o$COR$^{17}$;

$R^{38}$ is an aryl group of the formula

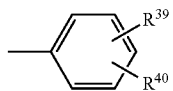
AR4

$R^{39}$, $R^{40}$ and $R^{41}$ are independently
H; F; Cl; Br; OH; NH$_2$; NO$_2$; CN; CF$_3$; OCHF$_2$; OCF$_3$; —NR$^1$R$^{17}$; —(CH$_2$)$_o$COOR$^{17}$; —(CH$_2$)$_o$CONR$^1$R$^{17}$; lower alkyl; lower alkoxy; or lower alkenyl;

$R^{42}$ is H; lower alkyl; or aryl-lower alkyl;

n and m are independently an integer of 0-5 with the proviso that n+m≤6;

o is 0-4; p is 2-6; q is 1-6; r is 1-3; s is 0-4 and pharmaceutically acceptable salts thereof.

Each single group "R$^x$" with the same index-number x for x=1-42 in a specific formula is independently selected and therefore these groups are the same or different.

As used in this description, the term "alkyl", taken alone or in combinations (i.e. as part of another group, such as "arylalkyl") designates saturated, straight-chain or branched hydrocarbon radicals having up to 12, preferably up to 8, carbon atoms and may be optionally substituted. In accordance with a preferred embodiment of the present invention "alkyl" is "lower alkyl" which designated alkyl groups having up to 6 carbon atoms.

The term "alkenyl", taken alone or in combinations, designates straight chain or branched hydrocarbon radicals having up to 12, preferably up to 8, carbon atoms and containing at least one or, depending on the chain length, up to four olefinic double bonds. Such alkenyl moieties are optionally substituted and can exist as E or Z configurations, both of which are part of the invention.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbonyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4]nonane and the like. Said heterocycloalkyl ring(s) may be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, CF$_3$, OCF$_3$, OCHF$_2$, N(CH$_3$)$_2$, NO$_2$, lower alkyl, lower alkenyl, phenyl or phenoxy.

The term "heteroaryl", taken alone or in combinations, designates aromatic heterocyclic radicals containing one or two five- and/or six-membered rings, at least one of them containing up to four heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "arylalkyl", as used herein, refers to an alkyl group as defined above, substituted by an aryl group, as defined above. Examples of arylalkyl moieties include, but are not limited to, benzyl, 1-phenylethyl, 2-phenylethyl, 3-phenylpropyl, 2-phenylpropyl and the like. Similarly, the term "aryl-lower alkyl", refers to the above moiety but wherein the alkyl group is a "lower alkyl" group.

The term "heteroarylalkyl", as used herein, refers to an alkyl group as defined above, substituted by a heteroaryl group, as defined above. Analogously the term "heteroaryl-lower alkyl", refers to the above moiety but wherein the alkyl group is a "lower alkyl" group.

The term "aryl-cycloalkyl", as used herein, refers to a cycloalkyl group as defined above, substituted or annelated by an aryl group, as defined above. Examples of aryl-cycloalkyl moieties include, but are not limited to, phenylcyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydro-quinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analogously to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "alkoxy" and "aryloxy", taken alone or in combinations, refer to the groups of —O-alkyl and —O-aryl respectively, wherein an alkyl group or an aryl group is as defined above.

The term "optionally substituted" is intended to mean that a group, such as but not limited to alkyl, alkenyl, cycloalkyl, aryl, heteroaryl, heterocycloalkyl, alkoxy and aryl-oxy may be substituted with one or more substituents independently selected from but not limited to, e.g., amino (—$NH_2$), dimethylamino, nitro (—$NO_2$), halogen (F, Cl, Br, I), $CF_3$, cyano (—CN), hydroxy, methoxy, oxo (=O), carboxy, phenyl, phenyloxy, benzyl, sulfonic acid, sulfate, phosphonic acid, phosphate, or phosphonate etc.

The term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, s-butyl, isobutyl, t-butyl, and the like.

The peptidomimetics of the present invention can also be diastereomers (e.g. epimers) of the compounds of formula (I) based on chiral centers where the absolute stereochemistry is not explicitly defined in the above description. These stereoisomers can be prepared by a modification of the process described below in which epimers or enantiomers of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2H$ (D), $^3H$, $^{11}C$, $^{14}C$, $^{127}I$ etc. These isotopic analogs and their pharmaceutical salts and formulations are considered useful agents in the therapy and/or diagnostic, for example, but not limited to, where a fine-tuning of in vivo half-life time could lead to an optimized dosage regimen.

A particular embodiment of the invention relates to derivatives of general formula (I), wherein specifically $R^{16}$ is $CF_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; —$(CHR^1)_sOR^{17}$; —$(CHR^1)_sSR^{17}$; —$(CHR^1)_sNR^{17}R^{18}$; —$(CHR^1)_oCOR^{17}$; —$(CHR^1)_oCOOR^{17}$; —$(CHR^1)_oCONR^{17}R^{18}$; or —$(CHR^1)_oSO_2R^{17}$;

$R^{17}$, $R^{18}$, $R^{19}$ and $R^{20}$ are independently
  H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; or heteroaryl-lower alkyl; or the structural elements —$NR^{17}R^{18}$ and —$NR^{19}R^{20}$ can independently form:
  heterocycloalkyl; aryl-heterocycloalkyl; or heteroaryl-heterocycloalkyl; or a group of one of the above formulae C1 to C8;

$R^{31}$ is alkyl; alkenyl; —$(CR^1R^{15})_qNR^{17}R^{18}$; —$(CR^1R^{15})_qNR^2R^{16}$; —$(CR^1R^{15})_qNR^{17}COR^{18}$; —$(CH_2)_qC(=NR^{15})NR^{17}R^{18}$; —$(CR^1R^{15})_qNR^{20}C(=NR^{19})NR^{17}R^{18}$; —$(CR^1R^{15})_qOR^{17}$; —$(CR^1R^{15})_qSR^{17}$; —$(CR^1R^{15})_qSO_2R^{17}$; —$(CR^1R^{15})_qNR^{17}SO_2R^{18}$; —$(CR^1R^{15})_qSO_2NR^2R^{16}$; —$(CR^1R^{15})_qSO_2NR^{17}R^{18}$; —$(CH_2)_nO(CH_2)_mNR^{17}R^{18}$; —$(CH_2)_nO(CH_2)_mC(=NR^{19})NR^{17}R^{18}$; —$(CH_2)_nO(CH_2)_mNR^{20}C(=NR^{19})NR^{17}R^{18}$; —$(CH_2)_nS(CH_2)_mNR^{17}R^{18}$; —$(CH_2)_nS(CH_2)_m NR^{20}C(=NR^{19})NR^{17}R^{18}$; —$(CR^1R^{15})_qCONR^{17}R^{18}$; or —$(CR^1R^{15})_qCOR^{33}$;

s is 2-4 with all other elements of formula (I) as described above.

In a further particular embodiment of the invention the elements of general formula (I) are defined as follows $T^1$ is $^DPro$; $^DPip$; $^DTic$; $^DTiq$; $^DOic$; $^DAzt$; $^DPro((3R)OH)$; $^DPro((3S)OH)$; $^DPro((3R)NH_2)$; $^DPro((3S)NH_2)$; $^DPro((4R)OH)$; $^DPro((4S)OH)$; $^DPro((4R)NH_2)$; $^DPro((4S)NH_2)$; $^DPro((4S)NHBz)$; or $^DMor$;

$T^2$ is Thr; alloThr; Ser; hSer; Pro((3R)OH); Pro((3S)OH); Hyp(Bn); (4S)-Hyp(Bn); Pro((3R)NH_2); Pro((3S)NH_2); Pro((4R)NH_2); Pro((4S)NH_2); Pro((4S)F); Pro((4S)NHBz); or Mor; or when $T^1$ is $^DPro((3R)OH)$; $^DPro((3S)OH)$; $^DPro((3R)NH_2)$; $^DPro((3S)NH_2)$; $^DPro((4R)NH_2)$; $^DPro((4S)NH_2)$; $^DPro((4S)NHBz)$; or $^DMor$ then $T^2$ can in addition be
  Pro; Pip; Tic; Tiq; Oic; or Azt;

$P^1$, $P^3$ and $P^4$ are independently
  Ala; Arg; Asn; Asp; Cit; Cys; Glu; Gln; Gly; His; Ile; Leu; Lys; Met; Orn; Phe; Pro; Ser; Thr; Trp; Tyr; Val; Abu; Agb; Agp; Ala(tBu); Ala(cPr); Ala(2Furyl); Ala(3Furyl); Ala(Ppz); Ala(1Pyraz); Ala(2Quin); Ala(3Quin); Ala(4Quin); Ala(Tet); Azt; Bbta; Bip; Cha; Chg; Dab; Dab(Ac); Dab(cPr); Dab(iPr); Dab(4Me_2NPhSO_2); Dab(MeOEtNCO); Dab(MePpzCO); Dab(MeSO_2); Dab(morphCO); Dab(1Nal); Dab(2Nal); Dap; Dap(CONH_2); Dap(MeOEt); Dap((MeOEt)_2); Deg; Gly (tBu); hArg; hCha; hCys; hHis; hLys; hPhe; hSer; hSer (Me); hTrp; hTyr; His(Me); His(Bn); Hyp(Bn); (4S)-Hyp(Bn); Hyp(4BrBn); Hyp(3CNBn); Hyp(4CNBn); Hyp(CONHPh); Hyp(Ph); Lys(Ac); Lys(Bz); Lys(cPr); Lys(iPr); Lys(Me); Lys(Nic); Lys((5R)OH); Lys(4Oxa); Met(O₂); 1Nal; 2Nal; Nle; Nle(6OBn); OctG; Oic; Orn (cPr); Orn(iPr); 2Pal; 3Pal; 4Pal; Phe(2Cl); Phe(3Cl); Phe(4Cl); Phe(3,4Cl₂); Phe(2F); Phe(3F); Phe(4F); Phe (4CN); Phe(4CF₃); Phe(4COOMe); Phg; Pip; Pro((4R) Bn); Pro((4S)F); Pro((4S)cHex); Pro(5,5Me₂); Ser(Bn); Ser(Me); Thi; alloThr; Thr(Bn); Thz; Thz(5,5Me₂); Tic; Tic(7OH); Trp(7Aza); Trp(5Br); Trp(6Br); Trp(6CF₃); Trp(5Cl); Trp(6Cl); Trp(5,6Cl); Trp(5OH); Tyr(Bn); Tyr (Me); Tyr(4MeOCOBn); Tyr(Ph); Tyr(4OHPh); Tza; Gln(Alk1); Gln(Alk2); Gln(Alk3); Gln(Alk4); Gln (Alk5); Gln(Alk6); Gln(Alk7); Gln(Alk8); Gln(Alk9); Gln(Alk10); Gln(Alk11); Gln(Alk12); Gln(Alk13); Gln (Alk14); Gln(Alk15); Gln(Alk16); Gln(Alk17); Gln (Alk18); Gln(Alk19); Gln(Alk20); Gln(Alk21); Gln (Alk22); Gln(Alk23); Gln(Alk24); Gln(Alk25); Gln (Alk26); Gln(Alk27); Gln(Alk28); Gln(Alk29); Gln (Alk30); Gln(Alk31); Gln(Alk32); Gln(Alk33); Gln (Alk34); Glu(cN1); Glu(cN2); Glu(cN3); Glu(cN4); Glu(cN5); Glu(cN6); Glu(cN7); Glu(cN8); Glu(cN9); Glu(cN10); Glu(cN11); Glu(cN12); Glu(cN13); Glu (cN14); Glu(cN15); Glu(cN16); Glu(cN17); Lys(Ar1); Lys(Ar2); Lys(Ar3); Lys(Ar4); Lys(Ar5); Lys(Ar6); Lys (Ar7); Lys(Ar8); Lys(Ar9); Lys(Ar10); Lys(Ar11); Lys (Ar12); Orn(Ar1); Orn(Ar2); Orn(Ar3); Orn(Ar4); Orn (Ar5); Orn(Ar6); Orn(Ar7); Orn(Ar8); Orn(Ar9); Orn (Ar10); Orn(Ar11); Orn(Ar12); Dab(Ar1); Dab(Ar2); Dab(Ar3); Dab(Ar4); Dab(Ar5); Dab(Ar6); Dab(Ar7); Dab(Ar8); Dab(Ar9); Dab(Ar10); Dab(Ar11); Dab (Ar12); Dab(S1); Dab(S2); Dab(S3); Dab(S4); Dab (S5); Dab(S6); Dab(S7); Dab(S8); Dab(S9); Dab(S10); Dab(S11); Dab(S12); Dab(S13); Dab(S14); Dab(S15); Dab(S16); Dab(S17); Dab(S18); Dab(A1); Dab(A2); Dab(A3); Dab(A4); Dab(A5); Dab(A6); Dab(A7); Dab (A8); Dab(A9); Dab(A10); Dab(A11); Dab(A12); Dab (A13); Dab(A14); Dab(A15); Dab(A16); Dab(A17); Dab(A18); Dab(A19); Dab(A20); Dab(A21); Dab (A22); Dab(A23); Dab(A24); Dab(A25); Dab(A26); Dab(A27); Dab(A28); Dab(A29); Dab(A30); Dab (A31); Dab(A32); Dab(A33); Dab(A34); Dab(A35); Dab(A36); Dab(A37); Dab(A38); Dab(A39); Dab (A40); Dab(A41); Dab(A42); Dab(A43); Dab(A44); Dab(A45); Dab(A46); Dab(A47); Dab(A48); Dab (A49); Dab(A50); Dab(A51); Dab(A52); Dab(A53); Dab(A54); Dab(A55); Orn(A1); Orn(A2); Orn(A3); Orn(A4); Orn(A5); Orn(A6); Orn(A7); Orn(A8); Orn (A9); Orn(A10); Orn(A11); Orn(A12); Orn(A13); Orn (A14); Orn(A15); Orn(A16); Orn(A17); Orn(A18); Orn (A19); Orn(A20); Orn(A21); Orn(A22); Orn(A23); Orn (A24); Orn(A25); Orn(A26); Orn(A27); Orn(A28); Orn (A29); Orn(A30); Orn(A31); Orn(A32); Orn(A33); Orn (A34); Orn(A35); Orn(A36); Orn(A37); Orn(A38); Orn (A39); Orn(A40); Orn(A41); Orn(A42); Orn(A43); Orn (A44); Orn(A45); Orn(A46); Orn(A47); Orn(A48); Orn (A49); Orn(A50); Orn(A51); Orn(A52); Orn(A53); Orn (A54); Orn(A55); Orn(A56); Asn(Alk1); Asn(Alk2); Asn(Alk3); Asn(Alk4); Asn(Alk5); Asn(Alk6); Asn (Alk7); Asn(Alk8); Asn(Alk9); Asn(Alk10); Asn (Alk11); Asn(Alk12); Asn(Alk13); Asn(Alk14); Asn (Alk15); Asn(Alk16); Asn(Alk17); Asn(Alk18); Asn (Alk19); Asn(Alk20); Asn(Alk21); Asn(Alk22); Asn (Alk23); Asn(Alk24); Asn(Alk25); Asn(Alk26); Asn (Alk27); Asn(Alk28); Asn(Alk29); Asn(Alk30); Asn (Alk31); Asn(Alk32); Asn(Alk33); Asn(Alk34); Asp (cN1); Asp(cN2); Asp(cN3); Asp(cN4); Asp(cN5); Asp (cN6); Asp(cN7); Asp(cN8); Asp(cN9); Asp(cN10); Asp(cN11); Asp(cN12); Asp(cN13); Asp(cN14); Asp (cN15); Asp(cN16); Asp(cN17); Dap(Ar1); Dap(Ar2); Dap(Ar3); Dap(Ar4); Dap(Ar5); Dap(Ar6); Dap(Ar7); Dap(Ar8); Dap(Ar9); Dap(Ar10); Dap(Ar11); Dap (Ar12); Dap(S1); Dap(S2); Dap(S3); Dap(S4); Dap (S5); Dap(S6); Dap(S7); Dap(S8); Dap(S9); Dap(S10); Dap(S11); Dap(S12); Dap(S13); Dap(S14); Dap(S15); Dap(S16); Dap(S17); Dap(S18); Dap(A1); Dap(A2); Dap(A3); Dap(A4); Dap(A5); Dap(A6); Dap(A7); Dap (A8); Dap(A9); Dap(A10); Dap(A11); Dap(A12); Dap (A13); Dap(A14); Dap(A15); Dap(A16); Dap(A17); Dap(A18); Dap(A19); Dap(A20); Dap(A21); Dap (A22); Dap(A23); Dap(A24); Dap(A25); Dap(A26); Dap(A27); Dap(A28); Dap(A29); Dap(A30); Dap (A31); Dap(A32); Dap(A33); Dap(A34); Dap(A35); Dap(A36); Dap(A37); Dap(A38); Dap(A39); Dap (A40); Dap(A41); Dap(A42); Dap(A43); Dap(A44); Dap(A45); Dap(A46); Dap(A47); Dap(A48); Dap (A49); Dap(A50); Dap(A51); Dap(A52); Dap(A53); Dap(A54); or Dap(A55);

P² is $^D$Arg; $^D$hArg; $^D$Agb; $^D$Lys; $^D$Orn; $^D$Cit; $^D$Thr; $^D$Dab; $^D$Dab; $^D$Phe; $^D$Phe(4CF₃); $^D$Trp; $^D$His; $^D$Tyr; $^D$2Pal; $^D$3Pal; $^D$4Pal; $^D$Lys(Ar1); $^D$Lys(Ar2); $^D$Lys(Ar3); $^D$Lys(Ar4); $^D$Lys(Ar5); $^D$Lys(Ar6); $^D$Lys(Ar7); $^D$Lys(Ar8); $^D$Lys (Ar9); $^D$Lys(Ar10); $^D$Lys(Ar11); $^D$Lys(Ar12); $^D$Orn(A41); $^D$Orn(A56); $^D$Orn(Ar1); $^D$Orn(Ar2); $^D$Orn(Ar3); $^D$Orn (Ar4); $^D$Orn(Ar5); $^D$Orn(Ar6); $^D$Orn(Ar7); $^D$Orn(Ar8); $^D$Orn(Ar9); $^D$Orn(Ar10); $^D$Orn(Ar11); $^D$Orn(Ar12); $^D$Dab (Ar1); $^D$Dab(Ar2); $^D$Dab(Ar3); $^D$Dab(Ar4); $^D$Dab(Ar5); $^D$Dab(Ar6); $^D$Dab(Ar7); $^D$Dab(Ar8); $^D$Dab(Ar9); $^D$Dab (Ar10); $^D$Dab(Ar11); $^D$Dab(Ar12); $^D$Dap(Ar1); $^D$Dap (Ar2); $^D$Dap(Ar3); $^D$Dap(Ar4); $^D$Dap(Ar5); $^D$Dap(Ar6); $^D$Dap(Ar7); $^D$Dap(Ar8); $^D$Dap(Ar9); $^D$Dap(Ar10); $^D$Dap (Ar11); or $^D$Dap(Ar12);

and pharmaceutically acceptable salts thereof.

In an even further particular embodiment of the invention the elements of general formula (I) are defined as follows T¹ is $^D$Pro; $^D$Pip; $^D$Tic; $^D$Tiq; $^D$Oic; $^D$Azt; $^D$Pro((3R)OH); $^D$Pro((3S)OH); $^D$Pro((3R)NH₂); $^D$Pro((3S)NH₂); $^D$Pro ((4R)OH); $^D$Pro((4S)OH); $^D$Pro((4R)NH₂); $^D$Pro((4S) NH₂); $^D$Pro((4S)NHBz); or $^D$Mor;

T² is Thr; alloThr; Ser; hSer; Pro((3R)OH); Pro((3S)OH); Hyp(Bn); (4S)-Hyp(Bn); Pro((3R)NH₂); Pro((3S)NH₂); Pro((4R)NH₂); Pro((4S)NH₂); Pro((4S)F); Pro((4S) NHBz); or Mor; or when T¹ is $^D$Pro((3R)OH); $^D$Pro((3S)OH); $^D$Pro((3R)NH₂); $^D$Pro((3S)NH₂); $^D$Pro((4R)NH₂); $^D$Pro((4S)NH₂); $^D$Pro ((4S)NHBz); or $^D$Mor then T² can in addition be Pro; Pip; Tic; Tiq; Oic; or Azt;

P¹ is Ile; Nle; Leu; Val; Chg; Cha; Abu; Ala; Ala(cPr); Ala (1Pyraz); Ala(Tet); Trp; 1Nal; 2Nal; Phe; Tyr; 2 Pal; 3 Pal; 4 Pal; Thr; His; Arg; hArg; Agb; Pip; Orn(Ar2); or Orn (A56);

P² is $^D$Arg; $^D$hArg; $^D$Agb; $^D$Lys; $^D$Orn; $^D$Cit; $^D$Thr; $^D$Dab; $^D$Dap; $^D$Phe; $^D$Trp; $^D$His; $^D$Tyr; $^D$2 Pal; $^D$3 Pal; or $^D$4 Pal;

P³ is Arg; hArg; Agb; Agp; Lys; Orn; Orn(A41); Orn(A56); Orn(Ar2); Orn(Ar4); Orn(Ar7); Cit; Thr; Dab; Dap; Phe; Trp; His; Tyr; or Ile

P⁴ is Trp; His; Phe; Phe(4CF₃); 1Nal; 2Nal; Tyr; Leu; Ile; Arg; hArg; Lys; Dab; Dap; Orn; Orn(A56); or Orn(Ar7);

and pharmaceutically acceptable salts thereof.

In an even further specific embodiment of the invention the elements of general formula (I) are defined as follows T¹ is ᴰPro; ᴰPip; ᴰTic; ᴰPro((4S)OH); ᴰPro((4R)NH₂); or ᴰPro((4S)NH₂);

T² is Thr; alloThr; Ser; hSer; Pro((3S)OH); (4S)-Hyp(Bn); Pro((4R)NH₂); Pro((4S)NH₂); Pro((4S)F); Pro((4S)NHBz); or Mor;

P¹ is Ile; Nle; Leu; Val; Chg; Cha; Abu; Ala; Trp; 1Nal; Tyr; 3Pal; Thr; His; Arg; hArg; Agb; Pip; Ala(1Pyraz); Ala(Tet); Orn(Ar2); or Orn(A56);

P² is ᴰArg; ᴰLys; ᴰOrn; ᴰCit; ᴰThr; ᴰDab; ᴰPhe; ᴰTrp; ᴰHis; or ᴰ3 Pal;

P³ is Arg; hArg; Agb; Agp; Lys; Orn; Orn(A41); Orn(A56); Orn(Ar2); Orn(Ar4); Orn(Ar7); Dab; Trp; or His;

P⁴ is Trp; His; Phe; Phe(4CF₃); 1Nal; 2Nal; Tyr; Ile; Arg; hArg; Lys; Dab; Orn; Orn(A56); or Orn(Ar7);

and pharmaceutically acceptable salts thereof.

Hereinafter follows a list of abbreviations, corresponding to generally adopted usual practice of amino acids, which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogs with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Glu L-Glutamic acid
Gln L-Glutamine
Gly Glycine
His L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Abu (S)-2-aminobutanoic acid
Agb (S)-2-amino-4-guanidinobutanoic acid
Agp (S)-2-amino-3-guanidinopropanoic acid
Ala(tBu) (S)-2-amino-4,4-dimethylpentanoic acid
Ala(cPr) (S)-2-amino-3-cyclopropylpropanoic acid
Ala(2Furyl) (S)-2-amino-3-(furan-2-yl)propanoic acid
Ala(3Furyl) (S)-2-amino-3-(furan-3-yl)propanoic acid
Ala(Ppz) (S)-2-amino-3-(piperazin-1-yl)propanoic acid
Ala(1Pyraz) (S)-2-amino-3-(1H-pyrazol-1-yl)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Ala(Tet) (S)-2-amino-3-(2H-tetrazol-2-yl)propanoic acid
Azt (S)-azetidine-2-carboxylic acid
Bbta (S)-2-amino-3-(1-benzothiophen-3-yl)propanoic acid
Bip (S)-2-amino-3-(4-biphenylyl)propanoic acid
Cha (S)-2-amino-3-cyclohexylpropanoic acid
Dab (S)-2,4-diaminobutanoic acid
Dab(Ac) (S)-4-acetamido-2-aminobutanoic acid
Dab(cPr) (S)-2-amino-4-(cyclopropylamino)butanoic acid
Dab(iPr) (S)-2-amino-4-(isopropylamino)butanoic acid
Dab(4Me₂NPhSO₂) (S)-2-amino-4-(4-(dimethylamino)phenylsulfonamido)butanoic acid
Dab(MeOEtNCO) (S)-2-amino-4-(3-(2-methoxyethyl)ureido)butanoic acid
Dab(MePpzCO) (S)-2-amino-4-(4-methylpiperazine-1-carboxamido)butanoic acid
Dab(MeSO₂) (S)-2-amino-4-(methylsulfonamido)butanoic acid
Dab(morphCO) (S)-2-amino-4-(morpholine-4-carboxamido)butanoic acid
Dab(1Nal) (S)-2-amino-4-((S)-2-amino-3-(naphthalen-1-yl)propanamido)-butanoic acid
Dab(2Nal) (S)-2-amino-4-((S)-2-amino-3-(naphthalen-2-yl)-propanamido)-butanoic acid
Dap (S)-2,4-diaminopropanoic acid
Dap(CONH₂) (S)-2-amino-3-ureidopropanoic acid
Dap(MeOEt) (S)-2-amino-3-(2-methoxyethylamino)propanoic acid
Dap((MeOEt)₂) (S)-2-amino-3-(bis(2-methoxyethyl)amino)propanoic acid
Deg 2-amino-2-ethylbutanoic acid
Gly(tBu) (S)-2-amino-3,3-dimethylbutanoic acid
hArg (S)-2-amino-6-guanidinohexanoic acid
hCha (S)-2-amino-4-cyclohexylbutanoic acid
hCys (S)-2-amino-4-mercaptobutanoic acid
hHis (S)-2-amino-4-(1H-imidazol-5-yl)butanoic acid
hLys (S)-2,7-diaminoheptanoic acid
hPhe (S)-2-amino-4-phenylbutanoic acid
hSer (S)-2-amino-4-hydroxybutanoic acid
hSer(Me) (S)-2-amino-4-methoxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Hyp(Bn) (2S,4R)-4-(benzyloxy)pyrrolidine-2-carboxylic acid
(4S)-Hyp(Bn) (2S,4S)-4-(benzyloxy)pyrrolidine-2-carboxylic acid
Hyp(4BrBn) (2S,4R)-4-(4-bromobenzyloxy)pyrrolidine-2-carboxylic acid
Hyp(3CNBn) (2S,4R)-4-(3-cyanobenzyloxy)pyrrolidine-2-carboxylic acid
Hyp(4CNBn) (2S,4R)-4-(4-cyanobenzyloxy)pyrrolidine-2-carboxylic acid
Hyp(CONHPh) (2S,4R)-4-(phenylcarbamoyloxy)pyrrolidine-2-carboxylic acid
Hyp(Ph) (2S,4R)-4-phenoxypyrrolidine-2-carboxylic acid
Lys(Ac) (S)-6-acetamido-2-aminohexanoic acid
Lys(Bz) (S)-2-amino-6-benzamidohexanoic acid
Lys(cPr) (S)-2-amino-6-(cyclopropylamino)hexanoic acid
Lys(iPr) (S)-2-amino-6-(isopropylamino)hexanoic acid
Lys(Me) (S)-2-amino-6-(methylamino)hexanoic acid
Lys(Nic) (S)-2-amino-6-(nicotinamido)hexanoic acid
Lys((5R)OH) (2S,5R)-2,6-diamino-5-hydroxyhexanoic acid
Lys(4Oxa) (S)-2-amino-3-(2-aminoethoxy)propanoic acid
Met(O₂) (S)-2-amino-4-(methylsulfonyl)butanoic acid
Mor (S)-morpholine-3-carboxylic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
OctG (S)-2-aminodecanoic acid
Oic (2S,3aS,7aS)-octahydro-1H-indole-2-carboxylic acid Orn(cPr) (S)-2-amino-5-(cyclopropylamino)pentanoic acid
Orn(iPr) (S)-2-amino-5-(isopropylamino)pentanoic acid
2 Pal (S)-2-amino-3-(pyridine-2-yl)-propionic acid
3 Pal (S)-2-amino-3-(pyridine-3-yl)-propionic acid
4 Pal (S)-2-amino-3-(pyridine-4-yl)-propionic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(4CN) (S)-2-amino-3-(4-cyanophenyl)propanoic acid
Phe(4CF$_3$) (S)-2-amino-3-(4-(trifluoromethyl))propanoic acid
Phe(4COOMe) (S)-2-amino-3-(4-(methoxycarbonyl)phenyl)propanoic acid
Phg (S)-2-amino-2-phenylacetic acid
Pip (S)-piperidine-2-carboxylic acid
Pro((4R)Bn) (2S,4R)-4-benzylpyrrolidine-2-carboxylic acid
Pro((4S)F) (2S,4S)-4-fluoropyrrolidine-2-carboxylic acid
Pro((4S)cHex) (2S,4S)-4-cyclohexylpyrrolidine-2-carboxylic acid
Pro((3R)NH$_2$) (2S,3R)-3-aminopyrrolidine-2-carboxylic acid
Pro((3S)NH$_2$) (2S,3S)-3-aminopyrrolidine-2-carboxylic acid
Pro((4R)NH$_2$) (2S,4R)-4-aminopyrrolidine-2-carboxylic acid
Pro((4S)NH$_2$) (2S,4S)-4-aminopyrrolidine-2-carboxylic acid
Pro((4S)NHBz) (2S,4S)-4-benzamidopyrrolidine-2-carboxylic acid
Pro(5,5Me$_2$) (S)-3,3-dimethylpyrrolidine-2-carboxylic acid
Pro((3R)OH) (2S,3R)-3-hydroxypyrrolidine-2-carboxylic acid
Pro((3S)OH) (2S,3S)-3-hydroxypyrrolidine-2-carboxylic acid
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thz (4R)-1,3-thiazolidine-4-carboxylic acid
Thz(5,5Me$_2$) (4R)-5,5-dimethyl-1,3-thiazolidine-4-carboxylic acid
Tic (3S)-1,2,3,4-Tetrahydroisoquinoline-3-carboxylic acid
Tic(7OH) (3S)-7-hydroxy-1,2,3,4-tetrahydroisoquinoline-3-carboxylic acid
Tiq (S)-1,2,3,4-tetrahydroisoquinoline-1-carboxylic acid
Trp(7Aza) (R)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF$_3$) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(4MeOCOBn) (S)-2-amino-3-(4-(4-(methoxycarbonyl)benzyloxy)phenyl)-propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tza (S)-2-amino-3-(thiazol-4-yl)propanoic acid
Asn(Alk1) (S)-2-amino-4-oxo-4-(2,2,2-trifluoroethylamino)butanoic acid
Asn(Alk2) (S)-2-amino-4-(cyclopentylamino)-4-oxobutanoic acid
Asn(Alk3) (S)-2-amino-4-(cyclohexylamino)-4-oxobutanoic acid
Asn(Alk4) (S)-2-amino-4-oxo-4-(tetrahydro-2H-pyran-4-ylamino)butanoic acid
Asn(Alk5) (S)-2-amino-4-(2-hydroxyethylamino)-4-oxobutanoic acid
Asn(Alk6) (S)-2-amino-4-(2-methoxyethylamino)-4-oxobutanoic acid
Asn(Alk7) (S)-2-amino-4-(2-aminoethylamino)-4-oxobutanoic acid
Asn(Alk8) (S)-2-amino-4-(2-(dimethylamino)ethylamino)-4-oxobutanoic acid
Asn(Alk9) (S)-2-amino-4-((2-methoxyethyl)(methyl)amino)-4-oxobutanoic acid
Asn(Alk10) (S)-2-amino-4-((2-(dimethylamino)ethyl)(methyl)amino)-4-oxobutanoic acid
Asn(Alk11) (S)-2-amino-4-(3-aminopropylamino)-4-oxobutanoic acid
Asn(Alk12) (S)-2-amino-4-(3-(dimethylamino)propylamino)-4-oxobutanoic acid
Asn(Alk13) (S)-2-amino-4-((3-(dimethylamino)propyl)(methyl)amino)-4-oxobutanoic acid
Asn(Alk14) (S)-4-(3-acetamidopropylamino)-2-amino-4-oxobutanoic acid
Asn(Alk15) (S)-2-amino-4-oxo-4-(2-(pyrrolidin-1-yl)ethylamino)butanoic acid
Asn(Alk16) (S)-2-amino-4-(2-morpholinoethylamino)-4-oxobutanoic acid
Asn(Alk17) (S)-2-amino-4-(3-morpholinopropylamino)-4-oxobutanoic acid
Asn(Alk18) (S)-2-amino-4-(1,3-dihydroxypropan-2-ylamino)-4-oxobutanoic acid
Asn(Alk19) (S)-2-amino-4-(4-hydroxy-3-(hydroxymethyl)butylamino)-4-oxobutanoic acid
Asn(Alk20) (S)-2-amino-4-oxo-4-(piperidin-4-ylmethylamino)butanoic acid
Asn(Alk21) (S)-2-amino-4-(methyl((tetrahydro-2H-pyran-4-yl)methyl)amino)-4-oxobutanoic acid
Asn(Alk22) (2S)-2-amino-4-(methyl(2-(1-methylpyrrolidin-2-yl)ethyl)amino)-4-oxobutanoic acid
Asn(Alk23) (S)-2-amino-4-oxo-4-(thiazol-2-ylmethylamino)butanoic acid
Asn(Alk24) (S)-2-amino-4-((1-methyl-1H-imidazol-4-yl)methylamino)-4-oxobutanoic acid
Asn(Alk25) (S)-2-amino-4-(benzylamino)-4-oxobutanoic acid
Asn(Alk26) (S)-2-amino-4-(4-(methylsulfonyl)benzylamino)-4-oxobutanoic acid
Asn(Alk27) (S)-2-amino-4-oxo-4-(pyridin-3-ylmethylamino)butanoic acid
Asn(Alk28) (S)-2-amino-4-oxo-4-(4-(trifluoromethyl)benzylamino)butanoic acid
Asn(Alk29) (S)-2-amino-4-(2-methoxybenzylamino)-4-oxobutanoic acid Asn(Alk30) (S)-2-amino-4-((1-methyl-1H-benzo[d]imidazol-2-yl)methylamino)-4-oxobutanoic acid
Asn(Alk31) (S)-2-amino-4-((4-methyl-6-(trifluoromethyl)pyrimidin-2-yl)-methylamino)-4-oxobutanoic acid
Asn(Alk32) (S)-4-(2-(1H-indol-3-yl)ethylamino)-2-amino-4-oxobutanoic acid
Asn(Alk33) (2S)-2-amino-4-(2,3-dihydro-1H-inden-1-ylamino)-4-oxobutanoic acid
Asn(Alk34) (2S)-2-amino-4-oxo-4-(1,2,3,4-tetrahydronaphthalen-1-ylamino)-butanoic acid
Asp(cN1) (S)-2-amino-4-(azetidin-1-yl)-4-oxobutanoic acid
Asp(cN2) (S)-2-amino-4-oxo-4-(pyrrolidin-1-yl)butanoic acid
Asp(cN3) (S)-2-amino-4-oxo-4-(piperidin-1-yl)butanoic acid
Asp(cN4) (S)-2-amino-4-morpholino-4-oxobutanoic acid
Asp(cN5) (S)-2-amino-4-oxo-4-(piperazin-1-yl)butanoic acid
Asp(cN6) (S)-2-amino-4-(4-methylpiperazin-1-yl)-4-oxobutanoic acid
Asp(cN7) (S)-2-amino-4-(4-hydroxypiperidin-1-yl)-4-oxobutanoic acid
Asp(cN8) (S)-2-amino-4-(4-(dimethylamino)piperidin-1-yl)-4-oxobutanoic acid
Asp(cN9) (2S)-2-amino-4-(7-methyl-1,7-diazaspiro[4.4]nonan-1-yl)-4-oxobutanoic acid
Asp(cN10) (S)-2-amino-4-(indolin-1-yl)-4-oxobutanoic acid
Asp(cN11) (S)-2-amino-4-(5,6-dihydro-1,7-naphthyridin-7(8H)-yl)-4-oxobutanoic acid
Asp(cN12) (S)-2-amino-4-(3,4-dihydro-1,5-naphthyridin-1(2H)-yl)-4-oxobutanoic acid
Asp(cN13) (S)-2-amino-4-(5,6-dihydroimidazo[1,2-a]pyrazin-7(8H)-yl)-4-oxobutanoic acid
Asp(cN14) (S)-4-(4-(1H-imidazol-1-yl)piperidin-1-yl)-2-amino-4-oxobutanoic acid
Asp(cN15) (S)-4-(4-(1H-imidazol-2-yl)piperidin-1-yl)-2-amino-4-oxobutanoic acid
Asp(cN16) (S)-2-amino-4-(1,4-oxazepan-4-yl)-4-oxobutanoic acid
Asp(cN17) (S)-2-amino-4-(4-methyl-1,4-diazepan-1-yl)-4-oxobutanoic acid
Gln(Alk1) (S)-2-amino-5-oxo-5-(2,2,2-trifluoroethylamino)pentanoic acid
Gln(Alk2) (S)-2-amino-5-(cyclopentylamino)-5-oxopentanoic acid
Gln(Alk3) (S)-2-amino-5-(cyclohexylamino)-5-oxopentanoic acid
Gln(Alk4) (S)-2-amino-5-oxo-5-(tetrahydro-2H-pyran-4-ylamino)pentanoic acid
Gln(Alk5) (S)-2-amino-5-(2-hydroxyethylamino)-5-oxopentanoic acid
Gln(Alk6) (S)-2-amino-5-(2-methoxyethylamino)-5-oxopentanoic acid
Gln(Alk7) (S)-2-amino-5-(2-aminoethylamino)-5-oxopentanoic acid
Gln(Alk8) (S)-2-amino-5-(2-(dimethylamino)ethylamino)-5-oxopentanoic acid
Gln(Alk9) (S)-2-amino-5-((2-methoxyethyl)(methyl)amino)-5-oxopentanoic acid
Gln(Alk10) (S)-2-amino-5-((2-(dimethylamino)ethyl)(methyl)amino)-5-oxopentanoic acid
Gln(Alk11) (S)-2-amino-5-(3-aminopropylamino)-5-oxopentanoic acid
Gln(Alk12) (S)-2-amino-5-(3-(dimethylamino)propylamino)-5-oxopentanoic acid
Gln(Alk13) (S)-2-amino-5-((3-(dimethylamino)propyl)(methyl)amino)-5-oxopentanoic acid
Gln(Alk14) (S)-5-(3-acetamidopropylamino)-2-amino-5-oxopentanoic acid
Gln(Alk15) (S)-2-amino-5-oxo-5-(2-(pyrrolidin-1-yl)ethylamino)pentanoic acid
Gln(Alk16) (S)-2-amino-5-(2-morpholinoethylamino)-5-oxopentanoic acid
Gln(Alk17) (S)-2-amino-5-(3-morpholinopropylamino)-5-oxopentanoic acid
Gln(Alk18) (S)-2-amino-5-(1,3-dihydroxypropan-2-ylamino)-5-oxopentanoic acid
Gln(Alk19) (S)-2-amino-5-(4-hydroxy-3-(hydroxymethyl)butylamino)-5-oxopentanoic acid
Gln(Alk20) (S)-2-amino-5-oxo-5-(piperidin-4-ylmethylamino)pentanoic acid
Gln(Alk21) (S)-2-amino-5-(methyl((tetrahydro-2H-pyran-4-yl)methyl)amino)-5-oxopentanoic acid
Gln(Alk22) (2S)-2-amino-5-(methyl(2-(1-methylpyrrolidin-2-yl)ethyl)amino)-5-oxopentanoic acid
Gln(Alk23) (S)-2-amino-5-oxo-5-(thiazol-2-ylmethylamino)pentanoic acid
Gln(Alk24) (S)-2-amino-5-((1-methyl-1H-imidazol-4-yl)methylamino)-5-oxopentanoic acid
Gln(Alk25) (S)-2-amino-5-(benzylamino)-5-oxopentanoic acid
Gln(Alk26) (S)-2-amino-5-(4-(methylsulfonyl)benzylamino)-5-oxopentanoic acid
Gln(Alk27) (S)-2-amino-5-oxo-5-(pyridin-3-ylmethylamino)pentanoic acid
Gln(Alk28) (S)-2-amino-5-oxo-5-(4-(trifluoromethyl)benzylamino)pentanoic acid
Gln(Alk29) (S)-2-amino-5-(2-methoxybenzylamino)-5-oxopentanoic acid
Gln(Alk30) (S)-2-amino-5-((1-methyl-1H-benzo[d]imidazol-2-yl)methylamino)-5-oxopentanoic acid
Gln(Alk31) (S)-2-amino-5-((4-methyl-6-(trifluoromethyl)pyrimidin-2-yl)-methylamino)-5-oxopentanoic acid
Gln(Alk32) (S)-5-(2-(1H-indol-3-yl)ethylamino)-2-amino-5-oxopentanoic acid
Gln(Alk33) (2S)-2-amino-5-(2,3-dihydro-1H-inden-1-ylamino)-5-oxopentanoic acid
Gln(Alk34) (2S)-2-amino-5-oxo-5-(1,2,3,4-tetrahydronaphthalen-1-ylamino)-pentanoic acid
Glu(cN1) (S)-2-amino-5-(azetidin-1-yl)-5-oxopentanoic acid
Glu(cN2) (S)-2-amino-5-oxo-5-(pyrrolidin-1-yl)pentanoic acid
Glu(cN3) (S)-2-amino-5-oxo-5-(piperidin-1-yl)pentanoic acid
Glu(cN4) (S)-2-amino-5-morpholino-5-oxopentanoic acid
Glu(cN5) (S)-2-amino-5-oxo-5-(piperazin-1-yl)pentanoic acid
Glu(cN6) (S)-2-amino-5-(4-methylpiperazin-1-yl)-5-oxopentanoic acid
Glu(cN7) (S)-2-amino-5-(4-hydroxypiperidin-1-yl)-5-oxopentanoic acid
Glu(cN8) (S)-2-amino-5-(4-(dimethylamino)piperidin-1-yl)-5-oxopentanoic acid
Glu(cN9) (2S)-2-amino-5-(7-methyl-1,7-diazaspiro[4.4]nonan-1-yl)-5-oxopentanoic acid
Glu(cN10) (S)-2-amino-5-(indolin-1-yl)-5-oxopentanoic acid
Glu(cN11) (S)-2-amino-5-(5,6-dihydro-1,7-naphthyridin-7(8H)-yl)-5-oxopentanoic acid
Glu(cN12) (S)-2-amino-5-(3,4-dihydro-1,5-naphthyridin-1(2H)-yl)-5-oxopentanoic acid
Glu(cN13) (S)-2-amino-5-(5,6-dihydroimidazo[1,2-a]pyrazin-7(8H)-yl)-5-oxopentanoic acid Glu(cN14) (S)-5-(4-(1H-imidazol-1-yl)piperidin-1-yl)-2-amino-5-oxopentanoic acid
Glu(cN15) (S)-5-(4-(1H-imidazol-2-yl)piperidin-1-yl)-2-amino-5-oxopentanoic acid
Glu(cN16) (S)-2-amino-5-(1,4-oxazepan-4-yl)-5-oxopentanoic acid
Glu(cN17) (S)-2-amino-5-(4-methyl-1,4-diazepan-1-yl)-5-oxopentanoic acid
Lys(Ar1) (S)-2-amino-6-(pyridin-2-ylamino)hexanoic acid
Lys(Ar2) (S)-2-amino-6-(pyrimidin-2-ylamino)hexanoic acid
Lys(Ar3) (S)-2-amino-6-(1,2,4-triazin-3-ylamino)hexanoic acid
Lys(Ar4) (S)-2-amino-6-(pyridin-2-ylmethylamino)hexanoic acid
Lys(Ar5) (S)-2-amino-6-(pyrimidin-2-ylmethylamino)hexanoic acid
Lys(Ar6) (S)-2-amino-6-(bis(pyrimidin-2-ylmethyl)amino)hexanoic acid
Lys(Ar7) (S)-2-amino-6-(((1-methyl-1H-imidazol-2-yl)methyl)amino)hexanoic acid
Lys(Ar8) (S)-2-amino-6-(((4-methyl-4H-1,2,4-triazol-3-yl)methyl)amino)hexanoic acid
Lys(Ar9) (S)-2-amino-6-(((1-methyl-1H-1,2,4-triazol-5-yl)methyl)amino)hexanoic acid
Lys(Ar10) (S)-2-amino-6-(1H-pyrazol-1-yl)hexanoic acid
Lys(Ar11) (S)-2-amino-6-(bis((1-methyl-1H-imidazol-2-yl)methyl)amino)-hexanoic acid
Lys(Ar12) (S)-2-amino-6-(1H-1,2,4-triazol-1-yl)hexanoic acid
Orn(Ar1) (S)-2-amino-5-(pyridin-2-ylamino)pentanoic acid
Orn(Ar2) (S)-2-amino-5-(pyrimidin-2-ylamino)pentanoic acid
Orn(Ar3) (S)-2-amino-5-(1,2,4-triazin-3-ylamino)pentanoic acid
Orn(Ar4) (S)-2-amino-5-((pyridin-2-ylmethyl)amino)pentanoic acid
Orn(Ar5) (S)-2-amino-5-(pyrimidin-2-ylmethylamino)pentanoic acid
Orn(Ar6) (S)-2-amino-5-(bis(pyrimidin-2-ylmethyl)amino)pentanoic acid
Orn(Ar7) (S)-2-amino-5-(((1-methyl-1H-imidazol-2-yl)methyl)amino)pentanoic acid
Orn(Ar8) (S)-2-amino-5-(((4-methyl-4H-1,2,4-triazol-3-yl)methyl)amino)-pentanoic acid
Orn(Ar9) (S)-2-amino-5-(((1-methyl-1H-1,2,4-triazol-5-yl)methyl)amino)-pentanoic acid
Orn(Ar10) (S)-2-amino-5-(1H-pyrazol-1-yl)pentanoic acid
Orn(Ar11) (S)-2-amino-5-(bis((1-methyl-1H-imidazol-2-yl)methyl)amino)-pentanoic acid
Orn(Ar12) (S)-2-amino-5-(1H-1,2,4-triazol-1-yl)pentanoic acid
Orn(A1) (S)-5-acetamido-2-aminopentanoic acid
Orn(A2) (S)-2-amino-5-propionamidopentanoic acid
Orn(A3) (S)-2-amino-5-isobutyramidopentanoic acid
Orn(A4) (S)-2-amino-5-(cyclopropanecarboxamido)pentanoic acid
Orn(A5) (S)-2-amino-5-(3,3,3-trifluoropropanamido)pentanoic acid
Orn(A6) (S)-2-amino-5-(4,4,4-trifluorobutanamido)pentanoic acid
Orn(A7) (S)-2-amino-5-(3-aminopropanamido)pentanoic acid
Orn(A8) (S)-2-amino-5-(4-aminobutanamido)pentanoic acid
Orn(A9) (S)-2-amino-5-(5-aminopentanamido)pentanoic acid
Orn(A10) (S)-2-amino-5-(3-methoxypropanamido)pentanoic acid
Orn(A11) (S)-2-amino-5-(3-(methylamino)propanamido)pentanoic acid
Orn(A12) (S)-2-amino-5-(3-(dimethylamino)propanamido)pentanoic acid
Orn(A13) (S)-2-amino-5-(3-(phenylamino)propanamido)pentanoic acid
Orn(A14) (2S)-2-amino-5-(3-aminobutanamido)pentanoic acid
Orn(A15) (S)-2-amino-5-(3-amino-3-methylbutanamido)pentanoic acid
Orn(A16) (S)-2-amino-5-(3-(methylsulfonyl)propanamido)pentanoic acid
Orn(A17) (S)-2-amino-5-(2-cyclopropylacetamido)pentanoic acid
Orn(A18) (2S)-2-amino-5-(2-(pyrrolidin-3-yl)acetamido)pentanoic acid
Orn(A19) (2S)-2-amino-5-(2-(pyrrolidin-2-yl)acetamido)pentanoic acid
Orn(A20) (S)-2-amino-5-(2-(piperidin-4-yl)acetamido)pentanoic acid
Orn(A21) (2S)-2-amino-5-(2-(piperidin-3-yl)acetamido)pentanoic acid
Orn(A22) (2S)-2-amino-5-(2-(piperidin-2-yl)acetamido)pentanoic acid
Orn(A23) (S)-2-amino-5-(3-(piperidin-1-yl)propanamido)pentanoic acid
Orn(A24) (S)-2-amino-5-(3-(piperazin-1-yl)propanamido)pentanoic acid
Orn(A25) (S)-2-amino-5-(3-(4-methylpiperazin-1-yl)propanamido)pentanoic acid
Orn(A26) (S)-2-amino-5-(3-morpholinopropanamido)pentanoic acid
Orn(A27) (S)-2-amino-5-(2-(1-aminocyclohexyl)acetamido)pentanoic acid
Orn(A28) (S)-2-amino-5-(2-(4-aminotetrahydro-2H-pyran-4-yl)acetamido)-pentanoic acid
Orn(A29) (2S)-2-amino-5-(2,2-dimethyl-1,3-dioxolane-4-carboxamido)pentanoic acid
Orn(A30) (S)-2-amino-5-benzamidopentanoic acid
Orn(A31) (S)-2-amino-5-(isonicotinamido)pentanoic acid
Orn(A32) (S)-2-amino-5-(nicotinamido)pentanoic acid
Orn(A33) (S)-2-amino-5-(picolinamido)pentanoic acid
Orn(A34) (S)-2-amino-5-(6-(trifluoromethyl)nicotinamido)pentanoic acid
Orn(A35) (S)-2-amino-5-(3-methoxybenzamido)pentanoic acid
Orn(A36) (S)-2-amino-5-(3-(difluoromethoxy)benzamido)pentanoic acid
Orn(A37) (S)-2-amino-5-(4-(methylsulfonyl)benzamido)pentanoic acid
Orn(A38) (S)-2-amino-5-(benzo[d][1,3]dioxole-5-carboxamido)pentanoic acid
Orn(A39) (S)-2-amino-5-(2-(pyridin-3-yl)acetamido)pentanoic acid
Orn(A40) (S)-2-amino-5-(pyrimidine-4-carboxamido)pentanoic acid
Orn(A41) (S)-2-amino-5-(pyrazine-2-carboxamido)pentanoic acid
Orn(A42) (S)-2-amino-5-(3-cyanobenzamido)pentanoic acid
Orn(A43) (S)-2-amino-5-(thiophene-2-carboxamido)pentanoic acid
Orn(A44) (S)-2-amino-5-(1-methyl-1H-pyrrole-2-carboxamido)pentanoic acid Orn(A45) (S)-2-amino-5-(thiazole-2-carboxamido)pentanoic acid
Orn(A46) (S)-2-amino-5-(thiazole-4-carboxamido)pentanoic acid
Orn(A47) (S)-2-amino-5-(1-methyl-1H-imidazole-2-carboxamido)pentanoic acid
Orn(A48) (S)-2-amino-5-(1-methyl-1H-imidazole-5-carboxamido)pentanoic acid
Orn(A49) (S)-2-amino-5-(1-methyl-1H-indole-2-carboxamido)pentanoic acid
Orn(A50) (S)-2-amino-5-(benzo[d]thiazole-2-carboxamido)pentanoic acid
Orn(A51) (S)-2-amino-5-(quinoxaline-2-carboxamido)pentanoic acid
Orn(A52) (S)-5-(3-(1H-indol-3-yl)propanamido)-2-aminopentanoic acid
Orn(A53) (S)-2-amino-5-(2-aminothiazole-4-carboxamido)pentanoic acid
Orn(A54) (S)-2-amino-5-(2-(2-aminothiazol-4-yl)acetamido)pentanoic acid
Orn(A55) (S)-2-amino-5-(4-guanidinobutanamido)pentanoic acid
Orn(A56) (S)-2-amino-5-(1,4,5,6-tetrahydropyrimidin-2-ylamino)pentanoic acid
Dab(Ar1) (S)-2-amino-4-(pyridin-2-ylamino)butanoic acid
Dab(Ar2) (S)-2-amino-4-(pyrimidin-2-ylamino)butanoic acid
Dab(Ar3) (S)-2-amino-4-(1,2,4-triazin-3-ylamino)butanoic acid
Dab(Ar4) (S)-2-amino-4-(pyridin-2-ylmethylamino)butanoic acid
Dab(Ar5) (S)-2-amino-4-(pyrimidin-2-ylmethylamino)butanoic acid
Dab(Ar6) (S)-2-amino-4-(bis(pyrimidin-2-ylmethyl)amino)butanoic acid
Dab(Ar7) (S)-2-amino-4-(((1-methyl-1H-imidazol-2-yl)methyl)amino)butanoic acid
Dab(Ar8) (S)-2-amino-4-(((4-methyl-4H-1,2,4-triazol-3-yl)methyl)amino)butanoic acid
Dab(Ar9) (S)-2-amino-4-(((1-methyl-1H-1,2,4-triazol-5-yl)methyl)amino)butanoic acid
Dab(Ar10) (S)-2-amino-4-(1H-pyrazol-1-yl)butanoic acid
Dab(Ar11) (S)-2-amino-4-(bis((1-methyl-1H-imidazol-2-yl)methyl)amino)-butanoic acid
Dab(Ar12) (S)-2-amino-4-(1H-1,2,4-triazol-1-yl)butanoic acid
Dab(S1) (S)-2-amino-4-(methylsulfonamido)butanoic acid
Dab(S2) (S)-2-amino-4-(ethylsulfonamido)butanoic acid
Dab(S3) (S)-2-amino-4-(1-methylethylsulfonamido)butanoic acid
Dab(S4) (S)-2-amino-4-(cyclopropanesulfonamido)butanoic acid
Dab(S5) (S)-2-amino-4-(2-methylpropylsulfonamido)butanoic acid
Dab(S6) (S)-2-amino-4-(2,2,2-trifluoroethylsulfonamido)butanoic acid
Dab(S7) (S)-2-amino-4-(cyclopentanesulfonamido)butanoic acid
Dab(S8) (S)-2-amino-4-(cyclohexanesulfonamido)butanoic acid
Dab(S9) (S)-2-amino-4-(tetrahydro-2H-pyran-4-sulfonamido)butanoic acid
Dab(S10) (S)-2-amino-4-(phenylsulfonamido)butanoic acid
Dab(S11) (S)-2-amino-4-(4-aminophenylsulfonamido)butanoic acid
Dab(S12) (S)-2-amino-4-(4-(dimethylamino)phenylsulfonamido)butanoic acid
Dab(S13) (S)-2-amino-4-(4-morpholinophenylsulfonamido)butanoic acid
Dab(S14) (S)-2-amino-4-(4-cyanophenylsulfonamido)butanoic acid
Dab(S15) (S)-2-amino-4-(5-cyanopyridine-2-sulfonamido)butanoic acid
Dab(S16) (S)-2-amino-4-(1H-pyrazole-4-sulfonamido)butanoic acid
Dab(S17) (S)-2-amino-4-(1H-1,2,4-triazole-5-sulfonamido)butanoic acid
Dab(S18) (S)-2-amino-4-(1,1-dimethylethylsulfonamido)butanoic acid
Dab(A1) (S)-4-acetamido-2-aminobutanoic acid
Dab(A2) (S)-2-amino-4-propionamidobutanoic acid
Dab(A3) (S)-2-amino-4-isobutyramidobutanoic acid
Dab(A4) (S)-2-amino-4-(cyclopropanecarboxamido)butanoic acid
Dab(A5) (S)-2-amino-4-(3,3,3-trifluoropropanamido)butanoic acid
Dab(A6) (S)-2-amino-4-(4,4,4-trifluorobutanamido)butanoic acid
Dab(A7) (S)-2-amino-4-(3-aminopropanamido)butanoic acid
Dab(A8) (S)-2-amino-4-(4-aminobutanamido)butanoic acid
Dab(A9) (S)-2-amino-4-(5-aminopentanamido)butanoic acid
Dab(A10) (S)-2-amino-4-(3-methoxypropanamido)butanoic acid
Dab(A11) (S)-2-amino-4-(3-(methylamino)propanamido)butanoic acid
Dab(A12) (S)-2-amino-4-(3-(dimethylamino)propanamido)butanoic acid
Dab(A13) (S)-2-amino-4-(3-(phenylamino)propanamido)butanoic acid
Dab(A14) (2S)-2-amino-4-(3-aminobutanamido)butanoic acid
Dab(A15) (S)-2-amino-4-(3-amino-3-methylbutanamido)butanoic acid
Dab(A16) (S)-2-amino-4-(3-(methylsulfonyl)propanamido)butanoic acid
Dab(A17) (S)-2-amino-4-(2-cyclopropylacetamido)butanoic acid
Dab(A18) (2S)-2-amino-4-(2-(pyrrolidin-3-yl)acetamido)butanoic acid
Dab(A19) (2S)-2-amino-4-(2-(pyrrolidin-2-yl)acetamido)butanoic acid
Dab(A20) (S)-2-amino-4-(2-(piperidin-4-yl)acetamido)butanoic acid
Dab(A21) (2S)-2-amino-4-(2-(piperidin-3-yl)acetamido)butanoic acid
Dab(A22) (2S)-2-amino-4-(2-(piperidin-2-yl)acetamido)butanoic acid
Dab(A23) (S)-2-amino-4-(3-(piperidin-1-yl)propanamido)butanoic acid
Dab(A24) (S)-2-amino-4-(3-(piperazin-1-yl)propanamido)butanoic acid
Dab(A25) (S)-2-amino-4-(3-(4-methylpiperazin-1-yl)propanamido)butanoic acid
Dab(A26) (S)-2-amino-4-(3-morpholinopropanamido)butanoic acid
Dab(A27) (S)-2-amino-4-(2-(1-aminocyclohexyl)acetamido)butanoic acid
Dab(A28) (S)-2-amino-4-(2-(4-aminotetrahydro-2H-pyran-4-yl)acetamido)-butanoic acid
Dab(A29) (2S)-2-amino-4-(2,2-dimethyl-1,3-dioxolane-4-carboxamido)butanoic acid
Dab(A30) (S)-2-amino-4-benzamidobutanoic acid Dab(A31) (S)-2-amino-4-(isonicotinamido)butanoic acid
Dab(A32) (S)-2-amino-4-(nicotinamido)butanoic acid
Dab(A33) (S)-2-amino-4-(picolinamido)butanoic acid
Dab(A34) (S)-2-amino-4-(6-(trifluoromethyl)nicotinamido) butanoic acid
Dab(A35) (S)-2-amino-4-(3-methoxybenzamido)butanoic acid
Dab(A36) (S)-2-amino-4-(3-(difluoromethoxy)benzamido) butanoic acid
Dab(A37) (S)-2-amino-4-(4-(methylsulfonyl)benzamido) butanoic acid
Dab(A38) (S)-2-amino-4-(benzo[d][1,3]dioxole-5-carboxamido)butanoic acid
Dab(A39) (S)-2-amino-4-(2-(pyridin-3-yl)acetamido)butanoic acid
Dab(A40) (S)-2-amino-4-(pyrimidine-4-carboxamido)butanoic acid
Dab(A41) (S)-2-amino-4-(pyrazine-2-carboxamido)butanoic acid
Dab(A42) (S)-2-amino-4-(3-cyanobenzamido)butanoic acid
Dab(A43) (S)-2-amino-4-(thiophene-2-carboxamido)butanoic acid
Dab(A44) (S)-2-amino-4-(1-methyl-1H-pyrrole-2-carboxamido)butanoic acid
Dab(A45) (S)-2-amino-4-(thiazole-2-carboxamido)butanoic acid
Dab(A46) (S)-2-amino-4-(thiazole-4-carboxamido)butanoic acid
Dab(A47) (S)-2-amino-4-(1-methyl-1H-imidazole-2-carboxamido)butanoic acid
Dab(A48) (S)-2-amino-4-(1-methyl-1H-imidazole-5-carboxamido)butanoic acid
Dab(A49) (S)-2-amino-4-(1-methyl-1H-indole-2-carboxamido)butanoic acid
Dab(A50) (S)-2-amino-4-(benzo[d]thiazole-2-carboxamido)butanoic acid
Dab(A51) (S)-2-amino-4-(quinoxaline-2-carboxamido)butanoic acid
Dab(A52) (S)-4-(3-(1H-indol-3-yl)propanamido)-2-aminobutanoic acid
Dab(A53) (S)-2-amino-4-(2-aminothiazole-4-carboxamido) butanoic acid
Dab(A54) (S)-2-amino-4-(2-(2-aminothiazol-4-yl)acetamido)butanoic acid
Dab(A55) (S)-2-amino-4-(4-guanidinobutanamido)butanoic acid
Dap(Ar1) (S)-2-amino-3-(pyridin-2-ylamino)propanoic acid
Dap(Ar2) (S)-2-amino-3-(pyrimidin-2-ylamino)propanoic acid
Dap(Ar3) (S)-2-amino-3-(1,2,4-triazin-3-ylamino)propanoic acid
Dap(Ar4) (S)-2-amino-3-(pyridin-2-ylmethylamino)propanoic acid
Dap(Ar5) (S)-2-amino-3-(pyrimidin-2-ylmethylamino)propanoic acid
Dap(Ar6) (S)-2-amino-3-(bis(pyrimidin-2-ylmethyl)amino) propanoic acid
Dap(Ar7) (S)-2-amino-3-((1-methyl-1H-imidazol-2-yl)methylamino)propanoic acid
Dap(Ar8) (S)-2-amino-3-((4-methyl-4H-1,2,4-triazol-3-yl) methylamino)-propanoic acid
Dap(Ar9) (S)-2-amino-3-((1-methyl-1H-1,2,4-triazol-5-yl) methylamino)-propanoic acid
Dap(Ar10) (S)-2-amino-3-(1H-pyrazol-1-ylamino)propanoic acid
Dap(Ar11) (S)-2-amino-3-(bis((1-methyl-1H-imidazol-2-yl)methyl)amino)-propanoic acid
Dap(Ar12) (S)-2-amino-3-(1H-1,2,4-triazol-1-yl)propanoic acid
Dap(S1) (S)-2-amino-3-(methylsulfonamido)propanoic acid
Dap(S2) (S)-2-amino-3-(ethylsulfonamido)propanoic acid
Dap(S3) (S)-2-amino-3-(1-methylethylsulfonamido)propanoic acid
Dap(S4) (S)-2-amino-3-(cyclopropanesulfonamido)propanoic acid
Dap(S5) (S)-2-amino-3-(2-methylpropylsulfonamido)propanoic acid
Dap(S6) (S)-2-amino-3-(2,2,2-trifluoroethylsulfonamido) propanoic acid
Dap(S7) (S)-2-amino-3-(cyclopentanesulfonamido)propanoic acid
Dap(S8) (S)-2-amino-3-(cyclohexanesulfonamido)propanoic acid
Dap(S9) (S)-2-amino-3-(tetrahydro-2H-pyran-4-sulfonamido)propanoic acid
Dap(S10) (S)-2-amino-3-(phenylsulfonamido)propanoic acid
Dap(S11) (S)-2-amino-3-(4-aminophenylsulfonamido)propanoic acid
Dap(S12) (S)-2-amino-3-(4-(dimethylamino)phenylsulfonamido)propanoic acid
Dap(S13) (S)-2-amino-3-(4-morpholinophenylsulfonamido) propanoic acid
Dap(S14) (S)-2-amino-3-(4-cyanophenylsulfonamido)propanoic acid
Dap(S15) (S)-2-amino-3-(5-cyanopyridine-2-sulfonamido) propanoic acid
Dap(S16) (S)-2-amino-3-(1H-pyrazole-4-sulfonamido)propanoic acid
Dap(S17) (S)-2-amino-3-(1H-1,2,4-triazole-5-sulfonamido) propanoic acid
Dap(S18) (S)-2-amino-3-(1,1-dimethylethylsulfonamido) propanoic acid
Dap(A1) (S)-3-acetamido-2-aminopropanoic acid
Dap(A2) (S)-2-amino-3-propionamidopropanoic acid
Dap(A3) (S)-2-amino-3-isobutyramidopropanoic acid
Dap(A4) (S)-2-amino-3-(cyclopropanecarboxamido)propanoic acid
Dap(A5) (S)-2-amino-3-(3,3,3-trifluoropropanamido)propanoic acid
Dap(A6) (S)-2-amino-3-(4,4,4-trifluorobutanamido)propanoic acid
Dap(A7) (S)-2-amino-3-(3-aminopropanamido)propanoic acid
Dap(A8) (S)-2-amino-3-(4-aminobutanamido)propanoic acid
Dap(A9) (S)-2-amino-3-(5-aminopentanamido)propanoic acid
Dap(A10) (S)-2-amino-3-(3-methoxypropanamido)propanoic acid
Dap(A11) (S)-2-amino-3-(3-(methylamino)propanamido) propanoic acid
Dap(A12) (S)-2-amino-3-(3-(dimethylamino)propanamido) propanoic acid
Dap(A13) (S)-2-amino-3-(3-(phenylamino)propanamido) propanoic acid
Dap(A14) (2S)-2-amino-3-(3-aminobutanamido)propanoic acid
Dap(A15) (S)-2-amino-3-(3-amino-3-methylbutanamido) propanoic acid
Dap(A16) (S)-2-amino-3-(3-(methylsulfonyl)propanamido) propanoic acid
Dap(A17) (S)-2-amino-3-(2-cyclopropylacetamido)propanoic acid Dap(A18) (2S)-2-amino-3-(2-(pyrrolidin-3-yl)acetamido)propanoic acid
Dap(A19) (2S)-2-amino-3-(2-(pyrrolidin-2-yl)acetamido)propanoic acid
Dap(A20) (S)-2-amino-3-(2-(piperidin-4-yl)acetamido)propanoic acid
Dap(A21) (2S)-2-amino-3-(2-(piperidin-3-yl)acetamido)propanoic acid
Dap(A22) (2S)-2-amino-3-(2-(piperidin-2-yl)acetamido)propanoic acid
Dap(A23) (S)-2-amino-3-(3-(piperidin-1-yl)propanamido)propanoic acid
Dap(A24) (S)-2-amino-3-(3-(piperazin-1-yl)propanamido)propanoic acid
Dap(A25) (S)-2-amino-3-(3-(4-methylpiperazin-1-yl)propanamido)propanoic acid
Dap(A26) (S)-2-amino-3-(3-morpholinopropanamido)propanoic acid
Dap(A27) (S)-2-amino-3-(2-(1-aminocyclohexyl)acetamido)propanoic acid
Dap(A28) (S)-2-amino-3-(2-(4-aminotetrahydro-2H-pyran-4-yl)acetamido)-propanoic acid
Dap(A29) (2S)-2-amino-3-(2,2-dimethyl-1,3-dioxolane-4-carboxamido)propanoic acid
Dap(A30) (S)-2-amino-3-benzamidopropanoic acid
Dap(A31) (S)-2-amino-3-(isonicotinamido)propanoic acid
Dap(A32) (S)-2-amino-3-(nicotinamido)propanoic acid
Dap(A33) (S)-2-amino-3-(picolinamido)propanoic acid
Dap(A34) (S)-2-amino-3-(6-(trifluoromethyl)nicotinamido)propanoic acid
Dap(A35) (S)-2-amino-3-(3-methoxybenzamido)propanoic acid
Dap(A36) (S)-2-amino-3-(3-(difluoromethoxy)benzamido)propanoic acid
Dap(A37) (S)-2-amino-3-(4-(methylsulfonyl)benzamido)propanoic acid
Dap(A38) (S)-2-amino-3-(benzo[d][1,3]dioxole-5-carboxamido)propanoic acid
Dap(A39) (S)-2-amino-3-(2-(pyridin-3-yl)acetamido)propanoic acid
Dap(A40) (S)-2-amino-3-(pyrimidine-4-carboxamido)propanoic acid
Dap(A41) (S)-2-amino-3-(pyrazine-2-carboxamido)propanoic acid
Dap(A42) (S)-2-amino-3-(3-cyanobenzamido)propanoic acid
Dap(A43) (S)-2-amino-3-(thiophene-2-carboxamido)propanoic acid
Dap(A44) (S)-2-amino-3-(1-methyl-1H-pyrrole-2-carboxamido)propanoic acid
Dap(A45) (S)-2-amino-3-(thiazole-2-carboxamido)propanoic acid
Dap(A46) (S)-2-amino-3-(thiazole-4-carboxamido)propanoic acid
Dap(A47) (S)-2-amino-3-(1-methyl-1H-imidazole-2-carboxamido)propanoic acid
Dap(A48) (S)-2-amino-3-(1-methyl-1H-imidazole-5-carboxamido)propanoic acid
Dap(A49) (S)-2-amino-3-(1-methyl-1H-indole-2-carboxamido)propanoic acid
Dap(A50) (S)-2-amino-3-(benzo[d]thiazole-2-carboxamido)propanoic acid
Dap(A51) (S)-2-amino-3-(quinoxaline-2-carboxamido)propanoic acid
Dap(A52) (S)-3-(3-(1H-indol-3-yl)propanamido)-2-aminopropanoic acid
Dap(A53) (S)-2-amino-3-(2-aminothiazole-4-carboxamido)propanoic acid
Dap(A54) (S)-2-amino-3-(2-(2-aminothiazol-4-yl)acetamido)propanoic acid
Dap(A55) (S)-2-amino-3-(4-guanidinobutanamido)propanoic acid The abbreviation of D-isomers, e.g. $^D$Lys(Ar1) corresponds to the epimer at the 2-position of the appropriate amino acid described above.

In a preferred embodiment of the invention the compounds of the general formula (I) are selected from the group consisting of:

cyclo(-Ile-$^D$Arg-Arg-Ile-$^D$Pro-Thr-);
cyclo(-Ile-$^D$Arg-Arg-Tyr-$^D$Pro-Thr-);
cyclo(-Ile-$^D$Arg-Lys-Trp-$^D$Pro-Thr-);
cyclo(-Ile-$^D$Arg-Dab-Trp-$^D$Pro-Thr-);
cyclo(-Ile-$^D$Dab-Arg-Trp-$^D$Pro-Thr-);
cyclo(-Ile-$^D$Arg-Arg-Phe-$^D$Pro-Thr-);
cyclo(-Ile-$^D$Thr-Arg-Trp-$^D$Pro-Thr-);
cyclo(-Ile-$^D$Arg-Arg-Trp-$^D$Pro-hSer-);
cyclo(-Ile-$^D$Arg-Arg-Trp-$^D$Pro-alloThr-);
cyclo(-1Nal-$^D$Arg-Arg-Trp-$^D$Pro-Thr-);
cyclo(-Ile-$^D$Lys-Arg-Trp-$^D$Pro-Thr-);
cyclo(-Ile-$^D$His-Arg-Trp-$^D$Pro-Thr-);
cyclo(-Ile-$^D$Cit-Arg-Trp-$^D$Pro-Thr-);
cyclo(-Ile-$^D$Arg-Arg-Trp-$^D$Pip-Thr-);
cyclo(-Ile-$^D$Arg-Arg-2Nal-$^D$Pro-Thr-);
cyclo(-Ile-$^D$Arg-Arg-1Nal-$^D$Pro-Thr-);
cyclo(-Ile-$^D$Arg-Trp-Arg-$^D$Pro-Thr-);
cyclo(-Ile-$^D$Arg-Arg-Trp-$^D$Pro-Thr-);
cyclo(-Thr-$^D$Arg-Trp-Arg-$^D$Pro-Thr-);
cyclo(-Trp-$^D$Arg-Arg-Trp-$^D$Pro-Thr-);
cyclo(-Ile-$^D$Arg-Arg-Trp-$^D$Pro-Pro((3S)OH)—);
cyclo(-Ile-$^D$Arg-Arg-Trp-$^D$Pro-Ser-);
cyclo(-Ile-$^D$Arg-Agp-Trp-$^D$Pro-Thr-);
cyclo(-Ile-$^D$Arg-Agb-Trp-$^D$Pro-Thr-);
cyclo(-Trp-$^D$Phe-Trp-Arg-$^D$Pro((4S)NH$_2$)-Tic-);
cyclo(-Trp-$^D$Phe-Trp-Arg-$^D$Pro((4R)NH$_2$)-Tic-);
cyclo(-Ala-$^D$Phe-Trp-Arg-$^D$Pro((4R)NH$_2$)-Tic-);
cyclo(-Tyr-$^D$Phe-Trp-Arg-$^D$Pro((4R)NH$_2$)-Tic-);
cyclo(-Trp-$^D$Phe-Trp-Orn-$^D$Pro((4R)NH$_2$)-Tic-);
cyclo(-Trp-$^D$Phe-Trp-Dab-$^D$Pro((4R)NH$_2$)-Tic-);
cyclo(-Trp-$^D$Phe-Trp-Lys-$^D$Pro((4R)NH$_2$)-Tic-);
cyclo(-Trp-$^D$Phe-Trp-His-$^D$Pro((4R)NH$_2$)-Tic-);
cyclo(-Arg-$^D$Phe-Trp-Arg-$^D$Pro((4R)NH$_2$)-Tic-);
cyclo(-Pip-$^D$Phe-Trp-Arg-$^D$Pro((4R)NH$_2$)-Tic-);
cyclo(-hArg-$^D$Phe-Trp-Arg-$^D$Pro((4R)NH$_2$)-Tic-);
cyclo(-Agb-$^D$Phe-Trp-Arg-$^D$Pro((4R)NH$_2$)-Tic-);
cyclo(-3 Pal-$^D$Phe-Trp-Arg-$^D$Pro((4R)NH$_2$)-Tic-);
cyclo(-Trp-$^D$3Pal-Trp-Arg-$^D$Pro((4R)NH$_2$)-Tic-);
cyclo(-Arg-$^D$Phe-Trp-hArg-$^D$Pro((4R)NH$_2$)-Tic-);
cyclo(-Arg-$^D$Phe-Trp-Arg-$^D$Pro((4S)NH$_2$)-Tic-);
cyclo(-Trp-$^D$Phe-Trp-Arg-$^D$Pro((4R)NH$_2$)-Oic-);
cyclo(-Arg-$^D$Phe-Trp-Arg-$^D$Pro((4R)NH$_2$)-Oic-);
cyclo(-Trp-$^D$Phe-Trp-Arg-$^D$Pro-Pro((4S)F)—);
cyclo(-Trp-$^D$Phe-Trp-Arg-$^D$Pro-Pro((4S)NH$_2$)—);
cyclo(-Trp-$^D$Phe-Trp-Arg-$^D$Pro-Pro((4R)NH$_2$)—);
cyclo(-Trp-$^D$Phe-Trp-Arg-$^D$Pro-Mor-);
cyclo(-Ile-$^D$Arg-Arg-Trp-$^D$Pro-Mor-);
cyclo(-Arg-$^D$Phe-Trp-Arg-$^D$Pro-(4S)-Hyp(Bn)-);
cyclo(-Trp-$^D$Phe-Trp-Arg-$^D$Pro((4S)OH)-(4S)-Hyp(Bn)-);
cyclo(-Trp-$^D$Phe-Trp-Arg-$^D$Pro((4R)NH$_2$)-(4S)-Hyp(Bn)-);
cyclo(-His-$^D$Trp-His-Trp-$^D$Pro-Pro((4S)NHBz)-);
cyclo(-1Nal-$^D$Arg-Arg-Trp-$^D$Pro-Pro((3S)OH)—);
cyclo(Ile-$^D$Arg-Arg-2Nal-$^D$Pro-Pro((3S)OH)—);

cyclo(Ile-$^D$Arg-Arg-Trp-$^D$Pip-Pro((3S)OH)—);
cyclo(-Ile-$^D$Arg-Arg-Trp-$^D$Pro((4S)OH)-Thr-);
cyclo(-Ile-$^D$Arg-Arg-Trp-$^D$Pro((4R)NH$_2$)-Thr-);
cyclo(-Val-$^D$Arg-Arg-Trp-$^D$Pro-Thr-);
cyclo(-Abu-$^D$Arg-Arg-Trp-$^D$Pro-Thr-);
cyclo(-Chg-$^D$Arg-Arg-Trp-$^D$Pro-Thr-);
cyclo(-Leu-$^D$Arg-Arg-Trp-$^D$Pro-Thr-);
cyclo(-Nle-$^D$Arg-Arg-Trp-$^D$Pro-Thr-);
cyclo(-Cha-$^D$Arg-Arg-Trp-$^D$Pro-Thr-);
cyclo(-Ile-$^D$Orn-Arg-Trp-$^D$Pro-Thr-);
cyclo(-Ile-$^D$Arg-Orn(A41)-Trp-$^D$Pro-Thr-);
cyclo(-Ile-$^D$Arg-Orn-Trp-$^D$Pro-Thr-);
cyclo(-Ile-$^D$Arg-hArg-Trp-$^D$Pro-Thr-);
cyclo(-Ile-$^D$Arg-Arg-Trp-$^D$Tic-Thr-);
cyclo(-Ile-$^D$Arg-Orn(Ar2)-Trp-$^D$Pro-Thr-);
cyclo(-Ile-$^D$Arg-Orn(Ar7)-Trp-$^D$Pro-Thr-);
cyclo(-Ile-$^D$Arg-Orn(Ar4)-Trp-$^D$Pro-Thr-);
cyclo(-Ile-$^D$Arg-Orn(A56)-Trp-$^D$Pro-Thr-);
cyclo(-Ile-$^D$Arg-Arg-Phe(4CF$_3$)-$^D$Pro-Thr-);
cyclo(-Trp-$^D$Phe-Trp-Orn(A56)-$^D$Pip-Pro((3S)OH)—);
cyclo(-Ala(1Pyraz)-$^D$Phe-Trp-Arg-$^D$Pro((4R)NH$_2$)-Tic-);
cyclo(-Ala(Tet)-$^D$Phe-Trp-Arg-$^D$Pro((4R)NH$_2$)-Tic-);
cyclo(-Orn(Ar2)-$^D$Phe-Trp-Arg-$^D$Pro((4R)NH$_2$)-Tic-);
cyclo(-Orn(A56)-$^D$Phe-Trp-Arg-$^D$Pro((4R)NH$_2$)-Tic-);
cyclo(-Trp-$^D$Phe-Trp-Orn(Ar7)-$^D$Pro((4R)NH$_2$)-Tic-);
cyclo(-Trp-$^D$Phe-Trp-Orn(A56)-$^D$Pro((4R)NH$_2$)-Tiq-);
cyclo(-Trp-$^D$Phe-Trp-Orn(A56)-$^D$Pro((4R)NH$_2$)-Tic-);
and pharmaceutically acceptable salts thereof.

In a most preferred embodiment of the invention the compounds of the general formula (I) are selected from the group consisting of:
cyclo(-Ile-$^D$Arg-Arg-Trp-$^D$Pip-Thr-);
cyclo(-Ile-$^D$Arg-Arg-2Nal-$^D$Pro-Thr-);
cyclo(-Ile-$^D$Arg-Arg-Trp-$^D$Pro-Thr-);
cyclo(-Ile-$^D$Arg-Arg-Trp-$^D$Pro-Ser-);
cyclo(-Trp-$^D$Phe-Trp-Arg-$^D$Pro((4R)NH$_2$)-Tic-);
cyclo(-Trp-$^D$Phe-Trp-Dab-$^D$Pro((4R)NH$_2$)-Tic-);
cyclo(-3 Pal-$^D$Phe-Trp-Arg-$^D$Pro((4R)NH$_2$)-Tic-);
cyclo(-Trp-$^D$Phe-Trp-Arg-$^D$Pro((4R)NH$_2$)-Oic-);
cyclo(-Trp-$^D$Phe-Trp-Arg-$^D$Pro((4S)OH)-(4S)-Hyp (Bn)-);
cyclo(-Ile-$^D$Arg-Arg-Trp-$^D$Pip-Pro((3S)OH)—);
cyclo(-Chg-$^D$Arg-Arg-Trp-$^D$Pro-Thr-);
cyclo(-Ile-$^D$Arg-hArg-Trp-$^D$Pro-Thr-);
and pharmaceutically acceptable salts thereof.

In an alternative most preferred embodiment of the invention the compounds of the general formula (I) are selected from the group consisting of:
cyclo(-Ile-$^D$Arg-Orn(Ar2)-Trp-$^D$Pro-Thr-);
cyclo(-Ile-$^D$Arg-Orn(Ar7)-Trp-$^D$Pro-Thr-);
cyclo(-Ile-$^D$Arg-Orn(Ar4)-Trp-$^D$Pro-Thr-);
cyclo(-Ile-$^D$Arg-Orn(A56)-Trp-$^D$Pro-Thr-);
cyclo(-Ile-$^D$Arg-Arg-Phe(4CF$_3$)-$^D$Pro-Thr-);
cyclo(-Trp-$^D$Phe-Trp-Orn(A56)-$^D$Pip-Pro((3S)OH)—);
cyclo(-Ala(1Pyraz)-$^D$Phe-Trp-Arg-$^D$Pro((4R)NH$_2$)-Tic-);
cyclo(-Ala(Tet)-$^D$Phe-Trp-Arg-$^D$Pro((4R)NH$_2$)-Tic-);
cyclo(-Orn(Ar2)-$^D$Phe-Trp-Arg-$^D$Pro((4R)NH$_2$)-Tic-);
cyclo(-Orn(Ar56)-$^D$Phe-Trp-Arg-$^D$Pro((4R)NH$_2$)-Tic-);
cyclo(-Trp-$^D$Phe-Trp-Orn(Ar7)-$^D$Pro((4R)NH$_2$)-Tic-);
cyclo(-Trp-$^D$Phe-Trp-Orn(A56)-$^D$Pro((4R)NH$_2$)-Tiq-);
cyclo(-Trp-$^D$Phe-Trp-Orn(A56)-$^D$Pro((4R)NH$_2$)-Tic-);
and pharmaceutically acceptable salts thereof.

A further embodiment of the invention relates to the preparation of the present β-hairpin peptidomimetics by a process which comprises the steps of
(a) coupling an appropriately functionalized solid support with an appropriately N-protected derivative of that amino acid which in the desired end-product is in position T$^1$ or T$^2$ or P$^1$ to P$^4$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according general formula (I) in —COOH to —NH$_2$ orientation; any functional group which may be present in said N-protected amino acid derivative being likewise appropriately protected;
(d) removing the N-protecting group from the product thus obtained;
(e) repeating steps (c) and (d) until all amino acid residues have been introduced;
(f) if desired, selectively deprotecting one or several protected functional group(s) present in the molecule and appropriately substituting the reactive group(s) thus liberated;
(g) detaching the product thus obtained from the solid support;
(h) cyclizing the product cleaved from the solid support;
(i) removing any protecting groups present on functional groups of any members of the chain of amino acid residues and, if desired, any protecting group(s) which may in addition be present in the molecule; and
(j) if desired, implementing additional chemical transformations of one or more reactive group(s) present in the molecule; and/or
(k) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable, salt.

The process of the invention can advantageously be carried out as parallel array synthesis to yield libraries of template-fixed β-hairpin peptidomimetics of the above general formula (I). Such parallel synthesis allow one to obtain arrays of numerous (normally 24 to 192, typically 96) compounds of general formula (I) in high yields and defined purities, minimizing the formation of dimeric and polymeric by-products. The proper choice of the functionalized solid-support (i.e. solid support plus linker molecule), template and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, Tetrahedron Lett. 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido)-aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl]-benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-meth-oxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula (I).

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxy-phenoxy)butyric acid-derived linker (HMPB-linker, Flörsheimer & Riniker, Peptides 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoro-ethanol/DCM (1:2:7) for about 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
    allyl
Tse trimethylsilylethyl
Tce trichloroethyl
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf 2,2,4,6,7-pentamethyldihydrobenzofuran-5-sulfonyl
for the hydroxy group (as is present e.g. in the side-chain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the template-fixed β-hairpin loop mimetics of formula (I). For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling it externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. If this activation is being carried out by means of the commonly used carbo-diimides, such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophosphate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium and uronium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing the fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula (I) is obtained as end-product.

For some compound of the present invention according general formula (I) additional synthetic steps are required. These transformations can be applied either on a partially deprotected cyclic or linear peptide, attached to or already released from the solid support, or on the final deprotected molecule as exemplified below.

Depending on its purity, this peptide derivative can be used directly for biological assays, or it has to be further purified, for example by preparative HPLC.

As mentioned earlier, it is thereafter possible, if desired, to convert a fully deprotected product of formula (I) thus obtained into a pharmaceutically acceptable salt or to convert a pharmaceutically acceptable, or unacceptable, salt thus obtained into the corresponding free compound of formula (I) or into a different, pharmaceutically acceptable, salt. Any of these operations can be carried out by methods well known in the art.

In general the building blocks for the peptidomimetics of the present invention can be synthesized according to the literature methods (examples described below) or are known to a person skilled in the art and/or are commercially available. A few additional new syntheses were carried out for this invention and are described in the examples. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron (Report)* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press, Oxford 1989, Chapter 7, p. 257-279). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

The β-hairpin peptidomimetics of this invention can be used in a wide range of applications in order to selectively modulate the activity of the CXCR7 receptor and are thus useful in the treatment of a variety of diseases and disorders mediated by or sustained through the activity of CXCR7 or in the support of therapeutic treatments of specific disease conditions of primarily different cause, for example but not limited to the areas of dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases and cancer, or the mobilisation of stem cells, in man or, due to their similar etiology, in other mammals.

Especially they can be used as agents for treating and/or preventing diseases or conditions such as, but not limited to, HIV infections, Epstein-Barr Virus infection; diabetes mellitus (Type I and/or Type II); conjunctivitis, scleritis, uveitis, rhinosinusitis, Whim syndrome, lupus erythematosus, osteoarthritis, rheumatoid arthritis, synovitis, psoriasis, multiple sclerosis, Crohns disease, inflammatory bowel disease, mixed connective tissue disease, chronic lymphocytic thyroiditis, Graves' disease, graft-versus-host disease, Sjögren's syndrome; dry eye syndrome, glaucoma, age-related macular degeneration; pulmonary arterial hypertension, pulmonary hypoxia, atherosclerosis, myocarditis, heart failure, such as myocardial infarction, arterial thrombosis, stroke, angiogenesis; chronic obstructive pulmonary disease, idiopathic pulmonary fibrosis, asthma; sarcoma, such as osteosarcoma, rhabdomyosarcoma, Kaposi's sarcoma, synovial sarcoma; lipoma, such as angiolipoma; glioblastoma multiforme, astrocytomas, neuroblastoma; carcinoma, such as adenocarcinoma; malignant epithelial and mucoepidermoid neoplasms, thyroid neoplasm, gonadal neoplasms, prostate cancer, breast cancer, melanoma, lung carcinoma, pancreatic carcinoma, colorectal cancer; solid tumors; lymphoma, such as Birkitt's lymphoma, Hodgkin's lymphoma, non-Hodgkin's lymphoma; multiple myeloma and leukemia; metastasis; for the inhibition of neointima formation; for stem cell mobilisation of peripheral blood stem cells and/or mesenchymal stem cells; for the mobilisation of endothelial or neuronal progenitor cells; or for different kinds of tissue-repair in human or other mammals.

For use as medicaments the β-hairpin peptidomimetics can be administered singly, as mixtures of several β-hairpin peptidomimetics or in combination with other pharmaceutically active agents. The β-hairpin peptidomimetics may be administered per se or applied as a pharmaceutical preparation, e.g. an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hank's solution, Ringer's solution, or physiological saline solution. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxy-methylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 3 years. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morpho-logical different solid state forms, which may or may not contain different amounts of solvent, e.g. hydrate remaining from the crystallization process.

The β-hairpin peptidomimetics of the invention, or compositions thereof, will generally be used in an amount effective to achieve the intended purpose. It is to be understood that the amount used will depend on a particular application.

For the use of treating or preventing diseases or disorders with an etiology comprising or associated with an increased or reduced activity of the CXCR7 receptor and its ligands (e.g. CXCL11 and CXCL12), the β-hairpin peptidomimetics of the invention or compositions thereof, are administered or applied in a therapeutically effective amount. Determination of a therapeutically effective amount is well within the capacities of those skilled in the art, especially in view of the detailed disclosure provided herein.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredients required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The invention will now be further described in the Examples below, which are intended as an illustration only and not as limiting the scope of the invention in any way.

The following abbreviations are used:
Boc tert-Butyloxycarbonyl
DBV Divinyl benzene
DIPEA Diisopropylethylamine
Fmoc Fluorenylmethyloxycarbonyl
HATU O-(7-Aza-benzotriazole-1-yl)-N,N,N',N'-tetramethyluronoium hexafluorophosphate
HBTU O-(Benzotriazol-1-yl)-N,N,N',N'-tetramethyluronium hexafluorophosphate
HCTU O-(6-Chlorobenzotriazol-1-yl)-N,N,N',N'-tetramethyluronium hexafluorophosphate
HOAt 7-Aza-1-hydroxy benzotriazole
HOBt 1-Hydroxybenzotriazole
PyBop® (Benzotriazol-1-yloxy)tripyrrolidinophosphonium hexafluorophosphate
TATU O-(7-Aza-benzotriazol-1-yl)-N,N,N',N'-tetramethyluronium tetrafluoroborate
TBTU 2-(1H-Benzotriazol-1-yl-)1,1,3,3-tetramethyluronium tetrafluoroborate
TIS Triisopropylsilane
TPP Triphenylphosphine
rt Room temperature
RT Retention time

EXAMPLES

1. Peptide Synthesis 1.1 General Synthetic Procedures

Two general methods, Method A and Method B, for the synthesis of the peptide-mimetics of the present invention are exemplified here. This is to demonstrate the concept in principle and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin

Method A:

0.5 g of 2-chlorotritylchloride resin (Barlos et al. *Tetrahedron Lett.* 1989, 30, 3943-3946) (100-200 mesh, polystyrene, 1% DBV crosslinked, 1.4 mmol/g loading, 0.7 mmol) was filled into a dried flask. The resin was suspended in $CH_2Cl_2$ (2.5 ml) and allowed to swell at room temperature for 30 min. The resin was treated with 0.43 mmol (0.6 eq) of the first suitably protected amino acid residue and 488 µl (4 eq) of diisopropylethylamine (DIPEA) in $CH_2Cl_2$ (2.5 ml), the mixture was shaken at 25° C. for 4 hours. The resin was washed with $CH_2Cl_2$ (1×), DMF (1×), $CH_2Cl_2$ (1×), DMF (1×), $CH_2Cl_2$ (2×). The resin was shaken in 30 ml $CH_2Cl_2$/MeOH/DIPEA (17:2:1) for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Method B:

In a dried flask, 2-chlorotritylchloride resin (100-200 mesh, polystyrene, 1% DBV crosslinked, 1.4 mmol/g loading) is swollen in dry $CH_2Cl_2$ for 30 min (7 ml $CH_2Cl_2$ per g resin). A solution of 0.8 eq of suitably side-chain protected Fmoc-AA-OH and 6 eq of DIPEA in dry $CH_2Cl_2$/DMF (4:1) (10 ml per g resin) is added. After shaking for 2-4 h at rt the resin is filtered and washed successively with $CH_2Cl_2$, DMF, $CH_2Cl_2$, DMF and $CH_2Cl_2$. Then a solution of dry $CH_2Cl_2$/MeOH/DIPEA (17:2:1) is added (10 ml per g resin). After shaking for 3×30 min the resin is filtered in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin is dried under high vacuum overnight. The final mass of resin is calculated before the qualitative control.

The following preloaded resins were prepared: Fmoc-Ile-2-chlorotrityl resin, Fmoc-Arg-2-chlorotrityl resin, Fmoc-Trp-2-chlorotrityl resin, Fmoc-Thr-2-chlorotrityl resin, Fmoc-$^D$Pro-2-chlorotrityl resin, Fmoc-Ser-2-chlorotrityl resin, Fmoc-Agp-2-chlorotrityl resin, Fmoc-Agb-2-chlorotrityl resin, Fmoc-Tic-2-chlorotrityl resin, Fmoc-Tiq-2-chlorotrityl resin, Fmoc-Oic-2-chlorotrityl resin, Fmoc-(4S)-Hyp(Bn)-2-chlorotrityl resin, Fmoc-Pro((4S)NHBz)-2-chlorotrityl resin, Fmoc-$^D$Pip-2-chlorotrityl resin, Fmoc-$^D$Pro((3S)OH-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel were placed approximately 60 mg (Method A) or 80 mg (Method B) of the above resin (weight of the resin before loading). The following reaction cycles were programmed and carried out:

Method A:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 5 equiv. Fmoc amino acid/DMF + 5 eq. HCTU + 10 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino acid residue.

Method B:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 3.5 equiv. Fmoc amino acid/DMF + 3.5 eq. HCTU + 7 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino acid residue.

After the synthesis of the fully protected peptide fragment had been terminated, the cleavage, cyclization and work up procedures, as described herein below, were used for the preparation of the final compounds.

Cleavage, Backbone Cyclization and Deprotection of the Peptide

After assembly of the linear peptide, the resin was suspended in 1 ml of 1% TFA in $CH_2Cl_2$ (v/v; 0.14 mmol) for 3 minutes and filtered, and the filtrate was neutralized with 1 ml of 20% DIPEA in $CH_2Cl_2$ (v/v; 1.15 mmol). This procedure was repeated four times to ensure completion of the cleavage. The resin was washed three times with 1 ml of $CH_2Cl_2$. The $CH_2Cl_2$ layers containing product were evaporated to dryness.

The fully protected linear peptide was solubilised in 8 ml of dry DMF. Then 2 eq. of HATU in dry DMF (1-2 ml) and 4 eq. of DIPEA in dry DMF (1-2 ml) were added to the peptide, followed by stirring for 16 h. The volatiles were removed by evaporation. The crude cyclic peptide was dissolved in 7 ml of $CH_2Cl_2$ and extracted three times with 4.5 ml 10% acetonitrile in water (v/v). The $CH_2Cl_2$ layers were evaporated to dryness.

To fully deprotect the peptide, 4-7 ml of cleavage cocktail TFA/TIS/$H_2O$ (95:2.5:2.5) were added, and the mixture was kept for 2.5-4 h at room temperature until the reaction was complete. The reaction mixture was evaporated to dryness and the crude peptide was dissolved in 7 ml 20% AcOH in water (v/v) and extracted three times with 4 ml diisopropyl ether. The aqueous layer was collected and evaporated to dryness, and the residue was purified by preparative reverse phase LC-MS.

Purification Procedure (Preparative Reverse Phase LC-MS)

Compounds were purified by reverse phase chromatography using a Vydac 218MS column, 30×150 mm (Cat No. 218MS103015), 10 µm or a Waters XBridge C18, 30×150 mm, 5 µm (Cat No. 186002982).

Mobile phases used were:
A: 0.1% TFA in water/acetonitrile 95:5 (v/v)
B: 0.1% TFA in acetonitrile Gradient slopes in the preparative runs were adapted each time based on analytical LC-MS analysis of the crude product of the synthesis. As an example a typical run (purification of Ex. 29) was executed with a flow rate of 35 ml/min running a gradient from 0-2 min. 25% B, 6.5 min. 45% B to a final of 6.6-10.7 min. 100% B (retention time: 4.99 min in this case). Detection: MS and UV @ 220 nm Fractions collected were evaporated using a Genevac HT4 evaporator or a Büchi system.

Alternatively for larger amounts the following LC-purification system was used:
Column: Vydac 218MS, 10 µm, 50×150 mm
Mobile phase A: 0.1% TFA in water
Mobile phase B: 0.1% TFA in acetonitrile
Flow rate: 150 ml/min
Detection: UV @ 220 nm After lyophilisation the products were obtained typically as white to off-white powders and analysed by HPLC-ESI- MS methods as described below. Analytical data after preparative HPLC purification are shown in Table 1.

1.2 Analytical Methods

Analytical Method A:

Analytical HPLC retention times (RT, in minutes) were determined using a Gemini NX column, 50×2.0 mm, (cod. 00B-4453-B0—Phenomenex) with the following solvents A ($H_2O$+0.1% TFA) and B ($CH_3CN$+0.085% TFA) and the gradient: 0-0.1 min: 97% A, 3% B; 2.7 min: 3% A, 97% B; 2.7-3 min: 3% A, 97% B; 3.05-3.3 min: 97% A, 3% B. Flow rate=0.8 ml/min at 45° C.

Analytical Method B:

Analytical HPLC retention times (RT, in minutes) were determined using a XBridge C18 column, 50×2.0 mm, (cod. 186003084-Waters) with the following solvents A ($H_2O$+0.1% TFA) and B ($CH_3CN$+0.085% TFA) and the gradient: 0-0.05 min: 97% A, 3% B; 3 min: 3% A 97% B; 3-3.6 min: 3% A, 97% B; 3.6-4.3 min: 97% A, 3% B. Flow rate=0.5 ml/min at 45° C.

Analytical Method C:

Analytical HPLC retention times (RT, in minutes) were determined using an Ascentis Express C18 column, 50×3.0 mm, (cod. 53811-U-Supelco) with the following solvents A ($H_2O$+0.1% TFA) and B ($CH_3CN$+0.085% TFA) and the gradient: 0-0.05 min: 97% A, 3% B; 2.95 min: 3% A 97% B; 2.95-3.15 min: 3% A, 97% B; 3.17-3.2 min: 97% A, 3% B. Flow rate=1.3 ml/min at 45° C.

Analytical Method C':

Analog method C, but running at 55° C.

Analytical Method D:

Analytical HPLC retention times (RT, in minutes) were determined using an Ascentis Express C18 column, 50×3.0 mm, (cod. 53811-U—Supelco) with the following solvents A ($H_2O$+0.1% TFA) and B ($CH_3CN$+0.085% TFA) and the gradient: 0-0.05 min: 97% A, 3% B; 3.4 min: 33% A 67% B; 3.45-3.65 min: 3% A, 97% B; 3.67-3.7 min: 97% A, 3% B. Flow rate=1.3 ml/min at 55° C.

1.3 Synthesis of Peptide Sequences

Examples 1-5 are shown in Table 1.

The peptides were synthesized according general Method B starting with the amino acid L-isoleucin, which was grafted to the resin (Fmoc-Ile-2-chlorotrityl resin). The linear peptides were synthesized on the solid support according to the procedure described above in the following sequence: Resin-Ile-Thr-$^D$Pro-$P^4$-$P^3$-$P^2$. The products were cleaved from the resin, cyclized, deprotected and purified by preparative reverse phase LC-MS as described above.

After lyophilisation, the products were obtained as white to off-white powders and characterised by HPLC-MS, analytical method A as described above. For analytical data, see Ex. 1, 2, 3, 4, 5 in Table 1.

Examples 6, 7 and 67 are shown in Table 1.

The peptides were synthesized according general Method B starting with the amino acid L-arginin, which was grafted to the resin (Fmoc-Arg-2-chlorotrityl resin). The linear peptides were synthesized on the solid support according to the procedure described above in the following sequence: Resin-Arg $P^2$-$P^1$-$T^2$-$T^1$-$P^4$. The products were cleaved from the resin, cyclized, deprotected and purified by preparative reverse phase LC-MS as described above.

After lyophilisation, the products were obtained as white powders and characterised by HPLC-MS, analytical method A as described above. For analytical data, see Ex. 6, 7, 67 in Table 1.

Example 8 and 9 are shown in Table 1.

The peptides were synthesized according general Method B starting with the amino acid L-tryptophan, which was grafted to the resin (Fmoc-Trp-2-chlorotrityl resin). The linear peptides were synthesized on the solid support according to the procedure described above in the following sequence: Resin-Trp-Arg-$^D$Arg-Ile-$T^2$-$T^1$. The products were cleaved from the resin, cyclized, deprotected and purified by preparative reverse phase LC-MS as described above.

After lyophilisation, the products were obtained as white powders and characterised by HPLC-MS, analytical method A as described above. For analytical data, see Ex. 8, 9 in Table 1.

Example 10-16 are shown in Table 1.

The peptides were synthesized according general Method B starting with the amino acid L-threonin, which was grafted to the resin (Fmoc-Thr-2-chlorotrityl resin). The linear peptides were synthesized on the solid support according to the procedure described above in the following sequence: Resin-Thr-$T^1$-$P^4$-$P^3$-$P^2$-$P^1$. The products were cleaved from the resin, cyclized, deprotected and purified by preparative reverse phase LC-MS as described above.

After lyophilisation, the products were obtained as white to off-white powders and characterised by HPLC-MS, analytical method A as described above. For analytical data, see Ex. 10, 11, 12, 13, 14, 15, 16 in Table 1.

Examples 17-20 are shown in Table 1.

The peptides were synthesized according general Method A starting with the amino acid D-proline, which was grafted to the resin (Fmoc-$^D$Pro-2-chlorotrityl resin). The linear peptides were synthesized on the solid support according to the procedure described above in the following sequence: Resin-$^D$Pro-$P^4$-$P^3$-$P^2$-$P^1$-$T^1$. The products were cleaved from the resin, cyclized, deprotected and purified by preparative reverse phase LC-MS as described above.

After lyophilisation, the products were obtained as white powders and characterised by HPLC-MS, analytical method A as described above, except Ex. 20, for which analytical method B was used. For analytical data, see Ex. 17, 18, 19, 20 in Table 1.

Examples 21, 52 and 53 are shown in Table 1.

The peptides were synthesized according general Method B starting with the amino acid D-proline, which was grafted to the resin (Fmoc-$^D$Pro-2-chlorotrityl resin). The linear peptides were synthesized on the solid support according to the procedure described above in the following sequence: Resin-$^D$Pro-$P^4$-$P^3$-$P^2$-$P^1$-$T^1$. The products were cleaved from the resin, cyclized, deprotected and purified by preparative reverse phase LC-MS as described above.

After lyophilisation, the products were obtained as white powders and characterised by HPLC-MS, analytical method C as described above, except Ex. 21, for which analytical method A was used. For analytical data, see Ex. 21, 52, 53 in Table 1.

Example 22 is shown in Table 1.

The peptide was synthesized according general Method B starting with the amino acid L-serin, which was grafted to the resin (Fmoc-Ser-2-chlorotrityl resin). The linear peptide was synthesized on the solid support according to the procedure described above in the following sequence: Resin-Ser-$^D$Pro-Trp-Arg-$^D$Arg-Ile. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 22 in Table 1.

Example 23 is shown in Table 1.

The peptide was synthesized according general Method B starting with the amino acid (S)-2-amino-3-guanidinopropanoic acid, which was grafted to the resin (Fmoc-Agp-2-chlorotrityl resin). The linear peptide was synthesized on the solid support according to the procedure described above in the following sequence: Resin-Agp-$^D$Arg-Ile-Thr-$^D$Pro-Trp. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 23 in Table 1.

Example 24 is shown in Table 1.

The peptide was synthesized according general Method B starting with the amino acid (S)-2-amino-4-guanidinobutanoic acid, which was grafted to the resin (Fmoc-Agb-2-chlorotrityl resin). The linear peptide was synthesized on the solid support according to the procedure described above in the following sequence: Resin-Agb-$^D$Arg-Ile-Thr-$^D$Pro-Trp. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 24 in Table 1.

Examples 25-40, 74, 75 and 78 are shown in Table 1.

The peptides were synthesized according general Method B starting with the amino acid (3S)-1,2,3,4-Tetrahydroisoquinoline-3-carboxylic acid, which was grafted to the resin (Fmoc-Tic-2-chlorotrityl resin). The linear peptides were synthesized on the solid support according to the procedure described above in the following sequence: Resin-Tic-$T^1$-$P^4$-$P^3$-$P^2$-$P^1$. The products were cleaved from the resin, cyclized, deprotected and purified by preparative reverse phase LC-MS as described above.

After lyophilisation, the products were obtained as white to off-white powders and characterised by HPLC-MS, analytical method C as described above, except Ex. 25 and 26, for which analytical method A was used and Ex. 74, 75 and 78, for which analytical method D was used. For analytical data, see Ex. 25, 26, 27, 28, 29, 30, 31, 32, 33, 34, 35, 36, 37, 38, 39, 40, 74, 75, 78 in Table 1.

Examples 41 and 42 are shown in Table 1.

The peptides were synthesized according general Method B starting with the amino acid (2S,3aS,7aS)-octahydro-1H-indole-2-carboxylic acid, which was grafted to the resin (Fmoc-Oic-2-chlorotrityl resin). The linear peptides were synthesized on the solid support according to the procedure described above in the following sequence: Resin-Oic-$^D$Pro ((4R)NH$_2$)-Arg-Trp-$^D$Phe-$P^1$. The products were cleaved from the resin, cyclized, deprotected and purified by preparative reverse phase LC-MS as described above. After lyophilisation, the products were obtained as white powders and characterised by HPLC-MS, analytical method C as described above. For analytical data, see Ex. 41, 42 in Table 1.

Examples 43-46 are shown in Table 1.

The peptides were synthesized according general Method B starting with the amino acid L-tryptophan, which was grafted to the resin (Fmoc-Trp-2-chlorotrityl resin). The linear peptides were synthesized on the solid support according to the procedure described above in the following sequence: Resin-Trp-$^D$Phe-Trp-$T^2$-$T^1$-$P^4$. The products were cleaved from the resin, cyclized, deprotected and purified by preparative reverse phase LC-MS as described above.

After lyophilisation, the products were obtained as white to off-white powders and characterised by HPLC-MS, analytical method C as described above. For analytical data, see Ex. 43, 44, 45, 46 in Table 1.

Example 47 is shown in Table 1.

The peptide was synthesized according general Method B starting with the amino acid L-tryptophan, which was grafted to the resin (Fmoc-Trp-2-chlorotrityl resin). The linear peptide was synthesized on the solid support according to the procedure described above in the following sequence: Resin-Trp-Arg-$^D$Arg-Ile-Mor-$^D$Pro. The product was cleaved from the resin, cyclized, deprotected and purified by preparative reverse phase LC-MS as described above.

After lyophilisation, the product was obtained as a white powder and characterised by HPLC-MS, analytical method C as described above. For analytical data, see Ex. 47 in Table 1.

Examples 48-50 are shown in Table 1.

The peptides were synthesized according general Method B starting with the amino acid (2S,4S)-4-(benzyloxy)pyrrolidine-2-carboxylic acid, which was grafted to the resin (Fmoc-(4S)-Hyp(Bn)-2-chlorotrityl resin). The linear peptides were synthesized on the solid support according to the procedure described above in the following sequence: Resin-(4S)-Hyp(Bn) $T^1$-$P^4$-$P^3$-$P^2$-$P^1$. The products were cleaved from the resin, cyclized, deprotected and purified by preparative reverse phase LC-MS as described above. After lyophilisation, the products were obtained as white to off-white powders and characterised by HPLC-MS, analytical method C as described above. For analytical data, see Ex. 48, 49, 50 in Table 1.

Example 51 is shown in Table 1.

The peptide was synthesized according general Method A starting with the amino acid (2S,4S)-4-benzamidopyrrolidine-2-carboxylic acid, which was grafted to the resin (Fmoc-Pro((4S)NHBz)-2-chlorotrityl resin). The linear peptide was synthesized on the solid support according to the procedure described above in the following sequence: Resin-Pro((4S)NHBz)-$^D$Pro-Trp-His-$^D$Tpr-His. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 51 in Table 1.

Example 54 is shown in Table 1.

The peptide was synthesized according general Method B starting with the amino acid (R)-piperidine-2-carboxylic acid, which was grafted to the resin (Fmoc-$^D$Pip-2-chlorotrityl resin). The linear peptide was synthesized on the solid support according to the procedure described above in the following sequence: Resin-$^D$Pip-Trp-Arg-$^D$Arg-Ile-Pro((3S)OH). The product was cleaved from the resin, cyclized, deprotected and purified by preparative reverse phase LC-MS as described above.

After lyophilisation, the product was obtained as a white powder and characterised by HPLC-MS, analytical method C as described above. For analytical data, see Ex. 54 in Table 1.

Example 55 is shown in Table 1.

The peptide was synthesized according general Method B starting with the amino acid (2R,3S)-3-hydroxypyrrolidine-2-carboxylic acid, which was grafted to the resin (Fmoc-$^D$Pro((3S)OH-2-chlorotrityl resin). The linear peptide was synthesized on the solid support according to the procedure described above in the following sequence: Resin-$^D$Pro((3S)OH-Trp-Arg-$^D$Arg-Ile-Thr). The product was cleaved from the resin, cyclized, deprotected and purified by preparative reverse phase LC-MS as described above.

After lyophilisation, the product was obtained as a white powder and characterised by HPLC-MS, analytical method C as described above. For analytical data, see Ex. 55 in Table 1.

Examples 56-66, 69, 70 and 72 are shown in Table 1.

The peptides were synthesized according general Method B starting with the amino acid L-threonin, which was grafted to the resin (Fmoc-Thr-2-chlorotrityl resin). The linear peptides were synthesized on the solid support according to the procedure described above in the following sequence: Resin-Thr-T$^1$-P$^4$-P$^3$-P$^2$-P$^1$. The products were cleaved from the resin, cyclized, deprotected and purified by preparative reverse phase LC-MS as described above.

After lyophilisation, the products were obtained as white to off-white powders and characterised by HPLC-MS, analytical method C as described above, except Ex. 69 and 70, for which analytical method C' was used and Ex. 72, for which analytical method D was used. For analytical data, see Ex. 56, 57, 58, 59, 60, 61, 62, 63, 64, 65, 66, 69, 70, 72 in Table 1.

Examples 71, 73, 77, 79 and 80 are shown in Table 1.

The peptides were synthesized according general Method B starting with the appropriate protected amino acid at the position T$^2$ or in case of Ex. 73 at the position T$^1$ according Table 1, which was grafted to the resin (Fmoc-T$^2$-chlorotrityl resin respectively Fmoc-T$^1$-chlorotrityl). The linear peptides were synthesized on the solid support according to the procedure described above in the following sequence: Resin-T$^2$-T$^1$-P$^4$-P$^3$-P$^2$-P$^1$ respectively Resin-T$^1$-P$^4$-P$^3$-P$^2$-P$^1$-T$^2$. At positions where the final amino acid Orn(A56) was intended, Fmoc-protected (S)-2-amino-5-(pyrimidin-2-yl-amino)pentanoic acid was used as starting material. The products were cleaved from the resin and cyclized. Deprotection according the above standard procedure using TFA/TIS/H$_2$O resulted in a reduction to the desired molecule containing the Orn(A56) residue. Consequently the compounds were purified by preparative reverse phase LC-MS as described above.

After lyophilisation, the products were obtained as white to off-white powders and characterised by HPLC-MS, analytical method D as described above, except Ex. 71, for which analytical method C' was used. For analytical data, see Ex. 71, 73, 77, 79, 80 in Table 1.

Example 68 is shown in Table 1.

The peptide was synthesized according general Method B starting with the amino acid L-threonin, which was grafted to the resin (Fmoc-Thr-2-chlorotrityl resin). The linear peptide was synthesized on the solid support according to the procedure described above in the following sequence: Resin-Thr-$^D$Pro-Trp-Orn(Ar2)-$^D$Arg-Ile. The product was cleaved from the resin and cyclized. In deviation from above general procedure, deprotection was done (avoiding TIS) with a mixture of TFA/H$_2$O (95:5) and monitored for completion. The compound was purified by preparative reverse phase LC-MS as described above.

After lyophilisation, the product was obtained as a white powder and characterised by HPLC-MS, analytical method D as described above. For analytical data, see Ex. 68 in Table 1.

Example 76 is shown in Table 1.

The peptide was synthesized according general Method B starting with the amino acid (3S)-1,2,3,4-Tetrahydroisoquinoline-3-carboxylic acid, which was grafted to the resin (Fmoc-Tic-2-chlorotrityl resin). The linear peptide was synthesized on the solid support according to the procedure described above in the following sequence: Resin-Tic-$^D$Pro((4R)NH$_2$)-Arg-Trp-$^D$Phe-Orn(Ar2). The product was cleaved from the resin and cyclized. In deviation from above general procedure, deprotection was done (avoiding TIS) with a mixture of TFA/H$_2$O (95:5) and monitored for completion. The compound was purified by preparative reverse phase LC-MS as described above.

After lyophilisation, the product was obtained as a white powder and characterised by HPLC-MS, analytical method D as described above. For analytical data, see Ex. 76 in Table 1.

1.4 Sequence Data

TABLE 1

Examples

| Ex. | Sequence ID | P1[a] | P2[a] | P3[a] | P4[a] | T1[a] | T2[a] | Synth. Method | Purity %[b] | [M + H]$^+$ | RT[c] | Anal. Method |
|---|---|---|---|---|---|---|---|---|---|---|---|---|
| 1 | SEQ ID NO: 1 | Ile | $^D$Arg | Arg | Ile | $^D$Pro | Thr | B | 97 | 737.4 | 1.40 | A |
| 2 | SEQ ID NO: 2 | Ile | $^D$Arg | Arg | Tyr | $^D$Pro | Thr | B | 98 | 787.3 | 1.30 | A |
| 3 | SEQ ID NO: 3 | Ile | $^D$Arg | Lys | Trp | $^D$Pro | Thr | B | >98 | 782.4 | 1.43 | A |
| 4 | SEQ ID NO: 4 | Ile | $^D$Arg | Dab | Trp | $^D$Pro | Thr | B | >98 | 754.3 | 1.42 | A |
| 5 | SEQ ID NO: 5 | Ile | $^D$Dab | Arg | Trp | $^D$Pro | Thr | B | 94 | 754.3 | 1.42 | A |
| 6 | SEQ ID NO: 6 | Ile | $^D$Arg | Arg | Phe | $^D$Pro | Thr | B | >98 | 771.3 | 1.44 | A |
| 7 | SEQ ID NO: 7 | Ile | $^D$Thr | Arg | Trp | $^D$Pro | Thr | B | 95 | 755.3 | 1.51 | A |
| 8 | SEQ ID NO: 8 | Ile | $^D$Arg | Arg | Trp | $^D$Pro | hSer | B | 92 | 810.4 | 1.42 | A |
| 9 | SEQ ID NO: 9 | Ile | $^D$Arg | Arg | Trp | $^D$Pro | alloThr | B | 97 | 810.4 | 1.44 | A |
| 10 | SEQ ID NO: 10 | 1Nal | $^D$Arg | Arg | Trp | $^D$Pro | Thr | B | 97 | 894.4 | 1.60 | A |
| 11 | SEQ ID NO: 11 | Ile | $^D$Lys | Arg | Trp | $^D$Pro | Thr | B | 92 | 782.4 | 1.42 | A |
| 12 | SEQ ID NO: 12 | Ile | $^D$His | Arg | Trp | $^D$Pro | Thr | B | 95 | 791.4 | 1.42 | A |
| 13 | SEQ ID NO: 13 | Ile | $^D$Cit | Arg | Trp | $^D$Pro | Thr | B | 88 | 811.4 | 1.50 | A |
| 14 | SEQ ID NO: 14 | Ile | $^D$Arg | Arg | Trp | $^D$Pip | Thr | B | 98 | 824.4 | 1.47 | A |
| 15 | SEQ ID NO: 15 | Ile | $^D$Arg | Arg | 2Nal | $^D$Pro | Thr | B | 92 | 821.4 | 1.56 | A |
| 16 | SEQ ID NO: 16 | Ile | $^D$Arg | Arg | 1Nal | $^D$Pro | Thr | B | 91 | 821.4 | 1.56 | A |
| 17 | SEQ ID NO: 17 | Ile | $^D$Arg | Trp | Arg | $^D$Pro | Thr | A | 98 | 810.5 | 1.28 | A |
| 18 | SEQ ID NO: 18 | Ile | $^D$Arg | Arg | Trp | $^D$Pro | Thr | A | 97 | 924.4[d] | 1.45 | A |
| 19 | SEQ ID NO: 19 | Thr | $^D$Arg | Trp | Arg | $^D$Pro | Thr | A | 95 | 912.4[d] | 1.24 | A |
| 20 | SEQ ID NO: 20 | Trp | $^D$Arg | Arg | Trp | $^D$Pro | Thr | A | 95 | 997.5[d] | 1.83 | B |
| 21 | SEQ ID NO: 21 | Ile | $^D$Arg | Arg | Trp | $^D$Pro | Pro((3S)OH) | B | 98 | 822.3 | 1.51 | A |
| 22 | SEQ ID NO: 22 | Ile | $^D$Arg | Arg | Trp | $^D$Pro | Ser | B | 90 | 796.4 | 1.40 | A |
| 23 | SEQ ID NO: 23 | Ile | $^D$Arg | Agp | Trp | $^D$Pro | Thr | B | 87 | 782.3 | 1.46 | A |
| 24 | SEQ ID NO: 24 | Ile | $^D$Arg | Agb | Trp | $^D$Pro | Thr | B | 98 | 796.3 | 1.47 | A |
| 25 | SEQ ID NO: 25 | Trp | $^D$Phe | Trp | Arg | $^D$Pro((4S)NH$_2$) | Tic | B | 95 | 947.4 | 1.75 | A |
| 26 | SEQ ID NO: 26 | Trp | $^D$Phe | Trp | Arg | $^D$Pro((4R)NH$_2$) | Tic | B | 90 | 947.3 | 1.74 | A |
| 27 | SEQ ID NO: 27 | Ala | $^D$Phe | Trp | Arg | $^D$Pro((4R)NH$_2$) | Tic | B | 94 | 832.5 | 1.44 | C |

TABLE 1-continued

Examples

| Ex. | Sequence ID | P1[a] | P2[a] | P3[a] | P4[a] | T1[a] | T2[a] | Synth. Method | Purity %[b] | [M + H]+ | RT[c] | Anal. Method |
|---|---|---|---|---|---|---|---|---|---|---|---|---|
| 28 | SEQ ID NO: 28 | Tyr | DPhe | Trp | Arg | DPro((4R)NH2) | Tic | B | 92 | 924.5 | 1.45 | C |
| 29 | SEQ ID NO: 29 | Trp | DPhe | Trp | Orn | DPro((4R)NH2) | Tic | B | 92 | 905.5 | 1.56 | C |
| 30 | SEQ ID NO: 30 | Trp | DPhe | Trp | Dab | DPro((4R)NH2) | Tic | B | 89 | 891.5 | 1.57 | C |
| 31 | SEQ ID NO: 31 | Trp | DPhe | Trp | Lys | DPro((4R)NH2) | Tic | B | 93 | 919.5 | 1.57 | C |
| 32 | SEQ ID NO: 32 | Trp | DPhe | Trp | His | DPro((4R)NH2) | Tic | B | 92 | 928.5 | 1.58 | C |
| 33 | SEQ ID NO: 33 | Arg | DPhe | Trp | Arg | DPro((4R)NH2) | Tic | B | 92 | 917.5 | 1.25 | C |
| 34 | SEQ ID NO: 34 | Pip | DPhe | Trp | Arg | DPro((4R)NH2) | Tic | B | 92 | 887.5 | 1.23 | C |
| 35 | SEQ ID NO: 35 | hArg | DPhe | Trp | Arg | DPro((4R)NH2) | Tic | B | 96 | 931.7 | 1.26 | C |
| 36 | SEQ ID NO: 36 | Agb | DPhe | Trp | Arg | DPro((4R)NH2) | Tic | B | 96 | 903.5 | 1.23 | C |
| 37 | SEQ ID NO: 37 | 3Pal | DPhe | Trp | Arg | DPro((4R)NH2) | Tic | B | 95 | 909.5 | 1.25 | C |
| 38 | SEQ ID NO: 38 | Trp | D3Pal | Trp | Arg | DPro((4R)NH2) | Tic | B | 80 | 948.5 | 1.24 | C |
| 39 | SEQ ID NO: 39 | Arg | DPhe | Trp | hArg | DPro((4R)NH2) | Tic | B | 88 | 1045.6[d] | 1.25 | C |
| 40 | SEQ ID NO: 40 | Arg | DPhe | Trp | Arg | DPro((4S)NH2) | Tic | B | 93 | 917.5 | 1.26 | C |
| 41 | SEQ ID NO: 41 | Trp | DPhe | Trp | Arg | DPro((4R)NH2) | Oic | B | 94 | 939.7 | 1.55 | C |
| 42 | SEQ ID NO: 42 | Arg | DPhe | Trp | Arg | DPro((4R)NH2) | Oic | B | 91 | 909.7 | 1.23 | C |
| 43 | SEQ ID NO: 43 | Trp | DPhe | Trp | Arg | DPro | Pro((4S)F) | B | 96 | 888.5 | 1.62 | C |
| 44 | SEQ ID NO: 44 | Trp | DPhe | Trp | Arg | DPro | Pro((4S)NH2) | B | >98 | 885.5 | 1.51 | C |
| 45 | SEQ ID NO: 45 | Trp | DPhe | Trp | Arg | DPro | Pro((4R)NH2) | B | 95 | 885.5 | 1.46 | C |
| 46 | SEQ ID NO: 46 | Trp | DPhe | Trp | Arg | DPro | Mor | B | 93 | 886.5 | 1.61 | C |
| 47 | SEQ ID NO: 47 | Ile | DArg | Arg | Trp | DPro | Mor | B | 74 | 822.5 | 1.39 | C |
| 48 | SEQ ID NO: 48 | Arg | DPhe | Trp | Arg | DPro | (4S)-Hyp(Bn) | B | 91 | 946.7 | 1.52 | C |
| 49 | SEQ ID NO: 49 | Trp | DPhe | Trp | Arg | DPro((4S)OH) | (4S)-Hyp(Bn) | B | 89 | 992.5 | 1.78 | C |
| 50 | SEQ ID NO: 50 | Trp | DPhe | Trp | Arg | DPro((4R)NH2) | (4S)-Hyp(Bn) | B | 86 | 991.7 | 1.63 | C |
| 51 | SEQ ID NO: 51 | His | DTrp | His | Trp | DPro | Pro((4S)NHBz) | A | 95 | 960.4 | 1.50 | A |
| 52 | SEQ ID NO: 52 | 1Nal | DArg | Arg | Trp | DPro | Pro((3S)OH) | B | 86 | 906.5 | 1.50 | C |
| 53 | SEQ ID NO: 53 | Ile | DArg | Arg | 2Nal | DPro | Pro((3S)OH) | B | 91 | 833.5 | 1.48 | C |
| 54 | SEQ ID NO: 54 | Ile | DArg | Arg | Trp | DPip | Pro((3S)OH) | B | 92 | 836.5 | 1.37 | C |
| 55 | SEQ ID NO: 55 | Ile | DArg | Arg | Trp | DPro((4S)OH) | Thr | B | 85 | 826.5 | 1.15 | C |
| 56 | SEQ ID NO: 56 | Ile | DArg | Arg | Trp | DPro((4R)NH2) | Thr | B | 72 | 825.5 | 1.19 | C |
| 57 | SEQ ID NO: 57 | Val | DArg | Arg | Trp | DPro | Thr | B | 88 | 796.5 | 1.20 | C |
| 58 | SEQ ID NO: 58 | Abu | DArg | Arg | Trp | DPro | Thr | B | 81 | 782.5 | 1.16 | C |
| 59 | SEQ ID NO: 59 | Chg | DArg | Arg | Trp | DPro | Thr | B | 96 | 836.5 | 1.34 | C |
| 60 | SEQ ID NO: 60 | Leu | DArg | Arg | Trp | DPro | Thr | B | 96 | 810.5 | 1.30 | C |
| 61 | SEQ ID NO: 61 | Nle | DArg | Arg | Trp | DPro | Thr | B | 96 | 810.5 | 1.31 | C |
| 62 | SEQ ID NO: 62 | Cha | DArg | Arg | Trp | DPro | Thr | B | 94 | 850.5 | 1.46 | C |
| 63 | SEQ ID NO: 63 | Ile | DOrn | Arg | Trp | DPro | Thr | B | 91 | 768.5 | 1.24 | C |
| 64 | SEQ ID NO: 64 | Ile | DArg | Orn(A41) | Trp | DPro | Thr | B | 93 | 874.5 | 1.41 | C |
| 65 | SEQ ID NO: 65 | Ile | DArg | Orn | Trp | DPro | Thr | B | 94 | 768.5 | 1.24 | C |
| 66 | SEQ ID NO: 66 | Ile | DArg | hArg | Trp | DPro | Thr | B | 91 | 824.5 | 1.28 | C |
| 67 | SEQ ID NO: 67 | Ile | DArg | Arg | Trp | DTic | Thr | B | 94 | 872.5 | 1.43 | C |
| 68 | SEQ ID NO: 68 | Ile | DArg | Orn(Ar2) | Trp | DPro | Thr | B | 93 | 846.3 | 1.74 | D |
| 69 | SEQ ID NO: 69 | Ile | DArg | Orn(Ar7) | Trp | DPro | Thr | B | 97 | 862.5 | 1.17 | C' |
| 70 | SEQ ID NO: 70 | Ile | DArg | Orn(Ar4) | Trp | DPro | Thr | B | 84 | 859.1 | 1.27 | C' |
| 71 | SEQ ID NO: 71 | Ile | DArg | Orn(A56) | Trp | DPro | Thr | B | 95 | 850.4 | 1.28 | C' |
| 72 | SEQ ID NO: 72 | Ile | DArg | Arg | Phe(4CF3) | DPro | Thr | B | 97 | 839.3 | 1.96 | D |
| 73 | SEQ ID NO: 73 | Trp | DPhe | Trp | Orn(A56) | DPip | Pro((3S)OH) | B | 93 | 940.7 | 2.22 | D |
| 74 | SEQ ID NO: 74 | Ala(1Pyraz) | DPhe | Trp | Arg | DPro((4R)NH2) | Tic | B | 97 | 898.7 | 1.85 | D |
| 75 | SEQ ID NO: 75 | Ala(Tet) | DPhe | Trp | Arg | DPro((4R)NH2) | Tic | B | 94 | 900.7 | 1.80 | D |
| 76 | SEQ ID NO: 76 | Orn(Ar2) | DPhe | Trp | Arg | DPro((4R)NH2) | Tic | B | 90 | 953.7 | 1.73 | D |
| 77 | SEQ ID NO: 77 | Orn(A56) | DPhe | Trp | Arg | DPro((4R)NH2) | Tic | B | 96 | 1071.7[d] | 1.55 | D |
| 78 | SEQ ID NO78 | Trp | DPhe | Trp | Orn(Ar7) | DPro((4R)NH2) | Tic | B | 92 | 999.7 | 2.08 | D |
| 79 | SEQ ID NO: 79 | Trp | DPhe | Trp | Orn(A56) | DPro((4R)NH2) | Tiq | B | 95 | 987.7 | 2.18 | D |
| 80 | SEQ ID NO: 80 | Trp | DPhe | Trp | Orn(A56) | DPro((4R)NH2) | Tic | B | 93 | 987.7 | 2.16 | D |

[a]Abbreviation of amino acid see listing above.
[b]%-purity of compounds after prep. HPLC.
[c]Retention Time with applied method.
[d][M + TFA + H]+

2. Biological Methods

2.1 Preparation of the Peptide Samples

Lyophilized peptides were weighed on a Microbalance (Mettler MX5) and dissolved in DMSO to a final concentration of 10 mM unless otherwise stated. Stock solutions were kept at +4° C., and protected from light.

2.2 CXCR7 β-Arrestin Recruitment Assay

The PathHunter CHO-CXCR7 (DiscoverX) assay was performed according to the manufacturer's protocol. In brief, CHO CXCR7 β-arrestin cells were seeded at a density of 5000 cells per well in 40 µl of F12 medium in black 96-half volume well culture plates and incubated overnight at 37° C. in a humidified atmosphere with 5% $CO_2$. The next day, serial dilutions of PEM compounds have been prepared in DMSO and subsequently diluted in HBSS buffer containing 0.1% BSA.

For agonistic assay, 10 µl of compound solution or a solution of stromal cell-derived factor-1 (SDF-1) as positive control was added to the cells with a final DMSO concentration of 1% (v/v). The plate was incubated for 90 min at 37° C. in 5% $CO_2$ incubator with gentle shaking (300 rpm) before addition of 40 ul of detection reagent per well. Reaction was developed for 90 min at room temperature in the dark with shaking, and chemiluminescence was measured with a Topcount (Perkin Elmer) luminescence counter.

2.3 Results

TABLE 2

Biological Results

| Ex. | Sequence ID | β-Arrestin EC$_{50}$ [nM] |
|---|---|---|
| 1 | SEQ ID NO: 1 | 79.7 ± 99.7 |
| 2 | SEQ ID NO: 2 | 83.7 ± 77.4 |
| 3 | SEQ ID NO: 3 | 78.7 ± 114.7 |
| 4 | SEQ ID NO: 4 | 87.0 ± 84.1 |
| 5 | SEQ ID NO: 5 | 48.4 ± 67.5 |
| 6 | SEQ ID NO: 6 | 46.4 ± 57.9 |
| 7 | SEQ ID NO: 7 | 53.2 ± 35.8 |
| 8 | SEQ ID NO: 8 | 346.6 ± 10.3 |
| 9 | SEQ ID NO: 9 | 291.7 ± 101.3 |
| 10 | SEQ ID NO: 10 | 28.5 ± 12.6 |
| 11 | SEQ ID NO: 11 | 86.7 ± 9.7 |
| 12 | SEQ ID NO: 12 | 545.7 ± 241.3 |
| 13 | SEQ ID NO: 13 | 472.5 ± 68.9 |
| 14 | SEQ ID NO: 14 | 0.1 ± 0.0 |
| 15 | SEQ ID NO: 15 | 0.4 ± 0.1 |
| 16 | SEQ ID NO: 16 | 17.9 ± 2.6 |
| 17 | SEQ ID NO: 17 | 62.5 ± 1.8 |
| 18 | SEQ ID NO: 18 | 6.7 ± 5.1 |
| 19 | SEQ ID NO: 19 | 17.2 ± 18.9 |
| 20 | SEQ ID NO: 20 | 538.2 ± 105.3 |
| 21 | SEQ ID NO: 21 | 122.8 ± 85.2 |
| 22 | SEQ ID NO: 22 | 12.8 ± 3.5 |
| 23 | SEQ ID NO: 23 | 90.5 ± 60.7 |
| 24 | SEQ ID NO: 24 | 22.3 ± 29.3 |
| 25 | SEQ ID NO: 25 | 17.5 ± 12.2 |
| 26 | SEQ ID NO: 26 | 6.1 ± 3.3 |
| 27 | SEQ ID NO: 27 | 322.0 ± 48.2 |
| 28 | SEQ ID NO: 28 | 20.9 ± 27.3 |
| 29 | SEQ ID NO: 29 | 26.1 ± 16.7 |
| 30 | SEQ ID NO: 30 | 13.6 ± 5.0 |
| 31 | SEQ ID NO: 31 | 137.6 ± 114.9 |
| 32 | SEQ ID NO: 32 | 20.4 ± 6.6 |
| 33 | SEQ ID NO: 33 | 248.0 ± 16.5 |
| 34 | SEQ ID NO: 34 | 882.0 ± 42.3 |
| 35 | SEQ ID NO: 35 | 12.2 ± 5.4 |
| 36 | SEQ ID NO: 36 | 452.5 ± 15.8 |
| 37 | SEQ ID NO: 37 | 5.1 ± 0.9 |
| 38 | SEQ ID NO: 38 | 6.1 ± 1.5 |
| 39 | SEQ ID NO: 39 | 352.0 ± 79.3 |
| 40 | SEQ ID NO: 40 | 13.1 ± 4.4 |
| 41 | SEQ ID NO: 41 | 20.9 ± 33.7 |
| 42 | SEQ ID NO: 42 | 20.5 ± 10.9 |
| 43 | SEQ ID NO: 43 | 119.1 ± 42.3 |
| 44 | SEQ ID NO: 44 | 36.9 ± 14.0 |
| 45 | SEQ ID NO: 45 | 26.9 ± 12.6 |
| 46 | SEQ ID NO: 46 | 132.5 ± 53.1 |
| 47 | SEQ ID NO: 47 | nd |
| 48 | SEQ ID NO: 48 | 76.9 ± 24.7 |
| 49 | SEQ ID NO: 49 | 7.6 ± 10.1 |
| 50 | SEQ ID NO: 50 | 6.6 ± 1.6 |
| 51 | SEQ ID NO: 51 | 413.5 ± 225.5 |
| 52 | SEQ ID NO: 52 | 13.7 ± 5.1 |
| 53 | SEQ ID NO: 53 | 76.8 ± 47.9 |
| 54 | SEQ ID NO: 54 | 8.2 ± 3.4 |
| 55 | SEQ ID NO: 55 | 632.5 ± 23.3 |
| 56 | SEQ ID NO: 56 | 948.5 ± 75.3 |
| 57 | SEQ ID NO: 57 | 271.0 ± 0.2 |
| 58 | SEQ ID NO: 58 | 329.8 ± 93.2 |
| 59 | SEQ ID NO: 59 | 6.7 ± 2.2 |
| 60 | SEQ ID NO: 60 | 5.3 ± 3.6 |
| 61 | SEQ ID NO: 61 | 2.8 ± 1.0 |
| 62 | SEQ ID NO: 62 | 37.7 ± 18.5 |
| 63 | SEQ ID NO: 63 | 23.3 ± 7.3 |
| 64 | SEQ ID NO: 64 | 518.0 ± 20.9 |
| 65 | SEQ ID NO: 65 | 816.5 ± 58.8 |
| 66 | SEQ ID NO: 66 | 11.0 ± 4.5 |
| 67 | SEQ ID NO: 67 | 14.2 ± 5.2 |
| 68 | SEQ ID NO: 68 | 453.3 ± 185.5 |
| 69 | SEQ ID NO: 69 | 336.50 ± 92.6 |
| 70 | SEQ ID NO: 70 | 4.6 ± 0.8 |
| 71 | SEQ ID NO: 71 | 3.2 ± 2.7 |
| 72 | SEQ ID NO: 72 | 4.5 ± 1.1 |
| 73 | SEQ ID NO: 73 | 14.0 ± 0.1 |
| 74 | SEQ ID NO: 74 | 29.9 ± 8.9 |
| 75 | SEQ ID NO: 75 | 28.1 ± 5.1 |
| 76 | SEQ ID NO: 76 | 209.0 ± 6.6 |
| 77 | SEQ ID NO: 77 | 181.0 ± 62.9 |
| 78 | SEQ ID NO: 78 | 145.0 ± 10.9 |
| 79 | SEQ ID NO: 79 | 46.9 ± 12.5 |
| 80 | SEQ ID NO: 80 | 33.4 ± 0.8 | nd = not determined

The invention claimed is:
1. Compounds of the general formula (I)

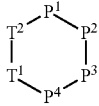

wherein the single elements T or P are connected in either direction from the carbonyl (C═O) point of attachment to the nitrogen (N) of the next element and wherein T¹ is ᴰPro; ᴰPip; ᴰTic; ᴰTiq; ᴰOic; ᴰAzt; ᴰPro((3R)OH); ᴰPro((3S)OH); ᴰPro((3R)NH₂); ᴰPro((3S)NH₂); ᴰPro((4R)OH); ᴰPro((4S)OH); ᴰPro((4R)NH₂); ᴰPro((4S)NH₂); ᴰPro((4S)NHBz); or ᴰMor;

T² is Thr; alloThr; Ser; hSer; Pro((3R)OH); Pro((3S)OH); Hyp(Bn); (4S)-Hyp(Bn); Pro((3R)NH₂); Pro((3S)NH₂); Pro((4R)NH₂); Pro((4S)NH₂); Pro((4S)F); Pro((4S)NHBz); or Mor; or when T¹ is ᴰPro((3R)OH); ᴰPro((3S)OH); ᴰPro((3R)NH₂); ᴰPro((3S)NH₂); ᴰPro((4R)NH₂); ᴰPro((4S)NH₂); ᴰPro((4S)NHBz); or ᴰMor then T² can in addition be Pro; Pip; Tic; Tiq; Oic; or Azt;

P¹ is Ile; Nle; Leu; Val; Chg; Cha; Abu; Ala; Ala(cPr); Ala(1Pyraz); Ala(Tet); Trp; 1Nal; 2Nal; Phe; Tyr; 2Pal; 3Pal; 4Pal; Thr; His; Arg; hArg; Agb; Pip; Orn(Ar2); or Orn(A56);

P² is ᴰArg; ᴰhArg; ᴰAgb; ᴰLys; ᴰOrn; ᴰCit; ᴰThr; ᴰDab; ᴰDap; ᴰPhe; ᴰTrp; ᴰHis; ᴰTyr; ᴰ2Pal; ᴰ3Pal; or ᴰ4Pal;

P³ is Arg; hArg; Agb; Agp; Lys; Orn; Orn(A41); Orn(A56); Orn(Ar2); Orn(Ar4); Orn(Ar7); Cit; Thr; Dab; Dap; Phe; Trp; His; Tyr; or Ile

P⁴ is Trp; His; Phe; Phe(4CF₃); 1Nal; 2Nal; Tyr; Leu; Ile; Arg; hArg; Lys; Dab; Dap; Orn; Orn(A56); or Orn(Ar7);

and pharmaceutically acceptable salts thereof.

2. Compounds according to claim 1 wherein
T¹ is ᴰPro; ᴰPip; ᴰTic; ᴰPro((4S)OH); ᴰPro((4R)NH₂); or ᴰPro((4S)NH₂);

T² is Thr; alloThr; Ser; hSer; Pro((3S)OH); (4S)-Hyp(Bn); Pro((4R)NH₂); Pro((4S)NH₂); Pro((4S)F); Pro((4S)NHBz); or Mor;

P¹ is Ile; Nle; Leu; Val; Chg; Cha; Abu; Ala; Trp; 1Nal; Tyr; 3Pal; Thr; His; Arg; hArg; Agb; Pip; Ala(1Pyraz); Ala(Tet); Orn(Ar2); or Orn(A56);

P² is ᴰArg; ᴰLys; ᴰOrn; ᴰCit; ᴰThr; ᴰDab; ᴰPhe; ᴰTrp; ᴰHis; or ᴰ3Pal;

P³ is Arg; hArg; Agb; Agp; Lys; Orn; Orn(A41); Orn(A56); Orn(Ar2); Orn(Ar4); Orn(Ar7); Dab; Trp; or His;

P⁴ is Trp; His; Phe; Phe(4CF₃); 1Nal; 2Nal; Tyr; Ile; Arg; hArg; Lys; Dab; Orn; Orn(A56); or Orn(Ar7);

and pharmaceutically acceptable salts thereof.

3. Compounds according claim 1 selected from
cyclo(-Ile-ᴰArg-Arg-Ile-ᴰPro-Thr-);
cyclo(-Ile-ᴰArg-Arg-Tyr-ᴰPro-Thr-);
cyclo(-Ile-ᴰArg-Lys-Trp-ᴰPro-Thr-);
cyclo(-Ile-ᴰArg-Dab-Trp-ᴰPro-Thr-);
cyclo(-Ile-ᴰDab-Arg-Trp-ᴰPro-Thr-);
cyclo(-Ile-ᴰArg-Arg-Phe-ᴰPro-Thr-);
cyclo(-Ile-ᴰThr-Arg-Trp-ᴰPro-Thr-);
cyclo(-Ile-ᴰArg-Arg-Trp-ᴰPro-hSer-);
cyclo(-Ile-ᴰArg-Arg-Trp-ᴰPro-alloThr-);
cyclo(-1Nal-ᴰArg-Arg-Trp-ᴰPro-Thr-);
cyclo(-Ile-ᴰLys-Arg-Trp-ᴰPro-Thr-);
cyclo(-Ile-ᴰHis-Arg-Trp-ᴰPro-Thr-);
cyclo(-Ile-ᴰCit-Arg-Trp-ᴰPro-Thr-);
cyclo(-Ile-ᴰArg-Arg-Trp-ᴰPip-Thr-);
cyclo(-Ile-ᴰArg-Arg-2Nal-ᴰPro-Thr-);
cyclo(-Ile-ᴰArg-Arg-1Nal-ᴰPro-Thr-);
cyclo(-Ile-ᴰArg-Trp-Arg-ᴰPro-Thr-);
cyclo(-Ile-ᴰArg-Arg-Trp-ᴰPro-Thr-);
cyclo(-Thr-ᴰArg-Trp-Arg-ᴰPro-Thr-);
cyclo(-Trp-ᴰArg-Arg-Trp-ᴰPro-Thr-);
cyclo(-Ile-ᴰArg-Arg-Trp-ᴰPro-Pro((3S)OH)—);
cyclo(-Ile-ᴰArg-Arg-Trp-ᴰPro-Ser-);
cyclo(-Ile-ᴰArg-Agp-Trp-ᴰPro-Thr-);
cyclo(-Ile-ᴰArg-Agb-Trp-ᴰPro-Thr-);
cyclo(-Trp-ᴰPhe-Trp-Arg-ᴰPro((4S)NH₂)-Tic-);
cyclo(-Trp-ᴰPhe-Trp-Arg-ᴰPro((4R)NH₂)-Tic-);
cyclo(-Ala-ᴰPhe-Trp-Arg-ᴰPro((4R)NH₂)-Tic-);
cyclo(-Tyr-ᴰPhe-Trp-Arg-ᴰPro((4R)NH₂)-Tic-);
cyclo(-Trp-ᴰPhe-Trp-Orn-ᴰPro((4R)NH₂)-Tic-);
cyclo(-Trp-ᴰPhe-Trp-Dab-ᴰPro((4R)NH₂)-Tic-);
cyclo(-Trp-ᴰPhe-Trp-Lys-ᴰPro((4R)NH₂)-Tic-);
cyclo(-Trp-ᴰPhe-Trp-His-ᴰPro((4R)NH₂)-Tic-);
cyclo(-Arg-ᴰPhe-Trp-Arg-ᴰPro((4R)NH₂)-Tic-);
cyclo(-Pip-ᴰPhe-Trp-Arg-ᴰPro((4R)NH₂)-Tic-);
cyclo(-hArg-ᴰPhe-Trp-Arg-ᴰPro((4R)NH₂)-Tic-);
cyclo(-Agb-ᴰPhe-Trp-Arg-ᴰPro((4R)NH₂)-Tic-);
cyclo(-3Pal-ᴰPhe-Trp-Arg-ᴰPro((4R)NH₂)-Tic-);
cyclo(-Trp-ᴰ3Pal-Trp-Arg-ᴰPro((4R)NH₂)-Tic-);
cyclo(-Arg-ᴰPhe-Trp-hArg-ᴰPro((4R)NH₂)-Tic-);
cyclo(-Arg-ᴰPhe-Trp-Arg-ᴰPro((4S)NH₂)-Tic-);
cyclo(-Trp-ᴰPhe-Trp-Arg-ᴰPro((4R)NH₂)-Oic-);
cyclo(-Arg-ᴰPhe-Trp-Arg-ᴰPro((4R)NH₂)-Oic-);
cyclo(-Trp-ᴰPhe-Trp-Arg-ᴰPro-Pro((4S)F)—);
cyclo(-Trp-ᴰPhe-Trp-Arg-ᴰPro-Pro((4S)NH₂)—);
cyclo(-Trp-ᴰPhe-Trp-Arg-ᴰPro-Pro((4R)NH₂)—);
cyclo(-Trp-ᴰPhe-Trp-Arg-ᴰPro-Mor-);
cyclo(-Ile-ᴰArg-Arg-Trp-ᴰPro-Mor-);
cyclo(-Arg-ᴰPhe-Trp-Arg-ᴰPro-(4S)-Hyp(Bn)-);
cyclo(-Trp-ᴰPhe-Trp-Arg-ᴰPro((4S)OH)-(4S)-Hyp(Bn)-);
cyclo(-Trp-ᴰPhe-Trp-Arg-ᴰPro((4R)NH₂)-(4S)-Hyp(Bn)-);
cyclo(-His-ᴰTrp-His-Trp-ᴰPro-Pro((4S)NHBz)-);
cyclo(-1Nal-ᴰArg-Arg-Trp-ᴰPro-Pro((3S)OH)—);
cyclo(-Ile-ᴰArg-Arg-2Nal-ᴰPro-Pro((3S)OH)—);
cyclo(-Ile-ᴰArg-Arg-Trp-ᴰPip-Pro((3S)OH)—);
cyclo(-Ile-ᴰArg-Arg-Trp-ᴰPro((4S)OH)-Thr-);
cyclo(-Ile-ᴰArg-Arg-Trp-ᴰPro((4R)NH₂)-Thr-);
cyclo(-Val-ᴰArg-Arg-Trp-ᴰPro-Thr-);
cyclo(-Abu-ᴰArg-Arg-Trp-ᴰPro-Thr-);
cyclo(-Chg-ᴰArg-Arg-Trp-ᴰPro-Thr-);
cyclo(-Leu-ᴰArg-Arg-Trp-ᴰPro-Thr-);
cyclo(-Nle-ᴰArg-Arg-Trp-ᴰPro-Thr-);
cyclo(-Cha-ᴰArg-Arg-Trp-ᴰPro-Thr-);
cyclo(-Ile-ᴰOrn-Arg-Trp-ᴰPro-Thr-);
cyclo(-Ile-ᴰArg-Orn(A41)-Trp-ᴰPro-Thr-);
cyclo(-Ile-ᴰArg-Orn-Trp-ᴰPro-Thr-);
cyclo(-Ile-ᴰArg-hArg-Trp-ᴰPro-Thr-);
cyclo(-Ile-ᴰArg-Arg-Trp-ᴰTic-Thr-);
cyclo(-Ile-ᴰArg-Orn(Ar2)-Trp-ᴰPro-Thr-);
cyclo(-Ile-ᴰArg-Orn(Ar7)-Trp-ᴰPro-Thr-);
cyclo(-Ile-ᴰArg-Orn(Ar4)-Trp-ᴰPro-Thr-);
cyclo(-Ile-ᴰArg-Orn(A56)-Trp-ᴰPro-Thr-);
cyclo(-Ile-ᴰArg-Arg-Phe(4CF₃)-ᴰPro-Thr-);
cyclo(-Trp-ᴰPhe-Trp-Orn(A56)-ᴰPip-Pro((3S)OH)—);
cyclo(-Ala(1Pyraz)-ᴰPhe-Trp-Arg-ᴰPro((4R)NH₂)-Tic-);
cyclo(-Ala(Tet)-ᴰPhe-Trp-Arg-ᴰPro((4R)NH₂)-Tic-);
cyclo(-Orn(Ar2)-ᴰPhe-Trp-Arg-ᴰPro((4R)NH₂)-Tic-);

cyclo(-Orn(A56)-$^D$Phe-Trp-Arg-$^D$Pro((4R)NH$_2$)-Tic-);
cyclo(-Trp-$^D$Phe-Trp-Orn(Ar7)-$^D$Pro((4R)NH$_2$)-Tic-);
cyclo(-Trp-$^D$Phe-Trp-Orn(A56)-$^D$Pro((4R)NH$_2$)-Tiq-);
cyclo(-Trp-$^D$Phe-Trp-Orn(A56)-$^D$Pro((4R)NH$_2$)-Tic-);
and pharmaceutically acceptable salts thereof.

4. Compounds according claim 3 selected from
cyclo(-Ile-$^D$Arg-Arg-Trp-$^D$Pip-Thr-);
cyclo(-Ile-$^D$Arg-Arg-2Nal-$^D$Pro-Thr-);
cyclo(-Ile-$^D$Arg-Arg-Trp-$^D$Pro-Thr-);
cyclo(-Ile-$^D$Arg-Arg-Trp-$^D$Pro-Ser-);
cyclo(-Trp-$^D$Phe-Trp-Arg-$^D$Pro((4R)NH$_2$)-Tic-);
cyclo(-Trp-$^D$Phe-Trp-Dab-$^D$Pro((4R)NH$_2$)-Tic-);
cyclo(-3Pal-$^D$Phe-Trp-Arg-$^D$Pro((4R)NH$_2$)-Tic-);
cyclo(-Trp-$^D$Phe-Trp-Arg-$^D$Pro((4R)NH$_2$)-Oic-);
cyclo(-Trp-$^D$Phe-Trp-Arg-$^D$Pro((4S)OH)-(4S)-Hyp(Bn)-);
cyclo(-Ile-$^D$Arg-Arg-Trp-$^D$Pip-Pro((3S)OH)—);
cyclo(-Chg-$^D$Arg-Arg-Trp-$^D$Pro-Thr-);
cyclo(-Ile-$^D$Arg-hArg-Trp-$^D$Pro-Thr-);
and pharmaceutically acceptable salts thereof.

5. Compounds according claim 3 selected from
cyclo(-Ile-$^D$Arg-Orn(Ar2)-Trp-$^D$Pro-Thr-);
cyclo(-Ile-$^D$Arg-Orn(Ar7)-Trp-$^D$Pro-Thr-);
cyclo(-Ile-$^D$Arg-Orn(Ar4)-Trp-$^D$Pro-Thr-);
cyclo(-Ile-$^D$Arg-Orn(A56)-Trp-$^D$Pro-Thr-);
cyclo(-Ile-$^D$Arg-Arg-Phe(4CF$_3$)-$^D$Pro-Thr-);
cyclo(-Trp-$^D$Phe-Trp-Orn(A56)-$^D$Pip-Pro((3S)OH)—);
cyclo(-Ala(1Pyraz)-$^D$Phe-Trp-Arg-$^D$Pro((4R)NH$_2$)-Tic-);
cyclo(-Ala(Tet)-$^D$Phe-Trp-Arg-$^D$Pro((4R)NH$_2$)-Tic-);
cyclo(-Orn(Ar2)-$^D$Phe-Trp-Arg-$^D$Pro((4R)NH$_2$)-Tic-);
cyclo(-Orn(Ar56)-$^D$Phe-Trp-Arg-$^D$Pro((4R)NH$_2$)-Tic-);
cyclo(-Trp-$^D$Phe-Trp-Orn(Ar7)-$^D$Pro((4R)NH$_2$)-Tic-);
cyclo(-Trp-$^D$Phe-Trp-Orn(A56)-$^D$Pro((4R)NH$_2$)-Tiq-);
cyclo(-Trp-$^D$Phe-Trp-Orn(A56)-$^D$Pro((4R)NH$_2$)-Tic-);
and pharmaceutically acceptable salts thereof.

6. Epimers and diastereomers of the compounds of claim 1.

7. A method of treating diseases or conditions mediated or sustained through the activity of CXCR7, which comprises administering to a subject in need thereof one or more compounds of claim 1.

8. Compounds according to claim 1 having modulating activity against the CXCR7 receptor, or interfering selectively with the natural activity of the CXCR7 receptor.

9. A pharmaceutical composition containing a compound or a mixture of compounds according to claim 1 and a pharmaceutically inert carrier.

10. Compositions according to claim 9 in a form suitable for oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, spray, nebuliser or suppositories.

11. A method of treating or of the supportive treatment of diseases or conditions linked to the activity of CXCR7, which comprises:
administering to a subject in need thereof one or more compounds according to claim 1,
wherein said diseases or conditions are selected from the group consisting of: dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases and oncology, or the mobilisation of stem cells, metastasis; inhibition of neointima formation; stem cell mobilisation of peripheral blood stem cells and/or mesenchymal stem cells; mobilisation of endothelial or neuronal progenitor cells; or for tissue-repair diseases or conditions.

12. A process for the preparation of compounds according to claim 1, which comprises:
(a) coupling a functionalized solid support with an N-protected derivative of that amino acid which in the desired end-product is in position T$^1$ or T$^2$ or P$^1$ to P$^4$ as defined in claim 1; any functional group which may be present in said N-protected amino acid derivative being likewise protected;
(b) removing the N-protecting group from the product obtained in step (a);
(c) coupling the product thus obtained with an N-protected derivative of that amino acid which in the desired end-product is in the position of the next element (T or P), following counterclockwise or clockwise the sequence according general formula (I) in —COOH to —NH$_2$ orientation; any functional group which may be present in said N-protected amino acid derivative being likewise protected;
(d) removing the N-protecting group from the product thus obtained;
(e) repeating steps (c) and (d) until all amino acid residues have been introduced;
(f) if desired, selectively deprotecting one or several protected functional group(s) present in the molecule and substituting the reactive group(s) thus liberated;
(g) detaching the product thus obtained from the solid support;
(h) cyclizing the product cleaved from the solid support;
(i) removing any protecting groups present on functional groups of any members of the chain of amino acid residues and, if desired, any protecting group(s) which may in addition be present in the molecule; and
(j) if desired, implementing additional chemical transformations of one or more reactive group(s) present in the molecule; and/or
(k) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable, salt.

13. The method of claim 1, wherein said diseases or conditions are selected from the group consisting of: HIV infections, Epstein-Barr Virus infection; diabetes mellitus (Type I and/or Type II); conjunctivitis, scleritis, uveitis, rhinosinusitis, Whim syndrome, lupus erythematosus, osteoarthritis, rheumatoid arthritis, synovitis, psoriasis, multiple sclerosis, Crohns disease, inflammatory bowel disease, mixed connective tissue disease, chronic lymphocytic thyroiditis, Graves' disease, graft-versus-host disease, Sjögren's syndrome; dry eye syndrome, glaucoma, age-related macular degeneration; pulmonary arterial hypertension, pulmonary hypoxia, atherosclerosis, myocarditis, heart failure, chronic obstructive pulmonary disease, idiopathic pulmonary fibrosis, asthma; sarcoma, multiple myeloma and leukemia.

14. The method of claim 13, wherein heart failure is myocardial infarction, arterial thrombosis, stroke and/or caused by angiogenesis.

15. The method of claim 13, wherein sarcoma is osteosarcoma, rhabdomyosarcoma, Kaposi's sarcoma and/or synovial sarcoma.

16. The method of claim 13, wherein lipoma is angiolipoma; glioblastoma multiforme, astrocytomas and/or neuroblastoma.

17. The method of claim 13, wherein carcinoma is adenocarcinoma, malignant epithelial and mucoepidermoid neoplasms, thyroid neoplasm, gonadal neoplasms, prostate cancer, breast cancer, melanoma, lung carcinoma, pancreatic carcinoma and/or colorectal cancer.

18. The method of claim 13, wherein lymphoma is Birkitt's lymphoma, Hodgkin's lymphoma, and/or non-Hodgkin's lymphoma.

\* \* \* \* \*